US008669283B2

(12) United States Patent
Sieber et al.

(10) Patent No.: US 8,669,283 B2
(45) Date of Patent: Mar. 11, 2014

(54) BETA-LACTONES AS ANTIBACTERIAL AGENTS

(75) Inventors: Stephan A. Sieber, Munich (DE); Thomas Böttcher, Maisach (DE)

(73) Assignee: Ludwig-Maximilians-Universitat Munchen, Munich (DE)

( * ) Notice: Subject to any disclaimer, the term of this patent is extended or adjusted under 35 U.S.C. 154(b) by 159 days.

(21) Appl. No.: 12/919,363

(22) PCT Filed: Feb. 4, 2009

(86) PCT No.: PCT/EP2009/000752
§ 371 (c)(1),
(2), (4) Date: Apr. 28, 2011

(87) PCT Pub. No.: WO2009/106211
PCT Pub. Date: Sep. 3, 2009

(65) Prior Publication Data
US 2011/0196027 A1     Aug. 11, 2011

(30) Foreign Application Priority Data
Feb. 26, 2008   (EP) ..................................... 08003463

(51) Int. Cl.
*A61K 31/337*     (2006.01)
(52) U.S. Cl.
USPC ........................................................ 514/449
(58) Field of Classification Search
USPC .................................. 514/449; 549/263, 265
See application file for complete search history.

(56) References Cited

U.S. PATENT DOCUMENTS

| 2004/0024050 A1 | 2/2004 | Smith et al. |
| 2006/0194071 A1 | 8/2006 | Yano et al. |

FOREIGN PATENT DOCUMENTS

| JP | 2011-502167 | 1/2011 |
| WO | WO 2008/006113 A2 | 1/2008 |
| WO | 2009-059046 | 5/2009 |

OTHER PUBLICATIONS

Asai et al., "Belactosin A, a Novel Antitumor Antibiotic Acting on Cyclin/CDK Mediated Cell Cycle Regulation, Produced by *Streptomyces* sp.," J. Antibiotics, Jan. 2000, pp. 81-83, vol. 53, No. 1.
Danheiser et al., "Synthesis of β-Lactones and Alkenes Via Thiol Esters: (E)-2,3-Dimethyl-3-Dodecene," pp. 61-72, 1996.
Lee et al., "Synthesis of Mycolic Acid Biosurfactants and Their Physical and Surface-Active Properties," JAOCS, 2005, pp. 181-88, vol. 82, No. 3.
Mullen et al., "Role of lipase in *Burkholderia cepacia* complex (Bcc) invasion of lung epithelial cells," Eur J Clin Microbiol Infect Dis, 2007, pp. 869-877, vol. 26.
PCT International Search Report, App. No. PCT/EP2009/000752, mail date of Jun. 4, 2009, 5 pages.
African Regional Intellectual Property Organization (AR/PO) Notification of Non-Compliance with Substantive Requirements and Invitation to Submit Observations and/or Amended Application, Application No. AP/P/2010/005377, mailed Jan. 8, 2013.
Notification of Reasons for Rejection, Japanese Application No. 2010-5479983, mailed Jun. 21, 2013.

*Primary Examiner* — Kristin Vajda
(74) *Attorney, Agent, or Firm* — Kagan Binder, PLLC

(57) ABSTRACT

The present invention relates to specific beta-lactone compounds and compositions thereof for the treatment of infections, such as, e.g., infections with bacteria or infections with protozoa, in particular infections with Gram-positive and/or Gram-negative bacteria and of infectious diseases caused by or related to Gram-positive and/or Gram-negative bacteria, and to the modulation of virulence of Gram-positive and/or Gram-negative bacteria or of protozoa by specific beta-lactone compounds. The invention further relates to the use of the compounds or compositions for preventing or eliminating biofilms.

21 Claims, 22 Drawing Sheets

A

B

A

B

A

B

BETA-LACTONES AS ANTIBACTERIAL AGENTS

CROSS-REFERENCE TO RELATED PATENT APPLICATIONS

Figure 1:
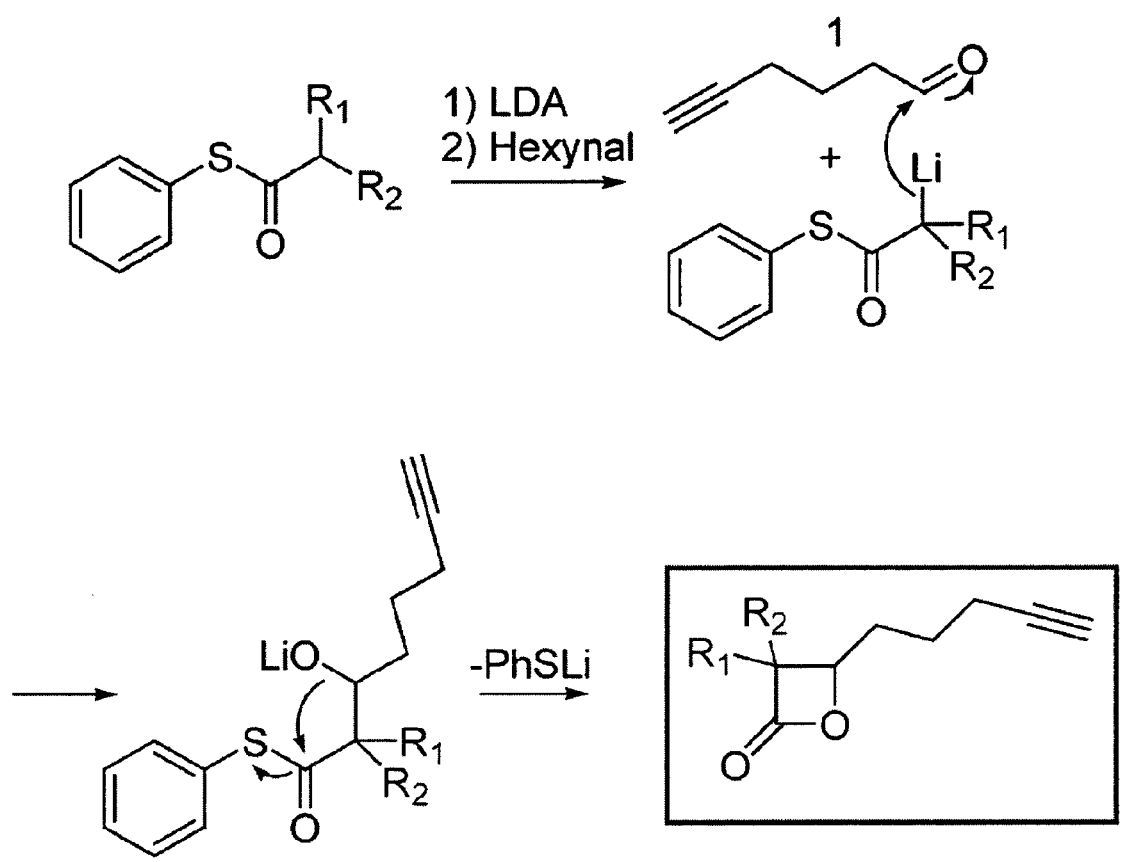

This application is the U.S. National Phase of PCT/EP2009/000752, filed Feb. 4, 2009, which claims priority to European Patent Application 08003463.0, filed Feb. 26, 2008, which is incorporated herein by reference in entirety.

The present invention relates to specific beta-lactone compounds and compositions thereof for the treatment of infections, such as, e.g., infections with bacteria or infections with protozoa, in particular infections with Gram-positive and/or Gram-negative bacteria and infectious diseases caused by or related to Gram-positive and/or Gram-negative bacteria, and to the modulation of virulence of Gram-positive and/or Gram-negative bacteria or of protozoa, like Plasmodium, by specific beta-lactone compounds. The invention further relates to the use of the compounds or compositions for preventing or eliminating biofilms.

After decades of successful treatment of bacterial infections with antibiotics, formerly treatable bacteria have developed drug resistance and consequently pose a major threat to public health. Since many antibiotics in clinical development and application still target only a limited set of cellular functions, it is a desirable goal to expand the number and breadth of therapeutic targets and gain a deeper understanding of the molecular mechanisms responsible for pathogenesis (Brötz-Oesterhelt et al., Mass. Spectrom. Rev. 2005, 24, 549). Brötz-Oesterhelt, Nat Med 11, 1082-1087 (2005) describes ClpP (a core unit of a bacterial protease complex) as target for acyldepsipeptides, which are structurally not related to the compound of the present invention. Said acyldepsipeptides are described as a new class of antibiotics having antibacterial activity against Gram-positive bacteria in vitro and in rodent models of bacterial infection.

Clardy, Nat Biotech 24, 1541-1550 (2006) describes new antibiotics which are derived from streptomycetes, actinomycetes, cyanobacteria and uncultured bacteria. The antibiotics described in Clardy inhibit, for example, the fatty acid biosynthesis, cell wall formation, and signal peptidases of bacteria. Clardy also describes acyldepsipeptidolactones (ADEPs) which target ClpP (caseinolytic protease). ADEPs dysregulate ClpP-dependent intracellular protease activity and thereby lead to accelerated protein degradation which in turn may lead to cell death.

Frees, Mol Microbiol 48, 1565-1578 (2003) investigates the role of ClpX (an ATPase) and ClpP in *Staphylococcus aureus* and conclude that ClpX and ClpP contribute to virulence by controlling the activity of virulence factors rather than by promoting stress tolerance. As Frees uses mutant bacterial strains for investigating the role of ClpP, inhibitors of ClpP are not described.

It is known in the art that ClpP may be used for screening putative antibacterial components. For example, WO 01/64855 describes, inter alia, the use of ClpP for the identification of agonists and antagonists of ClpP. Identified agonists/antagonists may then be used for the treatment of microbial infections and conditions associated with such infections. Exemplary antagonists described in WO 01/64855 are, for example, small organic molecules, peptides or peptide-like molecules, antibodies or oligonucleotides. However, beta-lactones for the treatment of bacterial infections are not disclosed.

Wang, Microbes and Infection 9, 1376-1383 (2007) elucidates the role of ClpP in biofilm formation and virulence of *Staphylococcus epidermis* via a mutant bacterial strain which has a point mutation in the catalytic center of ClpP. Wang speculates that ClpP may represent a potential drug target for inhibiting biofilm formation and virulence of *S. epidermis*. It is described in Wang, loc. cit. that said bacteria form biofilms on implanted medical devices and cause persistent infections. However, Wang concedes that such ClpP inhibitors remain to be discovered.

Though in the scientific and patent literature described above, the use of compounds targeting ClpP for the treatment of bacterial infections is described, beta-lactones as putative antibacterial or antiprotozoal agents are not referred to.

The following relates to beta-lactones and their medical use. Beta-lactones are well known as natural products and have been isolated from a variety of bacterial and fungal species (Parker et al., J. Antibiot. (Tokyo) 1982, 35, 900). Although β-lactones resemble the biologically highly active β-lactames, only a few β-lactone derived therapeutics have been used so far in clinical applications.

Herein below, structures of biologically active, naturally occurring β-lactones are shown:

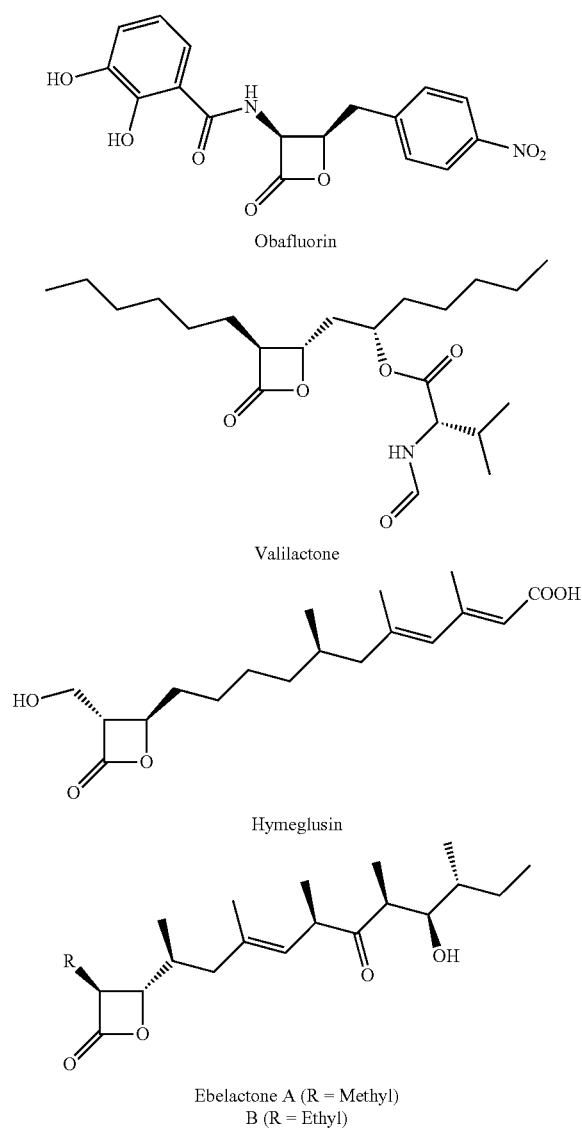

Obafluorin

Valilactone

Hymeglusin

Ebelactone A (R = Methyl)
B (R = Ethyl)

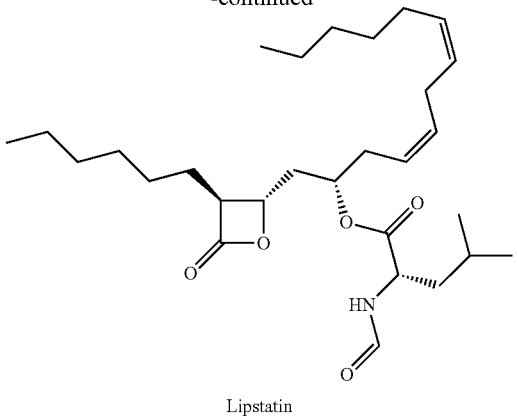

Lipstatin

Treatment of leucemia is desribed in Perchellet, Anticancer Res. 18, 97-106 (1998) which relates to the use of lactones for preventing the synthesis of macromolecules and the in vitro growth of leukemic cells. Also US 2006/0258620 describes the administration of beta-lactone for the treatment of cancer, inhibition of angiogenesis and the treatment of diseases and conditions that involve pathological angiogenesis.

Some β-lactones have also been shown to exhibit antibiotic or anti-obesity activities, e.g. Obafluorin (Tymiak et al., J. Org. Chem. 1985, 50, 5491; Pu et al., J. Org. Chem. 1991, 56, 1280), Hymeglusin (Aldridge et al., J. Chem. Soc. (Perkin 1) 1971, 23, 3888), and Lipstatin (Weibel et al., J. Antibiot. (Tokyo) 1987, 40, 1081).

The technical problem underlying the present invention is the provision of reliable means and methods for the highly efficient inhibition of the activity of pathogenic bacteria or pathogenic protozoa, particularly pathogenic bacteria, and more particularly pathogenic Gram-positive bacteria.

The technical problem is solved by provision of the embodiments provided herein and as characterized in the claims.

Accordingly, the present invention relates to the beta-lactone (2-oxetanone) compounds (also referred to as "beta-lactones" and beta-lactone derivatives) of formula (I) as defined in the following:

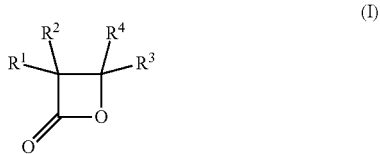

wherein:

$R^1$ is $C_{3-16}$ alkyl, $C_{3-16}$ alkenyl, $C_{3-16}$ alkynyl, which may be substituted and/or which may be interrupted by one or more heteroatoms or heterogroups selected from O and S or $NR^5$, with $R^5$ being selected from —H or —$C_{1-4}$ alkyl; phenyl which may be substituted; or $C_{7-12}$ aralkyl which may be substituted on the aryl ring, $R^2$ is H, $R^3$ is H; $C_{1-12}$ alkyl, $C_{2-12}$ alkenyl, $C_{2-12}$ alkynyl, which may be substituted and/or which may be interrupted by one or more heteroatoms or heterogroups selected from O and S or $NR^5$, with $R^5$ being selected from —H or —$C_{1-4}$ alkyl; phenyl which may be substituted; or $C_{7-12}$ aralkyl which may be substituted on the aryl ring, and $R^4$ is H or $C_{1-8}$ alkyl which may be substituted and/or which may be interrupted by one or more heteroatoms or heterogroups selected from O and S or $NR^5$, with $R^5$ being selected from —H or —$C_{1-4}$ alkyl, or $R^3$ and $R^4$ are taken together to form a 5- or 6-membered carbocyclic ring.

The present invention discloses the above compounds and pharmaceutically acceptable salts and prodrugs thereof for use in the treatment, amelioration or prevention of an infection, such as, e.g., a bacterial infection or a protozoan infection, and in particular a bacterial infection.

In accordance with the present invention, it was surprisingly found that beta-lactones, in particular beta-lactones and their derivatives as described herein, are particularly useful in the inhibition/suppression of bacterial or protozoan virulence. As illustratively shown in the appended examples, beta-lactones are particularly useful in the inhibition/suppression of the activity of virulence factors such as, e.g., the caseinolytic protease ClpP. Therefore, the inventive compounds (beta-lactones and derivatives thereof) are capable of interfering with virulence pathways in bacteria and protozoa, in particular virulence pathways in Gram-positive bacteria. Since the inhibition of virulence can not only lead to a suppression of symptoms in an individual suffering from such a bacterial (or protozoan) infection but can also lead to the complete extinction of the pathogenic organism. Accordingly, the beta-lactone compounds as described herein are not only useful in co-therapeutic medical intervention (for example, the co-treatment with antibiotics and/or antiseptics) but also in medical intervention per se. The beta-lactones as described herein are also useful in the cleaning of devices, in particular technical or medical devices, like catheters, medical implants, stents, contact lenses and the like. Accordingly, the beta-lactones of this invention can also be used in the sterilization of such devices, of laboratory equipment, of benches, of surfaces and the like.

Moreover, the compounds of formula (I) are effective for preventing the formation of biofilms or eliminating biofilms on surfaces of a technical device.

In the compounds of formula (I) above, the carbon atom carrying the substituents $R^1$ and $R^2$ will be referred to as carbon-3 or C-3, the carbon atom carrying the substituents $R^3$ and $R^4$ will be referred to as carbon-4 or C-4. The present invention encompasses all enantiomers and diastereomers of the compound of formula (I), i.e. those where the configuration of the C-atoms C-3 and C-4, if chiral, is (S, S), (S, R), (R, S) or (R, R), separately or as mixtures, in particular racemic mixtures. In a preferred embodiment, $R^1$ and $R^3$ are in a trans configuration. Thus, in one embodiment the present invention relates to a racemic mixture of compounds of formula (I), wherein $R^1$ and $R^3$ are in a trans configuration, particularly as antibacterial or antiprotozoal agent, more particularly as antibacterial agent.

In the compounds of formula (I), $R^1$ is $C_{3-16}$ alkyl, $C_{3-16}$ alkenyl, $C_{3-16}$ alkynyl, phenyl or $C_{7-12}$ aralkyl. An alkyl, alkenyl or alkynyl group as $R^1$ may be substituted. Independently, an alkyl, alkenyl or alkynyl group as $R^1$ may be interrupted by one or more heteroatoms or heterogroups independently selected from O, S and $NR^5$, with $R^5$ being selected from —H or —$C_{1-4}$ alkyl. Both a phenyl group or an aralkyl group as $R^1$ may be substituted on the aromatic ring.

Alkyl groups as $R^1$ preferably have 4 or more or even 6 or more carbon atoms, more preferably 7 or more or even 8 or more carbon atoms, and most preferably 9 or more carbon atoms. Preferably, the maximum number of carbon atoms is 14 or even 12. The alkyl groups may be linear or branched, with linear groups being preferred.

Alkenyl groups as $R^1$ preferably have 4 or more or even 6 or more carbon atoms, more preferably 7 or more or even 8 or more carbon atoms, and most preferably 9 or more carbon atoms. Preferably, the maximum number of carbon atoms is 14 or even 12. The alkenyl groups may be linear or branched, with linear groups being preferred. They have one or more, such as two or three, double bonds, and preferably have one double bond. A preferred position of a double bond is the omega-position of the alkenyl chain relative to the lactone ring.

Alkynyl groups as $R^1$ preferably have 4 or more or even 6 or more carbon atoms, more preferably 7 or more or even 8 or more carbon atoms, and most preferably 9 or more carbon atoms. Preferably, the maximum number of carbon atoms is 14 or even 12. The alkynyl groups may be linear or branched, with linear groups being preferred. They have one or more, such as two or three, triple bonds, and preferably have one triple bond. A preferred position of a triple bond is the omega-position of the alkynyl chain relative to the lactone ring. Generally, preference is given to alkyl or alkenyl groups over alkynyl groups as $R^1$.

The alkyl, alkenyl or alkynyl groups as $R^1$ may be interrupted by one or more, such as one, two, three or four, heteroatoms or heterogroups selected from O, S and $NR^5$, with $R^5$ being selected from —H or —$C_{1-4}$ alkyl. However, preferred are groups as $R^1$ which do not contain such heteroatoms or heterogroups.

Moreover, the alkyl, alkenyl or alkynyl groups as $R^1$ may carry one or more, such as one, two or three, substituents. However, preference is given to unsubstituted groups. Suitable substituents may be independently selected from aryl (such as $C_{6-14}$ aryl or, e.g., phenyl), —OH, $C_{1-4}$ alkoxy, halogen, nitro, amido, amino or —$COOR^6$. In this context, the alkoxy group is preferably methoxy or ethoxy. "Halogen" is typically a fluorine, chlorine, bromine or iodine atom. "Amido" refers to a group —$C(O)NR^7R^8$. "Amino" refers to a group —$NR^7R^8$. $R^6$ may be —H, $C_{1-4}$ alkyl, phenyl or $C_{7-10}$ aralkyl. $R^7$ and $R^8$ are independently selected from —H, $C_{1-4}$ alkyl, phenyl and $C_{7-10}$ alkaryl. Among these substituents, preference is given to —OH, halogen, —COOH, amino or amido.

If $R^1$ is a phenyl or aralkyl group, optional substituent(s) may be present in any position (o-, m- or p-) relative to the bond which attaches the phenyl or aryl ring to the remaining molecule. One, two or three identical or different substituent(s) may optionally be present on an aromatic ring of $R^1$, with preference given to cases where the aromatic ring is monosubstituted or unsubstituted.

Optional substituent(s) present on the phenyl or aralkyl group can be independently selected from —OH, $C_{1-4}$ alkyl, $C_{1-4}$ alkoxy, halogen, nitro, amido, amino or —$COOR^6$. In this context, the alkyl group is preferably methyl or ethyl, and the alkoxy group is preferably methoxy or ethoxy. "Halogen" is typically a fluorine, chlorine, bromine or iodine atom. "Amido" refers to a group —$C(O)NR^7R^8$. "Amino" refers to a group —$NR^7R^8$. $R^6$ may be —H, $C_{1-4}$ alkyl, phenyl or $C_{7-10}$ aralkyl. $R^7$ and $R^8$ are independently selected from —H, $C_{1-4}$ alkyl, phenyl and $C_{7-10}$ alkaryl.

Aralkyl groups (i.e., $C_{7-12}$ aralkyl groups) as an option for $R^1$ may, in one aspect of all embodiments provided herein, be understood and denoted as —$C_{1-6}$-alkylene-phenyl, wherein the divalent alkylene group with 1 to 6 carbon atoms may be linear or branched. In this context, particularly preferred aralkyl groups have alkylene groups with up to 4, such as 1 or 2, carbon atoms.

Preferred among the groups $R^1$ containing an aromatic ring is an optionally substituted phenyl group or an optionally substituted benzyl group, with particular preference on the optionally substituted phenyl group.

If $R^1$ is a phenyl or aralkyl group, particularly preferred embodiments are those wherein these groups are unsubstituted or substituted by a $C_{1-4}$ alkoxy group, such as a para-$C_{1-4}$ alkoxy group, and in particular a p-methoxy-phenyl or p-ethoxy-phenyl group.

Most preferable are cases wherein $R^1$ is $C_{4-14}$ alkyl, $C_{4-14}$ alkenyl, $C_{4-14}$ alkynyl or optionally substituted phenyl, and most preferably $R^1$ is $C_{7-12}$ alkyl, $C_{7-12}$ alkenyl, $C_{7-12}$ alkynyl or $C_{1-4}$ alkoxy-phenyl.

In the compounds of formula (I), $R^2$ is H.

In the compounds of formula (I), $R^3$ is —H, $C_{1-12}$ alkyl, $C_{2-12}$ alkenyl, $C_{2-12}$ alkynyl, phenyl or $C_{7-12}$ aralkyl, or $R^3$ and $R^4$ together form a 5- or 6-membered carbocyclic ring. An alkyl, alkenyl or alkynyl group as $R^3$ may be substituted. Independently, an alkyl, alkenyl or alkynyl group as $R^3$ may be interrupted by one or more heteroatoms or heterogroups selected from O, S or $NR^5$, with $R^5$ being selected from —H or —$C_{1-4}$ alkyl. Both a phenyl group or an aralkyl group as $R^3$ may be substituted on the aromatic ring.

Alkyl groups as $R^3$ preferably have 10 or less or 8 or less carbon atoms, more preferably 6 or less or 5 or less carbon atoms. Often, they have two or more carbon atoms. Particularly preferred groups are methyl, ethyl, propyl, butyl or pentyl groups. The alkyl groups may be linear or branched, with linear groups being preferred.

Alkenyl groups as $R^3$ preferably have 10 or less or 8 or less carbon atoms, more preferably 6 or less or 5 or less carbon atoms. Frequently, they have three or more carbon atoms. Particularly preferred groups are propenyl, butenyl or pentenyl groups. The alkenyl groups may be linear or branched, with linear groups being preferred. They have one or more, such as two, double bonds, and preferably have one double bond. A preferred position of a double bond is the omega-position of the alkenyl chain relative to the lactone ring.

Alkynyl groups as $R^3$ preferably have 10 or less or 8 or less carbon atoms, more preferably 6 or less or 5 or less carbon atoms. Frequently, they have three or more carbon atoms. Particularly preferred groups are propynyl, butynyl or pentynyl groups. The alkynyl groups may be linear or branched, with linear groups being preferred. They have one or more, such as two, triple bonds, and preferably have one triple bond. A preferred position of a triple bond is the omega-position of the alkynyl chain relative to the lactone ring.

The alkyl, alkenyl or alkynyl groups as $R^3$ may be interrupted by one or more, such as one, two or three, heteroatoms or heterogroups selected from O, S or $NR^5$, with $R^5$ being selected from —H or —$C_{1-4}$ alkyl. However, preferred are groups as $R^3$ which do not contain such heteroatoms or heterogroups.

Moreover, the alkyl, alkenyl or alkynyl groups as $R^3$ may carry one or more, such as one, two or three, substituents. However, preference is given to unsubstituted groups. Suitable substituents may be independently selected from aryl (such as $C_{6-14}$ aryl or, e.g., phenyl), —OH, $C_{1-4}$ alkoxy, halogen, nitro, amido, amino or —$COOR^6$. In this context, the alkoxy group is preferably methoxy or ethoxy. "Halogen" is typically a fluorine, chlorine, bromine or iodine atom. "Amido" refers to a group —$C(O)NR^7R^8$. "Amino" refers to a group —$NR^7R^8$. $R^6$ may be —H, $C_{1-4}$ alkyl, phenyl or $C_{7-10}$ aralkyl. $R^7$ and $R^8$ are independently selected from —H, $C_{1-4}$ alkyl, phenyl and $C_{7-10}$ alkaryl. Among these substituents, preference is given to —OH, halogen, —COOH, amino or amido.

If $R^3$ is a phenyl or aralkyl group, optional substituent(s) may be present in any position (o-, m- or p-) relative to the bond which attaches the phenyl or aryl ring to the remaining molecule. One, two or three identical or different substituent(s) may optionally be present on an aromatic ring of $R^3$, with preference given to cases where the aromatic ring is monosubstituted or unsubstituted, and particular preference to cases where it is unsubstituted.

Suitable substituents on an aromatic ring of $R^3$ can be independently selected from —OH, $C_{1-4}$ alkyl, $C_{1-4}$ alkoxy, halogen, nitro, amido, amino or —COOR$^6$. In this context, the alkyl group is preferably methyl or ethyl, and the alkoxy group is preferably methoxy or ethoxy. "Halogen" is typically a fluorine, chlorine, bromine or iodine atom. "Amido" refers to a group —C(O)NR$^7$R$^8$.

"Amino" refers to a group —NR$^7$R$^8$. $R^6$ can be chosen from —H, $C_{14}$ alkyl, phenyl or $C_{7-10}$ aralkyl. $R^7$ and $R^8$ are independently selected from —H, $C_{1-4}$ alkyl, phenyl and $C_{7-10}$ alkaryl.

If $R^3$ represents an aralkyl group, the aralkyl group (i.e., $C_{7-12}$ aralkyl group) may, in one aspect of all embodiments provided herein, be understood and denoted as —$C_{1-6}$-alkylene-phenyl, wherein the divalent alkylene group with 1 to 6 carbon atoms may be linear or branched, with linear groups being preferred. Preferably, alkylene groups in the aralkyl groups of $R^3$ have up to 4, such as 1, 2 or 3 carbon atoms.

Preferred among the above groups containing an aromatic ring as $R^3$ are a phenyl or $C_{7-10}$ aralkyl group, which may also be denoted as —$C_{1-4}$ alkylene-phenyl. More preferred is a $C_{7-8}$ aralkyl group. General preference is given to the aralkyl group over the phenyl group.

Most preferable are cases wherein $R^3$ is $C_{1-6}$ alkyl, $C_{2-6}$ alkenyl, $C_{2-6}$ alkynyl, $C_{7-10}$ aralkyl, or where $R^3$ and $R^4$ form a ring together with the carbon atom to which they are attached, such as, e.g., a saturated 6-membered carbocyclic ring.

In the compounds of formula (I), $R^4$ is H or $C_{1-8}$ alkyl, or $R^3$ and $R^4$ together form a 5- or 6-membered carbocyclic ring. An alkyl group as $R^4$ may be substituted. Independently, an alkyl group as $R^4$ may be interrupted by one or more heteroatoms or heterogroups selected from O, S or NR$^5$, with $R^5$ being selected from —H or —$C_{1-4}$ alkyl.

Alkyl groups as $R^4$ preferably have 6 or less or 5 or less carbon atoms, and most preferably 4 or less carbon atoms. Particularly preferred alkyl groups are methyl, ethyl, propyl or butyl groups. The alkyl groups may be linear or branched, with linear groups being preferred.

The alkyl group as $R^4$ may be interrupted by one or more, such as one, two or three, heteroatoms or heterogroups selected from O, S or NR$^5$, with $R^5$ being selected from —H or —$C_{1-4}$ alkyl. However, preferred are groups as $R^4$ which do not contain such heteroatoms or heterogroups.

Moreover, the alkyl group as $R^4$ may carry one or more, such as one, two or three, substituents.

However, preference is given to an unsubstituted group. Suitable substituents may be independently selected from aryl (such as $C_{6-14}$ aryl or, e.g., phenyl), —OH, $C_{1-4}$ alkoxy, halogen, nitro, amido, amino or —COOR$^6$. In this context, the alkoxy group is preferably methoxy or ethoxy. "Halogen" is typically a fluorine, chlorine, bromine or iodine atom. "Amido" refers to a group —C(O)NR$^7$R$^8$. "Amino" refers to a group —NR$^7$R$^8$. $R^6$ may be —H, $C_{1-4}$ alkyl, phenyl or $C_{7-10}$ aralkyl. $R^7$ and $R^8$ are independently selected from —H, $C_{1-4}$ alkyl, phenyl and $C_{7-10}$ alkaryl. Among these substituents, preference is given to —OH, halogen, —COOH, amino or amido.

Most preferably, $R^4$ is H or $C_1$-$C_4$ alkyl, particularly preferably H.

In another strongly preferred embodiment, $R^3$ and $R^4$ are taken together to form a 5- or 6-membered carbocyclic ring which is typically saturated, preferably a 6-membered saturated carbocyclic ring.

The scope of the invention embraces all pharmaceutically acceptable salt forms of the compounds of formula (I) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, sulfate salts, nitrate salts, phosphate salts, carbonate salts, hydrogencarbonate salts or perchlorate salts; organic acid salts such as acetate, propionate, lactate, maleate, fumarate, tararic acid salt, malate, citrate or ascorbate salts; sulfonate salts such as methanesulfonate, benzenesulfonate, or p-toluenesulfonate salts; and acidic amino acid salts such as aspartate or glutamate salts.

Moreover, the scope of the invention embraces solid forms of the compounds of formula (I) in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

The compounds of the present invention, i.e. the beta-lactones as described herein are particularly useful as pharmaceuticals/inhibitors of bacterial or protozoal virulence, in particular bacterial virulence. These compounds may also be adminstered in form of pharmceutically acceptable prodrugs. Pharmaceutically acceptable prodrugs of the herein described beta-lactone compounds that can be used in the present invention are derivatives which have chemically or metabolically cleavable groups and become, by solvolysis or under physiological conditions, the compounds of the invention which are pharmaceutically active in vivo. Prodrugs of compounds that can be used in the present invention may be formed in a conventional manner with a functional group of the compounds such as with an amino or hydroxy group, e.g. as carbamates esters or glycosides. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985).

The compounds of the present invention, i.e. the beta-lactones of formula (I) and derivatives thereof can be readily synthesized by a chemist experienced in the field of organic synthesis. For example, a one-pot reaction may be used between suitably functionalized compounds, such as $R^3$—C (O)H, and S-phenyl thioates (R. L. Danheiser et al., J. Org. Chem. 1991, 56, 1176; R. L. Danheiser et al., J. Org. Chem. 1991, 56, 1176). This method is illustrated in FIG. 1, using 5-hexynal as an example for the component eventually forming a part of the lactone ring and the $R^3$-residue (in the figure, LDA is lithium diisopropylamide). Of course, alternative methods will be available to the skilled person to arrive at the respective compounds.

Some preferred compounds of formula (I) which combine preferred embodiments as defined above are:

those wherein $R^1$ is $C_{4-14}$ alkyl, $C_{4-14}$ alkenyl, $C_{4-14}$ alkynyl or optionally substituted phenyl, $R^3$ is $C_{1-6}$ alkyl, $C_{2-6}$ alkenyl, $C_{2-6}$ alkynyl or $C_{7-10}$ aralkyl and $R^4$ is H or $C_{1-4}$ alkyl;

those wherein $R^1$ is $C_{4-14}$ alkyl, $C_{4-14}$ alkenyl or optionally substituted phenyl, $R^3$ is $C_{1-6}$ alkyl, $C_{2-6}$ alkenyl, $C_{2-6}$ alkynyl or $C_{7-10}$ aralkyl and $R^4$ is H or $C_{1-4}$ alkyl;

those wherein $R^1$ is $C_{4-14}$ alkyl, $C_{4-14}$ alkenyl or optionally substituted phenyl, $R^3$ is $C_{7-10}$ aralkyl and $R^4$ is H;

those wherein $R^1$ is $C_{4-14}$ alkyl, $C_{4-14}$ alkenyl, $C_{4-14}$ alkynyl or optionally substituted phenyl, and $R^3$ and $R^4$ are taken together to form a 5- or 6-membered carbocyclic ring;

those wherein $R^1$ is $C_{4-14}$ alkyl, $C_{4-14}$ alkenyl or optionally substituted phenyl, and $R^3$ and $R^4$ are taken together to form a 5- or 6-membered carbocyclic ring;

those wherein $R^1$ is $C_{7-14}$ alkyl, $C_{7-14}$ alkenyl, $C_{7-14}$ alkynyl or optionally substituted phenyl, $R^3$ is $C_{1-6}$ alkyl, $C_{2-6}$ alkenyl, $C_{2-6}$ alkynyl or $C_{7-10}$ aralkyl and $R^4$ is H or $C_{1-4}$ alkyl;

those wherein $R^1$ is $C_{7-14}$ alkyl, $C_{7-14}$ alkenyl or optionally substituted phenyl, $R^3$ is $C_{1-6}$ alkyl, $C_{2-6}$ alkenyl, $C_{2-6}$ alkynyl or $C_{7-10}$ aralkyl and $R^4$ is H or $C_{1-4}$ alkyl;

those wherein $R^1$ is $C_{7-14}$ alkyl, $C_{7-14}$ alkenyl or optionally substituted phenyl, $R^3$ is $C_{7-10}$ aralkyl and $R^4$ is H;

those wherein $R^1$ is $C_{7-14}$ alkyl, $C_{7-14}$ alkenyl, $C_{7-14}$ alkynyl or optionally substituted phenyl, and $R^3$ and $R^4$ are taken together to form a 5- or 6-membered carbocyclic ring;

those wherein $R^1$ is $C_{7-14}$ alkyl, $C_{7-14}$ alkenyl or optionally substituted phenyl, and $R^3$ and $R^4$ are taken together to form a 5- or 6-membered carbocyclic ring;

those wherein $R^1$ is $C_{8-12}$ alkyl, $C_{8-12}$ alkenyl, $C_{8-12}$ alkynyl or optionally substituted phenyl, $R^3$ is $C_{1-6}$ alkyl, $C_{2-6}$ alkenyl, $C_{2-6}$ alkynyl or $C_{7-10}$ aralkyl and $R^4$ is H or $C_{1-4}$ alkyl;

those wherein $R^1$ is $C_{8-12}$ alkyl, $C_{8-12}$ alkenyl or optionally substituted phenyl, $R^3$ is $C_{1-6}$ alkyl, $C_{2-6}$ alkenyl, $C_{2-6}$ alkynyl or $C_{7-10}$ aralkyl and $R^4$ is H or $C_{1-4}$ alkyl;

those wherein $R^1$ is $C_{8-12}$ alkyl, $C_{8-12}$ alkenyl or optionally substituted phenyl, $R^3$ is $C_{7-10}$ aralkyl and $R^4$ is H;

those wherein $R^1$ is $C_{8-12}$ alkyl, $C_{8-12}$ alkenyl, $C_{8-12}$ alkynyl or optionally substituted phenyl, and $R^3$ and $R^4$ are taken together to form a 5- or 6-membered carbocyclic ring;

those wherein $R^1$ is $C_{8-12}$ alkyl, $C_{8-12}$ alkenyl or optionally substituted phenyl, and $R^3$ and $R^4$ are taken together to form a 5- or 6-membered carbocyclic ring;

or compounds U1, D3, E2, G2 and S1 as identified below or in FIG. 2B, wherein the double and/or triple bonds which are indicated at the terminal of the substituents $R^1$ and $R^3$ may be replaced by single bonds, where applicable (i.e., the invention also comprises a compound having one of the formulae U1, D3, E2, G2 or S1 as shown below or in FIG. 2B, wherein the terminal double bond, if said double bond is present, and/or the terminal triple bond, if said triple bond is present, is/are replaced by single bond/single bonds).

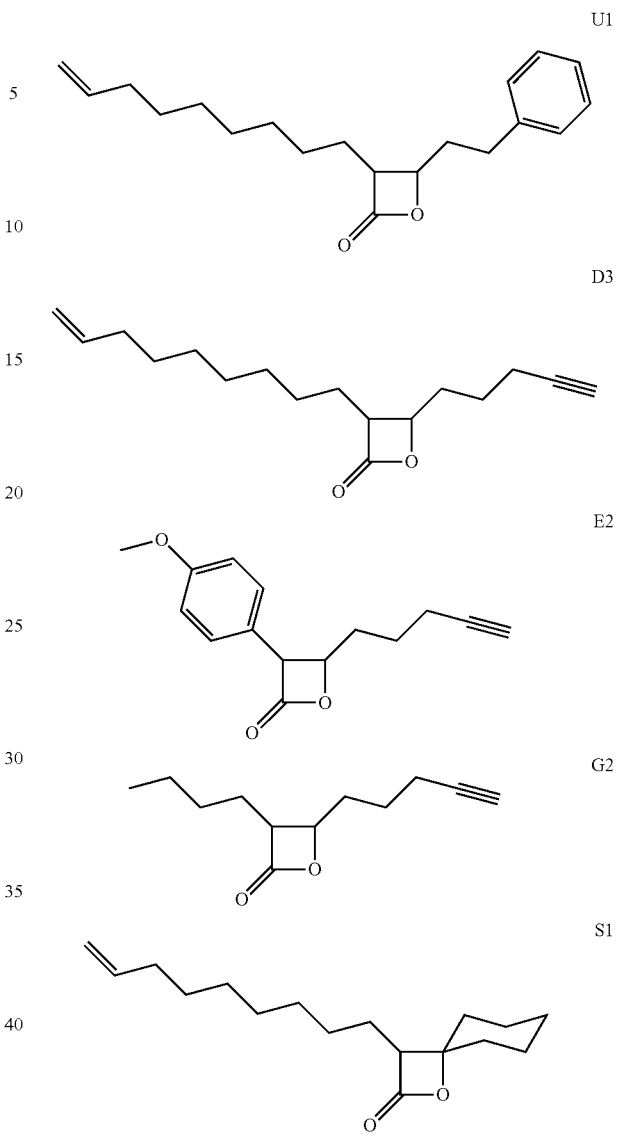

In a particularly preferred embodiment, the compound of formula (I) is a compound having formula U1 as shown below or a compound of formula U1, wherein the terminal carbon-carbon double bond is replaced by a carbon-carbon single bond.

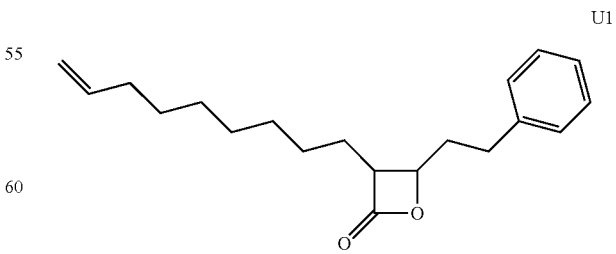

Figure 2A:
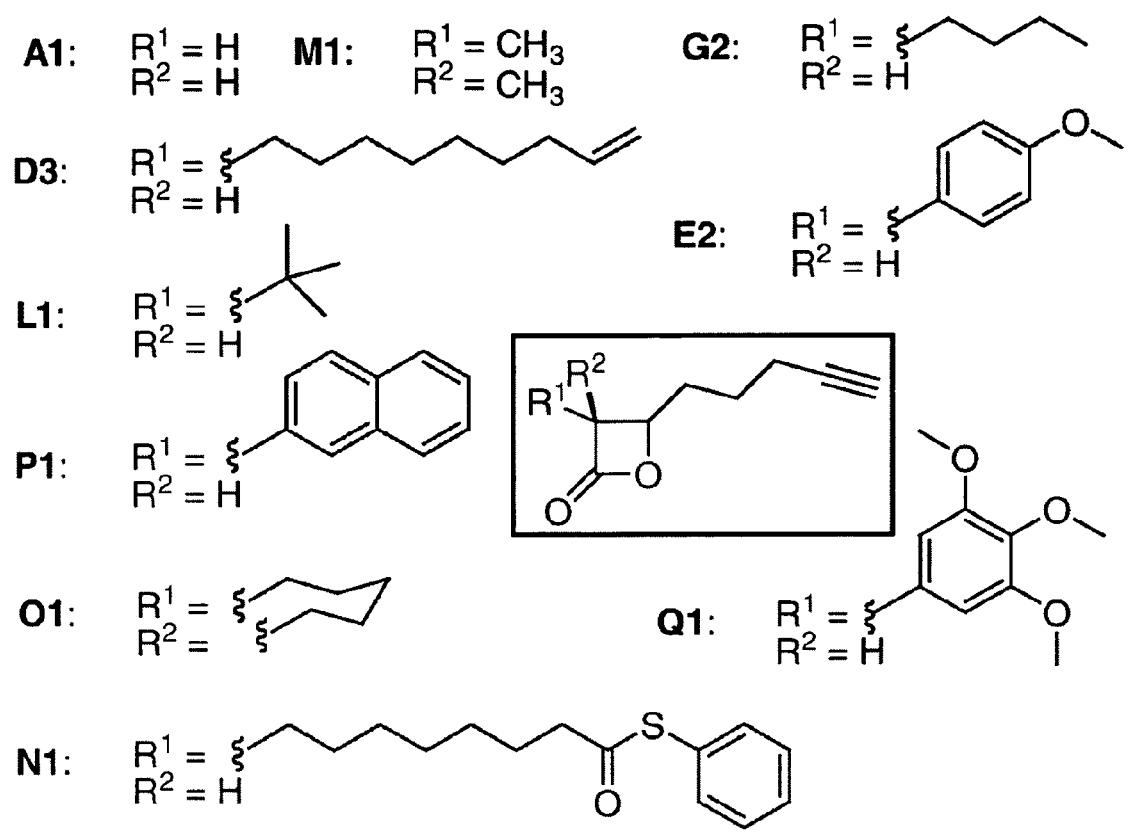
Figure 2B:
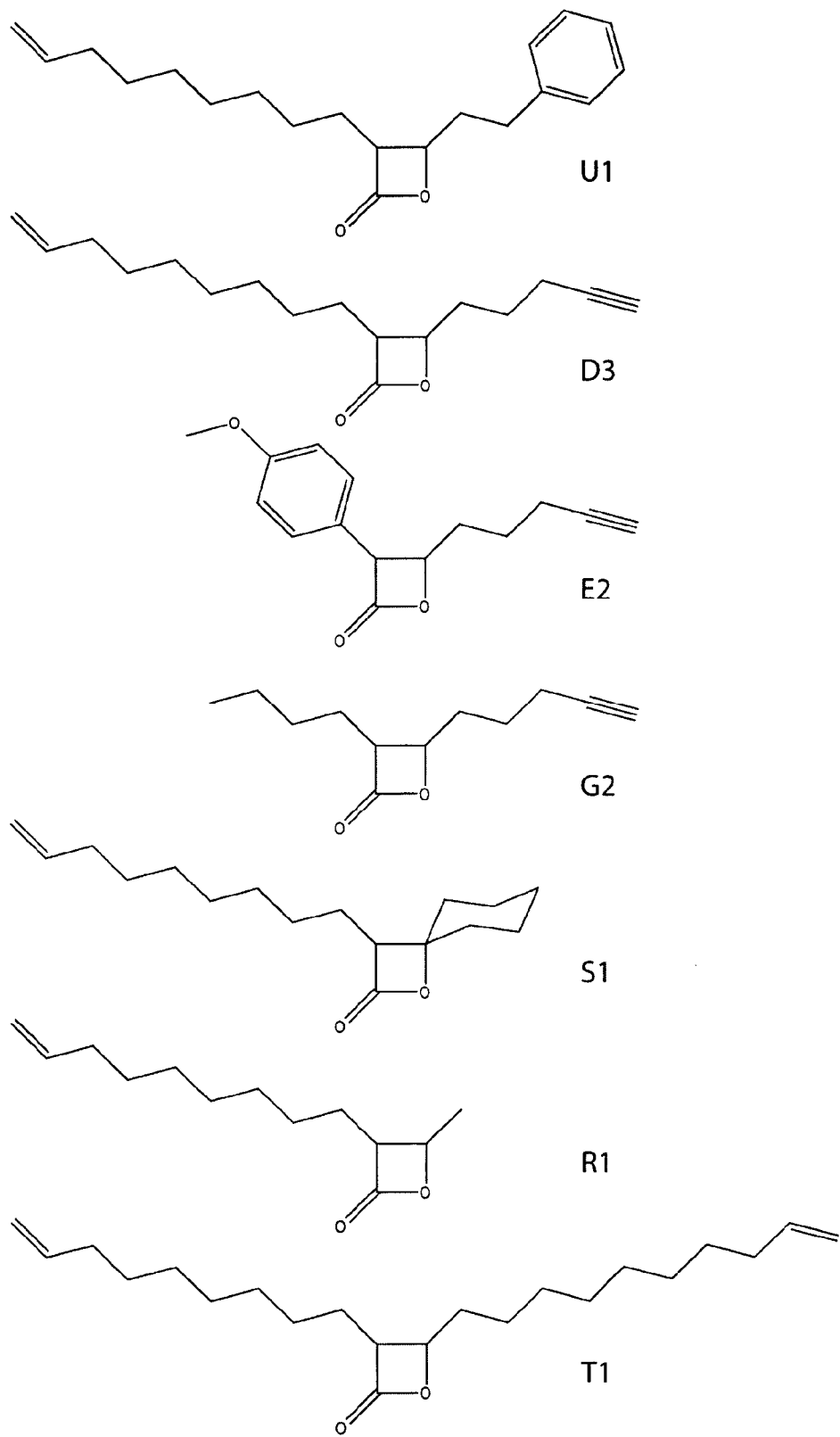

As an exceptional case, the beta-lactone compound N1 as shown in FIG. 2A is useful in the treatment, prevention and/or amelioration of bacterial infections with certain Gram-positive bacteria, such as, e.g., *Listeria* spp. and in particular *Listeria monocytogenes*, as demonstrated in appended Example 8.

In one embodiment of the present invention, a compound of the general formula (I)

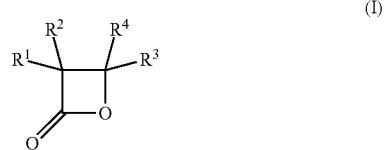

(I)

is provided, wherein $R^1$ is $C_{7-14}$ alkyl, $C_{7-14}$ alkenyl or $C_{7-14}$ alkynyl; $R^2$ is H; $R^3$ is H, $C_{1-6}$ alkyl, $C_{2-6}$ alkenyl, $C_{2-6}$ alkynyl, or $C_{7-10}$ aralkyl; and $R^4$ is H or $C_1$-$C_8$ alkyl; or $R^3$ and $R^4$ combine to form a 5- or 6-membered carbocyclic ring. In a preferred aspect of this embodiment, the compound is a compound having one of the formulae U1, D3, E2, G2 or S1 as shown herein above or in FIG. 2B or a compound of one of the formulae U1, D3, E2, G2 or S1 as shown herein above or in FIG. 2B, wherein the terminal double bond, if said double bond is present, and/or the terminal triple bond, if said triple bond is present, is/are replaced by single bond/single bonds. In a more preferred aspect of this embodiment, the compound is a compound having formula U1 as shown herein above or in FIG. 2B or a compound of formula U1, wherein the terminal carbon-carbon double bond is replaced by a carbon-carbon single bond.

According to the present invention, the compound of formula (I) is used as an antibacterial agent or an antiprotozoal agent (in particular, an antibacterial agent) and may be used for the treatment, amelioration or prevention of an infection, such as, e.g., a bacterial infection or a protozoan infection (in particular, a bacterial infection). The compound of formula (I) may also be used for the preparation of a pharmaceutical composition for the treatment, amelioration or prevention of an infection, such as, e.g., a bacterial infection or a protozoan infection (in particular, a bacterial infection). A compound of formula (I) for the treatment of bacterial infections has not been described in the prior art.

As mentioned herein above, the identification of compounds which can be used as antibacterial or antiprotozoal agents is certainly not a trivial task. In the present invention it was surprisingly found that the compounds described herein efficiently inhibit the activity of bacteria. This is also demonstrated in appended Examples 2 to 4 which show that the haemolytic and proteolytic activity of the bacterium *Staphylococcus aureus* is strongly reduced by the inventive compounds. It is also envisaged that the compounds and compositions described herein be used to efficiently inhibit the activity of protozoa as detailed below.

It is known in the art that bacteria may develop multiple resistancies against known antibiotics. For example, specific multiresistant Staphylococcus aureus strains are resistant to all known beta-lactam antibiotics (such as methicillin, oxacillin, flucloxacillin) and are accordingly called "methicillin-resistant Staphylococcus aureus (MRSA)-strains". Only few antibiotics (inter alia, glycopeptides, such as vancomycin or teicoplanin) can be used to treat infections which are, inter alia, caused by MRSA strains. However, some MRSA strains have become resistant to vancomycin, too (vancomycin intermediate Staphylococcus aureus (VISA) and vancomycin resistant Staphylococcus aureus (VRSA) strains). Also vancomycin resistant Enterococci (VRE), penicillin resistant pneumococci and multiple resistant gram negative bacteria are known in the art. In the context of the present invention, the term "Enterococcus" refers to a genus of Gram-positive, lactic acid bacteria of the phylum Firmicutes. The term "pneumococci" used herein refers to bacteria belonging to the Gram-positive species *Streptococcus pneumoniae*.

One advantage of the present compounds is the fact that they can be used for treating, preventing or ameliorating bacterial infections caused by said multi-resistant bacteria. Tests with MRSA strains and very aggressive *S. aureus* strains showed that the inventive beta-lactone compounds are particularly suited to reduce the virulence of these strains. The inventive compounds may also be used in cotherapy comprising the administration of antibiotics thus possibly enhancing the effect of antibiotics known in the art.

Some bacteria are also intrinsically resistant (i.e. resistance is not acquired) to antibiotics. For example, Gram-positive *Leuconostoc* and *Pediococcus* species and most *Lactobacillus* species as well as most gram-negative bacteria are intrinsically resistant to vancomycin. Accordingly, the compound of the present invention may be particularly useful for the treatment of bacterial infections which are, inter alia, caused by intrinsically resistant bacteria.

It is known that antibiotics, in particular penicillin and derivatives thereof, may elicit allergic reactions in about 1 out of 7000 patients. The compound of the present invention may thus be advantageous for the treatment of bacterial infections, whereby the subjects to be treated are allergic to antibiotics known in the art.

In the prior art antibiotics have been used to target the viability of bacteria, for example, by inhibiting cell wall synthesis. As many bacteria have become resistant to known antibiotics targeting the viability it is highly desirable to prevent the formation of resistant strains. Without being bound by theory, the compound of the present invention may act as an antibacterial agent by binding to and thereby inhibiting the bacterial protease ClpP which is described herein below in more detail. It is known in the art that bacterial virulence factors such as ClpP are not essential for viability of the bacteria but are indispensable for bacterial pathogenesis. In contrast to the antibiotics known in the art the compound employed herein thus does not target bacterial viability but targets virulence factors essential for infection, which are required to cause host damage and disease. Accordingly, one advantage of the present compound is the fact that it may exert less selective pressure on the bacteria which may result in decreased resistance.

As a further advantageous property, the compound of the invention may be used to treat bacterial infections caused by a broad range of gram-positive and gram-negative bacteria.

As a further advantageous property, the present compound is not only useful for the treatment of bacterial or protozoan infections but it is also useful for the elimination or destruction of biofilms. As described herein below in more detail, a biofilm is a complex aggregation (i.e. community) of microorganisms (e.g. bacterial, fungal, algal) enveloped by extracellular biopolymers produced by microbial cells. Biofilms are formed, for example, on surfaces of technical devices such as surgical instruments. The compounds of the present invention are particularly advantageous when such biofilms are to be destroyed but the application of heat, antibiotics known in the art or disinfectants is to be avoided.

In one embodiment, the present invention relates to a compound as described herein above for the treatment, amelioration or prevention of a disease induced by or related to a bacterial or a protozoan infection, in particular a disease induced by or related to a bacterial infection. The terms "bacterial infection" and "protozoan infection" used in the context of the present invention mean transfer, lodgement and penetration of bacteria or protozoa, respectively, in a macroorganism such as a human, an animal or a plant and propagation of the bacteria or the protozoa in said macroorganism. The meaning of the term "infection" may also be deduced from standard textbooks, such as Pschyrembel (Klinisches Worterbuch, 257. edition, 1994). A bacterial infection which causes pain or suffering in a subject may generally be considered as "bacterial infectious disease". The treatment, amelioration or prevention of a bacterial infection, as referred to herein, includes the treatment, amelioration or prevention of a disease induced by or related to a bacterial infection. The compound may also be used for the treatment, amelioration and prevention of a bacterial infection even if the infection does not cause pain or suffering in a subject. Accordingly, the treatment, amelioration or prevention of a protozoan infection, as referred to herein, includes the treatment, amelioration or prevention of a disease induced by or related to a protozoan infection A bacterial infection to be treated in accordance with the present invention may be caused by one ore more bacterial species. The term "bacteria" used herein means prokaryotic, unicellular organisms and refers to the evolutionary damains "Bacteria" and "Archeae". Exemplary phyla of bacteria are Acidobacteria, Actinobacteria, Aquificae, Bacteroidetes, Chlamydiae, Chlorobi, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogae, and Verrucomicrobia.

It is envisaged herein that the bacterial infection is caused by Gram-positive and/or Gram-negative bacteria, in particular pathogenic Gram-positive and/or Gram-negative bacteria, and especially pathogenic Gram-positive bacteria. The terms "Gram-positive" and "Gram-negative" bacteria are well known in the art.

Generally, Gram-positive bacteria are bacteria that appear violet (or blue or purple) after Gram-staining by retaining a crystal violet dye in their cell wall during the staining process. The cell wall of Gram-positive bacteria comprises a thick peptidoglycan layer outside their cytoplasmic membrane and has no additional outer membrane. In contrast, Gram-negative bacteria appear pink (or red) after Gram-staining. Their cell wall comprises a thin peptidoglycan layer and an outer membrane.

Gram-positive bacteria comprise, with very few exceptions, the groups of Firmicutes and Actinobacteria (Actinomycetes), while all Proteobacteria species are Gram-negative. Also the terms "Firmicutes", "Actinobacteria" and "Proteobacteria" are well known in the art. As also documented in the appended examples, beta-lactones are particularly useful in the inhibition of virulence of Gram-positive bacteria. Accordingly, the present invention relates in one embodiment to the medical use of beta-lactones in the suppression, amelioration and/or treatment of bacterial infections. Particular preferred beta-lactones for such a medical use (but also for the anti-bacterial cleaning of devices and appartuses) are the beta-lactone compounds as decribed herein, i.e. the beta-lactone compounds as provided by formula (I).

Gram-positive Firmicutes comprise for example the "Bacilli", including but not limited to the genera *Bacillus, Listeria, Staphylococcus, Enterococcus, Lactobacillus, Lactococcus, Leuconostoc, Pediococcus*, and *Streptococcus*, "Clostridia" (e.g. the genera *Acetobacterium, Clostridium, Eubacterium, Heliobacterium, Heliospirillum, Pectinatus*, and *Sporomusa*) and Mollicutes (e.g. genera *Mycoplasma, Spiroplasma, Ureaplasma*, and *Erysipelothrix*). Actinobacteria, include for example the *Actinomyces, Arthrobacter, Corynebacterium, Frankia, Micrococcus, Micromonospora, Nocardia, Propionibacterium, Streptomyces* genera and *Mycobacterium*. Mycobacteria-induced diseases to be treated in accordance with the present invention include, inter alia, tuberculosis, leprosy, tropical skin ulcer, ulceration, abscess, pulmonary disease, granulomatous (skin) disease, opportunistic infections with non-tuberculous mycobacteria as well as diseases elicited by atypical mycobacteria such as *M. avium* including pulmonary disease, lymphadenitis, cutaneous and disseminated diseases, e.g. in immunocompromised patients. The use is not restricted to mycobacteria-induced diseases in humans, but comprises also the use of the present invention in animal diseases, like bovine tuberculosis. Furthermore, as mentioned herein, the compounds of the present invention are useful in the medical intervention of bacterial infections in general and the herein described beta-lactone compounds are particularly useful in the medical intervention of infections with Gram-positive bacteria, in particular Firmicutes and Actinobacteria, like *Staphylococcus spec* or *Listeria spec.*

Non-limiting examples of bacterial species which belong to the groups of Firmicutes and Actinobacteria are *Listeria monocytogenes, Listeria welshimeri, Staphylococcus aureus, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Bacillus licheniformis, Bacillus subtilis, Bacillus anthracia, Bacillus cereus, Bacillus thuringiensis, Bacillus larvae, Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum, Mycobacterium canettii, Mycobacterium intracellulare, Mycobacterium simiae, Mycobacterium szulgai, Mycobacterium xenopi, Mycobacterium fortuitum, Mycobacterium chelonei, Mycobacterium marinum, Nocardia asteroides*, and *Rhodococcus equi*.

Exemplary Gram-negative bacteria belong, inter alia, to the genera *Escherichia, Salmonella, Pseudomonas, Moraxella, Helicobacter, Stenotrophomonas, Bdellovibrio, Legionella, Vibrio, Neisseria, Hemophilus, Chlamydia, Klebsiella, Legionella, Proteus, Enterobacter, Serratia*. Further Gram-negative bacteria are, inter alia, acetic acid bacteria. Non-limiting examples of Gram-negative bacteria species are *Neisseria gonorrhoeae, Neisseria meningitidis, Moraxella catarrhalis, Haemophilus influenzae, Klebsiella pneumoniae, Legionella pneumophila, Pseudomonas aeruginosa, Pseudomonas putida, Escherichia coli, Proteus mirabilis, Enterobacter cloaceae, Serratia marcescens, Helicobacter pylori, Salmonella enteritidis*, and *Salmonella typhi*. It is envisaged that the compounds of the present invention and as described herein (beta-lactones and derivatives thereof) are also useful in the inhibition of virulence in Gram-negative bacteria.

Without being bound by theory, it is believed that one mechanism by which the compounds as described herein, i.e. beta-lactones of formula (I) and derivatives thereof may exert its antibacterial or antiprotozoal effect/inhibition of virulence, may be its specific binding to and thereby inhibiting the protease ClpP (i.e., with regard to bacteria, the bacterial protease ClpP).

It is demonstrated in the appended examples, particularly in the appended Examples 6 and 7, that beta-lactones according to the present invention specifically bind to bacterial virulence factors such as the caseinolytic protease ClpP and proline iminopeptidase (PIP) in vitro and in vivo. Furthermore, appended Examples 2 to 4 demonstrate that the beta-lactone compounds of the present invention can inhibit haemolysis and proteolysis abilities of Gram-positive bacteria, particularly of *Staphylococcus aureus*. Appended Example 6 and FIGS. 7 to 18 also illustrate a method for the screening and identification of binding targets of specific beta-lactones in various bacterial and non-bacterial proteomes. In addition to the inhibition of haemolysins and proteases, the inventive beta-lactone compounds may also, without being bound by theory, inhibit or reduce the activity of further major bacterial virulence factors such as lipases, DNases, and pyrogenic toxin superantigens (PTSA) such as, e.g., toxic shock syndrome toxin 1 (TSST-1) or enterotoxins (e.g., SAB or SAC), in Gram-positive bacteria which is illustrated in the appended Example 8 for *Listeria monocytogenes*. The above mentioned pryogenic toxin superantigens are of major importance for many diseases, such as, e.g., toxic shock syndrome, mastitis or food poisoning.

The beta-lactone compounds of the present invention and derivatives thereof also inhibit the production of the main virulence factors listeriolysin O (LLO) and phosphatidylinositol (PI)-specific phospholipase C (PI-PLC) in *Listeria monocytogenes* as an illustrative example of Gram-positive bacteria, which has been demonstrated in vitro and in vivo, as shown in particular in the appended Example 8. Without being bound by theory, it is believed that the down regulation of these virulence factors, listeriolysin O and PI-PLC, is caused by the inhibition of ClpP by compounds of the present invention. The inventive beta-lactone compounds are thus, inter alia, useful for the inhibition of virulence factors in Gram-positive bacteria and particularly in *Listeria monocytogenes*. This also underlines the suitability of the beta-lactone compounds of the present invention for the treatment, prevention and/or amelioration of bacterial infections caused by extracellular as well as intracellular pathogenic bacteria. As mentioned herein above, such bacterial infections comprise, but are not limited to, infections with *Listeria monocytogenes*, *Listeria welshimeri*, *Staphylococcus aureus*, *Staphylococcus epidermidis*, *Staphylococcus saprophyticus*, *Staphylococcus lugdunensis*, *Staphylococcus schleiferi*, *Staphylococcus caprae*, *Streptococcus pneumoniae*, *Streptococcus viridans*, *Streptococcus pyogenes*, *Streptococcus agalactiae*, *Enterococcus faecalis*, *Enterococcus faecium*, *Bacillus licheniformis*, *Bacillus subtilis*, *Bacillus anthracis*, *Bacillus cereus*, *Bacillus thuringiensis*, *Bacillus larvae*, *Mycobacterium tuberculosis*, *Mycobacterium bovis*, *Mycobacterium leprae*, *Mycobacterium ulcerans*, *Mycobacterium kanasasii*, *Mycobacterium avium*, *Mycobacterium paratuberculosis*, *Mycobacterium scrofulaceam*, *Mycobacterium microti*, *Mycobacterium africanum*, *Mycobacterium canettii*, *Mycobacterium intracellulare*, *Mycobacterium simiae*, *Mycobacterium szulgai*, *Mycobacterium xenopi*, *Mycobacterium fortuitum*, *Mycobacterium chelonei*, *Mycobacterium marinum*, *Nocardia asteroides*, *Rhodococcus equi*, *Neisseria gonorrhoeae*, *Neisseria meningitidis*, *Moraxella catarrhalis*, *Haemophilus influenzae*, *Klebsiella pneumoniae*, *Legionella pneumophila*, *Pseudomonas aeruginosa*, *Pseudomonas putida*, *Escherichia coli*, *Proteus mirabilis*, *Enterobacter cloaceae*, *Serratia marcescens*, *Helicobacter pylori*, *Salmonella enteritidis*, or *Salmonella typhi*, in particular with *Staphylococcus aureus* or *Listeria monocytogenes*.

The term "virulence" used in context of the present invention refers to the ability of microbes, like bacteria, to cause a disease, i.e. to the degree of their pathogenicity. A number of properties of bacteria influence their pathogenicity and virulence, e.g. their ability to adhere to host cells, their ability to form colonies within a host, their ability to invade a host or host cell, their ability to inhibit or evade the immune response of the host, and their ability to produce toxins. In the context of the present invention the term "virulence factor" means intrinsic factors that mediate the virulence of pathogenic bacteria. Such virulence factors are molecules, particularly proteins, produced by the pathogenic bacteria that directly influence the host and allow these bacteria to thrive within a host. Examples of virulence factors include enzymes that inactivate antibiotics, enzymes that disrupt host cells, proteins that influence clot formation, proteins that mediate capsule formation, proteins or protein complexes that mediate attachment to host cells and proteins that mediate evasion of the immune response, e.g. by binding host antibodies. Virulence factors are also involved in biofilm formation.

Known bacterial virulence factors are, for example, the ATP-dependent caseinolytic protease (ClpP) and proline iminopeptidase (PIP). ClpP and ClpX form chambered proteolytic complexes. These proteolytic complexes are essential for the mediation of virulence (Kwon et al., Infection and Immunity 2004, 72, 5646), survival under stress (Frees et al., Mol. Microbiol. 2003, 48, 1565) and biofilm formation (Wang et al., Microbes and Infection 2007, 9, 1376) in several pathogenic bacteria, for example *Staphylococcus aureus*, *Staphylococcus epidermidis* and *Streptococcus pneumoniae*.

It is envisaged herein that the beta-lactones of the present invention and derivatives thereof may bind to the virulence factor ClpP of various bacteria. The inhibition of ClpP by the beta-lactone compounds of the present invention may represent a global approach for the treatment, prevention and/or amelioration of bacterial infections. Without being bound by theory, it is believed that the binding specificity of the inventive compound correlates with the sequence identity of the amino acid sequences of ClpP of said bacteria, i.e. one would expect a higher binding specifity and hence a higher antibacterial activity of the present compound the higher the sequence similarity of the amino acid sequences of ClpP of said bacteria is when compared, for example, to the amino sequence of ClpP from *Staphylococcus aureus* (Sequence 1B). Exemplary nucleic acid and corresponding amino acid sequences of various *Staphylococcus* strains and *Listeria* strains are shown in Sequences 1 to 4. Sequence alignments and determination of sequence identity of exemplary ClpP amino acid sequences are described in Example 5 and are shown in Sequence Alignments 1 to 3.

In accordance with the present invention, the terms "homology" or "percent homology" or "identical" or "percent identity" or "percentage identity" or "sequence identity" in the context of two or more amino acid sequences refer to two or more sequences or subsequences that are the same, or that have a specified percentage of amino acids that are the same (preferably at least 40% identity, more preferably at least 45%, 50%, 55%, 60%, 65%, 70%, 75%, 80%, 85%, 90%, 91%, 92%, 93%, 94%, 95%, 96%, 97% or 98% identity, most preferably at least 99% identity), when compared and aligned for maximum correspondence over a window of comparison, or over a designated region as measured using a sequence comparison algorithm as known in the art, or by manual alignment and visual inspection. Sequences having, for example, 75% to 90% or greater sequence identity may be considered to be substantially identical. Preferably the described identity exists over a region that is at least about 15 to 80 amino acids in length, more preferably, over a region that is at least about 80 to 150 amino acids in length and most preferably, over a region that is at least about 150 to 220 amino acids in length. Those having skill in the art will know how to determine percent identity between/among sequences using algorithms known in the art.

Again, without being bound by theory, the inhibition of bacterial virulence factor production by beta-lactones as described herein may have a direct effect on the pathogenicity for the eukaryotic host. As shown e.g. in Example 8, the intracellular replication of *Listeria monocytogenes* could be significantly reduced in experiments using beta-lactone compounds, whereby *Listeria* replication is believed to be reduced by beta-lactone mediated inhibition of the regulatory protease ClpP. As intracellular pathogens are especially hard to suppress or kill with antibiotics, the significant reduction of intracellular replication, as shown in Example 8, demonstrates the effectiveness of the beta-lactone compounds in the medical intervention of bacterial infections caused by intracellular pathogenic bacteria.

The compounds of the present invention and as described herein (beta-lactones and derivatives thereof) are also useful in the inhibition of virulence in protozoa and are useful in the treatment, prevention and/or amelioration of protozoan infections. Protozoa comprise in particular Plasmodia and, accordingly, protozoan infections, like malaria, plasmodium-related hemoglobinuria, or plasmodium-related diarrhea, may be treated, prevented and/or ameliorated by the administration of beta-lactones, in particular beta-lactones and their derivatives as described herein. A protozoan infection to be treated in accordance with the present invention may be caused by one ore more protozoan species. The term "protozoa" used herein means eukaryotic, unicellular organisms. In particular, said compounds are envisaged to be useful in the treatment, prevention and/or amelioration of infections with Apicomplexa, such as, e.g., *Plasmodium* spp., particularly *Plasmodium falciparum*, *Plasmodium malariae*, *Plasmodium vivax*, *Plasmodium ovale*, or *Plasmodium knowlesi*; *Leishmania* spp., particularly *Leishmania major*, *Leishmania tropica*, *Leishmania aethiopica*, *Leishmania mexicana*, *Leishmania braziliensis*, *Leishmania donovani*, *Leishmania infantum*, or *Leishmania chagasi*; *Trypanosoma* spp., particularly *Trypanosoma brucei*, *Trypanosoma cruzi*, *Trypanosoma simiae*, *Trypanosoma avium*, *Trypanosoma congolense*, *Trypanosoma equinum*, *Trypanosoma equiperdum*, *Trypanosoma evansi*, or *Trypanosoma suis*; *Babesia* spp., particularly *Babesia microti*, or *Babesia bigemina*; or *Toxoplasma*, particularly *Toxoplasma gondii*. Hence, said compounds may be useful in the treatment, prevention and/or amelioration of infectious diseases caused by or related to infections with Apicomplexa (particularly with *Plasmodium* spp., and more particularly with *Plasmodium falciparum*, *Plasmodium malariae*, *Plasmodium vivax* or *Plasmodium ovale*), such as, e.g., malaria, plasmodium-related hemoglobinuria, or plasmodium-related diarrhea Also to be treated, prevented and/or ameliorated in the sense of this invention may be further protozoan infections, like infections with *Leishmania*, e.g. leishmaniasis (e.g., visceral leishmaniasis, kala-azar, cutaneous leishmaniasis) or infections with *Trypanosoma*, like sleeping sickness or Chagas disease. Also infections with Toxoplasma (like *Toxoplasma gondii*) or infections with Babesia, e.g. babesiosis, ma$_y$ be treated with beta-lactones, in particular beta-lactones and their derivatives as described herein.

The beta-lactone compound of the present invention may also be used for cotherapy. For example, one compound of the present invention or two or more compounds of the invention and one or more antibiotics and/or antiseptics may be employed for the treatment, amelioration or prevention of a bacterial infection. A pharmaceutical composition may comprise the compound(s), antibiotic(s) and/or antiseptic(s). Cotherapy may also include the administration of two or more compounds of the present invention in the absence of further antibiotics or antiseptics. It is also envisaged herein that the compound(s), antibiotic(s) and/or antiseptic(s) might be linked, for example, by formation of conjugates. Accordingly, compound, antibiotics and/or antiseptics may be administered to a subject simultaneously. Of course, a pharmaceutical composition may only comprise the compound(s), while the one or more antibiotics and/or antiseptics are comprised in a different pharmaceutical composition. In that case, it may still be possible to administer the inventive compound(s), antibiotics and/or antiseptics simultaneously; however, the compound(s) may then also be administered before and/or after the one or more antibiotics and/or antiseptics. A person skilled in the art knows how to administer, for example, one or more antibiotics, one or more antiseptics and/or one or more inventive compounds in cotherapy.

It is envisaged that one or more of the beta-lactone compounds as described herein may be used in combination with one or more antibiotics and/or one or more antiseptics.

Thereby, the one or more antibiotics include, for example, tetracycline-derived antibiotics such as, e.g., tetracycline, doxycycline, chlortetracycline, clomocycline, demeclocycline, lymecycline, meclocycline, metacycline, minocycline, oxytetracycline, penimepicycline, rolitetracycline, or tigecycline; amphenicol-derived antiobiotics such as, e.g., chloramphenicol, azidamfenicol, thiamphenicol, or florfenicol; macrolide-derived antiobiotics such as, e.g., erythromycin, azithromycin, spiramycin, midecamycin, oleandomycin, roxithromycin, josamycin, troleandomycin, clarithromycin, miocamycin, rokitamycin, dirithromycin, flurithromycin, telithromycin, cethromycin, tulathromycin, carbomycin A, kitasamycin, midecamicine, midecamicine acetate, tylosin (tylocine), or ketolide-derived antiobiotics such as, e.g., telithromycin, or cethromycin; lincosamide-derived antiobiotics such as, e.g., clindamycin, or lincomycin; streptogramin-derived antiobiotics such as, e.g., pristinamycin, or quinupristin/dalfopristin; oxazolidinone-derived antiobiotics such as, e.g., linezolid, or cycloserine; aminoglycoside-derived antiobiotics such as, e.g., streptomycin, neomycin, framycetin, paromomycin, ribostamycin, kanamycin, amikacin, arbekacin, bekanamycin, dibekacin, tobramycin, spectinomycin, hygromycin B, paromomycin, gentamicin, netilmicin, sisomicin, isepamicin, verdamicin, astromicin, rhodostreptomycin, or apramycin; steroid-derived antiobiotics such as, e.g., fusidic acid, or sodium fusidate; glycopeptide-derived antiobiotics such as, e.g., vancomycin, oritavancin, telavancin, teicoplanin, dalbavancin, ramoplanin, bleomycin, or decaplanin; beta-lactam-derived antiobiotics such as, e.g., amoxicillin, ampicillin, pivampicillin, hetacillin, bacampicillin, metampicillin, talampicillin, epicillin, carbenicillin, carindacillin, ticarcillin, temocillin, azlocillin, piperacillin, mezlocillin, mecillinam, pivmecillinam, sulbenicillin, benzylpenicillin, azidocillin, penamecillin, clometocillin, benzathine benzylpenicillin, procaine benzylpenicillin, phenoxymethylpenicillin, propicillin, benzathine, phenoxymethylpenicillin, pheneticillin, oxacillin, cloxacillin, dicloxacillin, flucloxacillin, meticillin, nafcillin, faropenem, biapenem, doripenem, ertapenem, imipenem, meropenem, panipenem, cefacetrile, cefadroxil, cefalexin, cefaloglycin, cefalonium, cefaloridine, cefalotin, cefapirin, cefatrizine, cefazedone, cefazaflur, cefazolin, cefradine, cefroxadine, ceftezole, cefaclor, cefamandole, cefminox, cefonicid, ceforanide, cefotiam, cefprozil, cefbuperazone, cefuroxime, cefuzonam, cefoxitin, cefotetan, cefmetazole, loracarbef, cefcapene, cefdaloxime, cefdinir, cefditoren, cefetamet, cefixime, cefmenoxime, cefodizime, cefoperazone, cefotaxime, cefpimizole, cefpiramide, cefpodoxime, cefsulodin, ceftazidime, cefteram, ceftibuten, ceftiolene, ceftizoxime, ceftriaxone, flomoxef, latamoxef, cefepime, cefozopran, cefpirome, cefquinome, ceftobiprole, aztreonam, tigemonam, sulbactam, tazobactam, clavulanic acid, ampicillin/sulbactam, sultamicillin, piperacillin/tazobactam, co-amoxiclav, amoxicillin/clavulanic acid, or imipenem/cilastatin; sulfonamide-derived antiobiotics such as, e.g., acetazolamide, benzolamide, bumetanide, celecoxib, chlorthalidone, clopamide, dichlorphenamide, dorzolamide, ethoxzolamide, furosemide, hydrochlorothiazide, indapamide, mafenide, mefruside, metolazone, probenecid, sulfacetamide, sulfadiazine, sulfadimethoxine, sulfadoxine, sulfanilamides, sulfamethoxazole, sulfamethoxypyridazine, sulfasalazine, sultiame, sumatriptan, xipamide, zonisamide, sulfaisodimidine, sulfamethizole, sulfadimidine, sulfapyridine, sulfafurazole, sulfathiazole, sulfathiourea, sulfamoxole, sulfadimethoxine, sulfalene, sulfametomidine, sulfametoxydiazine, sulfaperin, sulfamerazine, sulfaphenazole, or sulfamazone; quinolone-derived antiobiotics such as, e.g., cinoxacin, flumequine, nalidixic acid, oxolinic acid, pipemidic acid, piromidic acid, rosoxacin, ciprofloxacin, enoxacin, fleroxacin, lomefloxacin, nadifloxacin, ofloxacin, norfloxacin, pefloxacin, rufloxacin, balofloxacin, grepafloxacin, levofloxacin, pazufloxacin, sparfloxacin, temafloxacin, tosufloxacin, besifloxacin, clinafloxacin, garenoxacin, gemifloxacin, moxifloxacin, gatifloxacin, sitafloxacin, trovafloxacin, alatrofloxacin, prulifloxacin, danofloxacin, difloxacin, enrofloxacin, ibafloxacin, marbofloxacin, orbifloxacin, pradofloxacin, sarafloxacin, ecinofloxacin, or delafloxacin; imidazole-derived antiobiotics such as, e.g., metronidazole; nitrofuran-derived antiobiotics such as, e.g., nitrofurantoin, or nifurtoinol; aminocoumarin-derived antiobiotics such as, e.g., novobiocin, clorobiocin, or coumermycin A1; ansamycin-derived antiobiotics, including rifamycin-derived antiobiotics such as, e.g., rifampicin (rifampin), rifabutin, rifapentine, or rifaximin; and also further antiobiotics such as, e.g., fosfomycin, bacitracin, colistin, polymyxin B, daptomycin, xibornol, clofoctol, methenamine, mandelic acid, nitroxoline, mupirocin, trimethoprim, brodimoprim, iclaprim, tetroxoprim, or sulfametrole; without being limited thereto.

Furthermore, the one or more antiseptics include, for example, acridine-derived antiseptics such as, e.g., ethacridine lactate, aminoacridine, or euflavine; amidine-derived or biguanide-derived antiseptics such as, e.g., dibrompropamidine, chlorhexidine, propamidine, hexamidine, or polihexanide; phenol-derived antiseptics such as, e.g., phenol, hexachlorophene, policresulen, triclosan, chloroxylenol, or biphenylol; nitrofuran-derived antiseptics such as, e.g., nitrofurazone; iodine-based antiseptics such as, e.g., iodine/octylphenoxypolyglycolether, povidone-iodine, or diiodohydroxypropane; quinoline-derived antiseptics such as, e.g., dequalinium, chlorquinaldol, oxyquinoline, or clioquinol; quaternary ammonium-derived antiseptics such as, e.g., benzalkonium, cetrimonium, cetylpyridinium, cetrimide, benzoxonium chloride, or didecyldimethylammonium chloride; mercurial antiseptics such as, e.g., mercuric amidochloride, phenylmercuric borate, mercuric chloride, mercurochrome, thiomersal, or mercuric iodide; silver-based antiseptics such as, e.g., silver nitrate; alcoholic antiseptics such as, e.g., propanol (including isopropanol), or ethanol; and also further antiseptics such as, e.g., potassium permanganate, sodium hypochlorite, hydrogen peroxide, eosin, tosylchloramide sodium, dichlorobenzyl alcohol, ambazone, benzethonium, myristyl-benzalkonium, hexylresorcinol, or acriflavinium chloride; without being limited thereto.

Cotherapy using inventive compound(s), antibiotic(s) and/or antiseptic(s) may result in a synergistic effect, i.e. the agents acting together may create an effect greater than that predicted by knowing only the separate effects of the individual agents. Such a synergistic effect might be particularly advantageous if less amounts of the compound(s), antibiotic(s) and/or antiseptic(s) may then be used. Thus, possible side-effects of the compound(s), antibiotic(s) and/or antiseptic(s) might be diminished or avoided.

In one embodiment, the invention relates to a composition comprising the compound or two or more compounds according to the invention. In addition to the compound of the invention, said composition may comprise diluents, stabilizers and/or carriers. Exemplary diluents are water, phosphate buffered saline and the like. Stabilizers are, for example, pH stabilizers/regulators. Carriers are described herein below in the context of pharmaceutically acceptable carriers. It is envisaged herein that the composition may also comprise detergents. This may be particularly useful when the composition is used for preventing the formation of biofilms or eliminating biofilms on surfaces of a technical device as described herein below. Detergents are a class of molecules whose unique properties enable manipulation (disruption or formation) of hydrophobic-hydrophilic interactions among molecules in a composition. Detergents may be, e.g. Triton X-100®, Triton-X-114®, NP-40®; CHAPS, Tween-20®, Tween-40®, Tween-80®, Octyl Glucoside, Octylthio Glucoside, Brij-35, Brij-58, SDS and the like.

It is envisaged herein that the composition to be prepared in accordance with the present invention or the composition comprising the beta-lactone compound is a pharmaceutical composition.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of a pharmaceutical composition administered to an individual will, inter alia, depend on the nature of the compound. For example, the total pharmaceutically effective amount of a pharmaceutical composition administered parenterally per dose will be in the range of about 1 µg compound/kg/day to 500 mg compound/kg/day, in extreme cases up to 4.0 g compound/kg/day of patient body weight, although, as noted above, this will be subject to therapeutic discretion. Typically, the total pharmaceutically effective amount of a pharmaceutical composition administered parenterally per dose will be in the range of about 1 µg compound/kg/day to 100 mg compound/kg/day of patient body weight. More preferably, this dose is at least 0.01 mg compound/kg/day, and most preferably for humans between about 0.01 and 50 mg compound/kg/day. If given continuously, the pharmaceutical composition is typically administered at a dose rate of about 1 µg/kg/hour to about 10 mg/kg/hour; more preferably, at a a dose rate of about 50 µg/kg/hour to about 3 mg/kg/hour; either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Pharmaceutical compositions of the invention may be administered orally, rectally, parenterally, intracisternally, intravaginally, intraperitoneally, topically (as by powders, ointments, drops or transdermal patch), bucally, or as an oral or nasal spray.

Pharmaceutical compositions of the invention preferably comprise a pharmaceutically acceptable carrier. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release pharmaceutical compositions also include liposomally entrapped compounds. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle. The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection. In a further embodiment, the present invention relates to a method for treating, preventing or ameliorating a bacterial infection comprising the administration of the inventive beta-lactone compound or a derivative thereof to a subject in need of such a treatment, prevention or amelioration.

Exemplary bacterial infections to be treated, prevented or ameliorated in accordance with the present invention are, inter alia, listeriosis, cranial nerve palsy, encephalitis, meningitis, meningoencephalitis, abscesses, endocarditis, pneumonia, cholera, syphilis, anthrax, leprosy, bubanic plaque, sepsis (blood poisoning), septic arthritis, osteitis, inflammation of wounds, furuncles, carbuncles, toxic shock syndrome, Staphylococcal scalded skin snydrome (SSSS), and mastitis.

Abscesses to be treated, prevented or ameliorated in accordance with the invention are, inter alia, abscesses in brains, abscesses in lungs and abscesses in kidneys. Generally, it is envisaged herein that inflammations of organs (such as inflammation of bladder, pneumonia, and the like) may be treated, prevented or ameliorated in accordance with the present invention. The term "osteitis" used in context of the present invention refers to an inflammation of bones or inflammation of bone marrow (commonly known as "osteomyelitis"). "Furuncles" used in context of the present invention are also known as "boils" while the term "carbuncles" used herein means a collection of furuncles. The term "toxic shock syndrome" (TSS) used herein refers to a rare but potentially fatal disease caused by a bacterial toxin. Different bacterial toxins may cause toxic shock syndrome, depending on the situation. Said toxins are particularly produced by Gram-positive bacteria such as *Staphylococcus aureus* and *Streptococcus pyogenes* during bacterial infection. TSS is also referred to as Toxic Shock Like Syndrome (TSLS).

It is also envisaged herein that bacterial or protozoan infections (in particular, bacterial infections) which particularly affect animals can be treated. Non-limiting examples of such bacterial infections are mastitis of dairy cows or laminitis (a disease of digital laminae of feet in horse or cattle). All the terms used herein above reflecting bacterial infections are well known in the art.

Furthermore, it is also envisaged that non-vertebrates, such as insects, etc. are treated with the compounds of this invention. Accordingly, the compounds of the present invention may also be used in the treatment, prevention and/or amelioration of bacterial or protozoan infections (in particular, bacterial infections) of economically relevant insects, like the honey bee. For example, the compounds of the present invention may be used in the treatment, prevention and/or amelioration of infections with *Bacillus larvae*, i.e. foul brood or malignant foolbrood of bees.

As described herein above, the treatment, prevention and/or amelioration of diseases which are induced by or related to bacterial infections is also envisaged herein. Atopic dermatitis may be considered as an exemplary disease which is induced by or related to a bacterial infection. A person skilled in the art will be aware of further diseases induced by or related to a bacterial infection which can be treated in accordance with this invention.

It is to be understood that the term "treatment, prevention and/or amelioration of bacterial infections", as used herein, also comprises the treatment, prevention and/or amelioration of diseases which are induced by or related to bacterial infections, such as, e.g., infections with *Listeria monocytogenes, Listeria welshimeri, Staphylococcus aureus, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Bacillus licheniformis, Bacillus subtilis, Bacillus anthracis, Bacillus cereus, Bacillus thuringiensis, Bacillus larvae, Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum, Mycobacterium canettii, Mycobacterium intracellulare, Mycobacterium simiae, Mycobacterium szulgai, Mycobacterium xenopi, Mycobacterium fortuitum, Mycobacterium chelonei, Mycobacterium marinum, Nocardia asteroides, Rhodococcus equi, Neisseria gonorrhoeae, Neisseria meningitidis, Moraxella catarrhalis, Haemophilus influenzae, Klebsiella pneumoniae, Legionella pneumophila, Pseudomonas aeruginosa, Pseudomonas putida, Escherichia coli, Proteus mirabilis, Enterobacter cloaceae, Serratia marcescens, Helicobacter pylori, Salmonella enteritidis*, or *Salmonella typhi*, and in particular with *Staphylococcus aureus* or *Listeria monocytogenes.*

In a preferred embodiment the subject to be treated is a human. Yet, the subject may be any multicellular organism, for example, protists, fungi .and plants. The meaning of these terms is well known in the art. It is also envisaged that animals are to be treated, whereby the treatment of animals is not limited to vertebrates but also includes non-vertebrates, such as insects, etc. Accordingly, the compounds of the present invention may also be used in the treatment, prevention and/or amelioration of bacterial or protozoan infections (in particular, bacterial infections) of economically relevant insects, like the honey bee. For example, the compounds of the present invention may be used in the treatment, prevention and/or amelioration of infections with *Bacillus larvae*, i.e. foul brood or malignant foolbrood of bees. Preferably, said animal is a mammal. The meaning of the terms "animal" or "mammal" is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like *Drosophila melanogaster* and nematodes like *Caenorhabditis elegans.* Non-limiting examples of agronomically important animals are sheep, cattle and pig, while, for example, cats and dogs may be considered as economically important animals.

The term "treatment" as used herein, such as, e.g., "treatment of a bacterial infection", "treatment of a protozoan infection" or "treatment of a disease induced by or related to a bacterial infection", is well known in the art. "Treatment of a disease induced by or related to a bacterial infection" implies that the disease has been diagnosed in a patient/subject. A patient/subject suspected of suffering from a disease induced by or related to a bacterial infection typically shows specific clinical and/or pathological symptoms which a skilled person can easily attribute to a specific pathological condition (i.e. diagnose the disease induced by or related to a bacterial infection).

"Treatment of a disease induced by or related to a bacterial infection" may, for example, lead to a halt in the progression of the disease (e.g. no deterioration of symptoms) or a delay in the progression of the disease (in case the halt in progression is of a transient nature only). "Treatment of a disease induced by or related to a bacterial infection" may also lead to a partial response (e.g. amelioration of symptoms) or complete response (e.g. disappearance of symptoms) of the subject/patient suffering from the disease. Such a partial or complete response may be followed by a relapse. It is to be understood that a subject/patient may experience a broad range of responses to a treatment (e.g. the exemplary responses as described herein above).

Treatment, such as, e.g, the treatment of a disease induced by or related to a bacterial infection, may, inter alia, comprise curative treatment (preferably leading to a complete response and eventually to healing of the disease) and palliative treatment (including symptomatic relief).

Also the term "prevention" as used herein, such as, e.g., "prevention of a bacterial infection", "prevention of a protozoan infection" or "prevention of a disease induced by or related to a bacterial infection", is well known in the art. For example, a patient/subject suspected of being prone to suffer from a disease induced by or related to a bacterial infection as defined herein may, in particular, benefit from a prevention of the disease. Said subject/patient may have a susceptibility or predisposition for a disease induced by or related to a bacterial infection, including but not limited to hereditary predisposition. Such a predisposition can be determined by standard assays, using, for example, genetic markers or phenotypic indicators. It is to be understood that a disease induced by or related to a bacterial infection to be prevented in accordance with the present invention has not been diagnosed or cannot be diagnosed in said patient/subject (for example, said patient/subject does not show any clinical or pathological symptoms). Thus, the term "prevention" comprises the use of compounds or compositions of the present invention before any clinical and/or pathological symptoms are diagnosed or determined or can be diagnosed or determined by the attending physician.

The term "amelioration" as used herein, such as, e.g., "amelioration of a bacterial infection", "amelioration of a protozoan infection" or "amelioration of a disease induced by or related to a bacterial infection", is well known in the art. "Amelioration of a disease induced by or related to a bacterial infection" may, for example, refer to a reduction or suppression of clinical and/or pathological symptoms of said disease. The term "amelioration" of (a) bacterial infection(s) as used herein is a subform of the medical intervention and medical treatment with beta-lactones and their derivatives as described herein and, accordingly, also relates to "treatment" of medical disorder, i.e. a bacterial infection. Such an "amelioration" comprises also the treatment of bacterial infections or super-infections when the subject in need of medical intervention is also treated before, during or after such bacterial infections with other antibiotics as described herein. Therefore, the term "amelioration" of a bacterial infection also comprises, but is not limited to, the co-therapeutic use of the beta-lactone compounds as disclosed and described herein with other antibiotics or medicaments used in the treatment of a given disease/disorder. Also the co-therapeutic use of the compounds of the present invention with other drugs than antibiotics is envisaged.

The beta-lactone compounds of the present invention are believed to be characterized by a particularly low cytotoxicity which makes them well-suited for medical uses. For example, beta-lactone compound U1 as shown in FIG. 2 was demonstrated to be non-cytotoxic to human HeLa cells up to a concentration of 1 mM (300 mg/L), as also described in Example 8.

A further embodiment of the present invention relates to the compound described herein above, wherein the bacterial infection induces the formation of biofilms or is associated with the formation of biofilms.

Accordingly, the present invention provides for a method for sterilizing and/or anti-bacterial cleaning of a technical device or instrument, in particular catheters, medical implants, contact lenses and the like, said method comprising the application of the compound or the composition of the present invention on surfaces of said technical device or instrument or on parts thereof. For example, the compound or the composition of the present invention may be applied on surfaces of said technical device or instrument or on parts thereof by spraying, wetting, depositing and/or soaking the technical device or instrument or parts thereof in a composition. All or only some of the various modes of application of the inventive compound or composition as described above may be performed simultaneously or consecutively in arbitrary order. Thereby, the compound or the composition of the present invention may, for example, be applied at concentrations of about 1 mg/L (i.e., 1 mg compound/L) to about 100 mg/L.

In the context of the present invention the term "biofilm" means a complex aggregation (i.e. community) of microorganisms (e.g. bacteria, fungi, algae and/or protozoae) marked by the excretion of a protective and adhesive matrix. Biofilms are also often characterized by surface attachment, structural heterogeneity, genetic diversity, complex community interactions, and an extracellular matrix of polymeric substances. Exemplary polymeric substances are polysaccharides, proteins, lipids and nucleic acids. The biopolymers of biofilms adhere e.g. to the interface of a liquid and a surface, the interface of a liquid and a gas, or to the interface between two liquids. Biofilms are naturally occurring e.g. in acidic pools, on glaciers, at the bottom of streams or rivers and on teeth (plaque formed mainly by *Streptococcus* species). It is known in the art that many bacteria are capable of forming biofilms either alone ore in combination with other microorganisms.

Biofilms have been found to be induced or to be associated with various bacterial infections, such as, e.g., urinary tract infections, infections in cystic fibrosis, middle-ear infections, formation of dental plaques, gingivitis, caries, endocarditis, catheter infections, contact lens associated eye infections or medical implant associated infections. It is known that, inter alia, Gram-positive bacteria such as *Staphylococcus* species (e.g. *Staphylococcus epidermidis* and *Staphylococcus aureus*) and Gram-negative bacteria (e.g. *Pseudomonas aeruginosa* and *Escherichia coli*) are involved in the formation of undesired and malicious biofilms on medical instruments, catheters, medical implants, contact lenses and the like. Furthermore, biofilms contribute in a major way to the morbidity and mortality associated with endocarditis, infections in cystic fibrosis, and infections associated with medical implants such as joint prostheses and heart valves replacements. The terms referring herein above to bacterial infections which induce biofilms or are associated with biofilms, such as "urinary tract infections" and the like are known in the art. A person skilled in the art will know or will be able to identify further bacterial infections which induce the formation of biofilms or which are associated with the formation of biofilms.

In the context of the present invention the term "medical implant" means a medical device which is to replace and to act as a missing biological structure. The term "medical implant" is used herein in the same meaning as "permanent indwelling device". Surfaces of medical implants may be, for example, made of titanium, silicon or apatite. Exemplary medical implants are (subcutenous) drug delivery devices, prosthesis, devices to be placed over or whithin bones to hold a fracture reduction, dental implants, cochlear implants, pacemakers, heart valve replacements and artificial joints (also referred to herein as joint prostheses).

In a preferred embodiment, the present invention relates to the non-therapeutical use of the compound or the composition described herein above for preventing the formation of biofilms or eliminating biofilms on surfaces of a technical device. In one aspect of this embodiment, said preventing or eliminating of biofilms is performed on devices which are not simultaneously contacting the human or animal body. The non-therapeutical use of the compound or composition of the present invention may particularly be useful for preventing the formation of biofilms or for eliminating biofilms on surfaces of technical devices described herein above which cannot be autoclaved or otherwise sufficiently heat-treated, cleaned or disinfected. The present compound or composition may be applied on surfaces of technical devices or parts thereof in order to prevent/eliminate biofilms, for example, by spraying, wetting, depositing and/or soaking the technical device or parts thereof in a composition. All or only some of the various modes of application of the inventive compound or composition as described above may be performed simultaneously or consecutively in arbitrary order. Thereby, the compound or the composition of the present invention may, for example, be applied at concentrations of about 1 mg/L (i.e., 1 mg compound/L) to about 100 mg/L.

Provided is also a method for preventing the formation of biofilms or eliminating biofilms on surfaces of a technical device, said method comprising the application of the compound or the composition of the present invention on surfaces of said technical device or on parts thereof. For example, the compound or the composition of the present invention may be applied on surfaces of said technical devices or on parts thereof by spraying, wetting, depositing and/or soaking the technical device or parts thereof in a composition. All or only some of the various modes of application of the inventive compound or composition as described above may be performed simultaneously or consecutively in arbitrary order. Thereby, the compound or the composition of the present invention may, for example, be applied at concentrations of about 1 mg/L (i.e., 1 mg compound/L) to about 100 mg/L.

In the context of the present invention the term "technical device" means any item which is not an alive human or animal. This definition does not preclude that the technical device may contact a living organism, in particular a microorganism. However, it is to be understood that the "technical device" is not within an alive human or animal body. During the procedure of preventing or eliminating biofilms on surfaces of a technical device said device does also not contact an alive human or animal body. Non-limiting examples of technical devices are catheters, surgical instruments, contact lenses, medical implants, and food-processing devices. The terms "catheter", "surgical instrument", "contact lense", and "food-processing devices" are known in the art. Medical implants have been described herein above. Also plants or parts thereof (e.g. fruits, vegetables or flowers) or non-living animals or parts thereof may be considered as technical device in the context of the present invention. Such plants, non-living animals or parts thereof may, for example, be used in the production or processing of edibles such as food, beverages and the like.

Biofilms can also occur on surfaces of technical devices such as kerosine or oil tanks, water tanks of ships, wet areas within astronautic vessels, submarines or nuclear power plants and on the surface of ship hulls, which might lead to a significant decrease of the speed of these ships. In addition, biofilms on the surface of e.g. ship hulls can contribute to biofouling. Biofilms are also unwanted on the surface of technical devices (e.g. vessels, instruments, tanks, tubings and other equipment) used in food (e.g. dairy products) and beverage (e.g. beer) production.

Without being bound by theory, it is believed that the binding of the compound of the present invention to ClpP may inhibit the activity of bacteria which form part of a biofilm described herein above. As biofilms are considered to be an aggregation of various microorganisms (inter alia, bacteria, fungi or algae), the inhibition of bacterial activity may contribute to the prevention or elimination of biofilms.

In the context of biofilm prevention and elimination on the surface of technical devices and, accordingly, in the method for sterilizing and/or anti-bacterial cleaning of a technical device or instrument and also in the method for preventing the formation of biofilms or eliminating biofilms on surfaces of a technical device, the compound or composition of the present invention can be applied either alone or in combination with further means and methods, like heat-treatment, UV-irradiation or disinfection, or in combination with antibiotics. It is preferred herein that said further means and methods prevent the formation of biofilms or eliminate biofilms on the surface of technical devices. It is also envisaged that these methods may destroy biofilms, for example, by mechanical scrubbing or simply cleaning the surface of a technical device, for example, using a composition comprising one or more detergents as described herein above.

These further means and methods may be applied simultaneously, after and/or before the inventive compound or composition is applied in accordance with the present invention. A person skilled in the art knows how to apply the further means and methods in order to destroy biofilms.

In particular, heat-labile technical devices may not be heat-treated, e.g. autoclaved. The term "heat-labile technical devices" used in the context of the present invention means technical devices which cannot be heat-treated for disinfection, e.g. by autoclaving, or which are destroyed or deformed at temperatures typical for heat-treatment, e.g. temperatures from about 45° C. to 150° C. The compound or the composition of the present invention may also be useful in case heat-treatment, disinfection and the like might destroy or damage the surfaces of technical devices such as catheters or medical implants. The compound or composition may also be used in food or beverage processing/production, in particular when edibles cannot be (sufficiently) sterilised by means and methods known in the art. For example, such sterilisation might destroy the structure, taste, look or colour of the food or beverage and accordingly is to be avoided or has to be carried out in a way that does not sufficiently remove/inactivate bacteria, in particular pathogenic bacteria.

In the context of the present invention, the term "disinfection" means the destruction of microorganisms such as bacteria. "Disinfectants" are usually applied to non-living objects, while antibiotics generally destroy microorganisms within the body and antiseptics destroy microorganisms on living tissue. Often disinfectants do not sterilise the technical devices completely (i.e. the complete elimination of all microorganisms/bacteria) but merely reduce the number of living microorganisms per area disinfected. Non-limiting examples of disinfectants are aldehydes (e.g. glutaraldehyde), alcohols (such as ethanol, isopropanol and the like), and halogens. Non-limiting examples of halogens are chloramine, chloramine-T, chlorine, hypochlorites and iodine. Also oxidizing agents (e.g. chlorine dioxide, hydrogen peroxide, ozone, acidic electrolyzed water, peracetic acid, and potassium permanganate), phenolics (e.g. phenol, O-phenylphenol, thymol and the like), quaternary ammonium compounds and polyaminopropyl biguanide may be considered as disinfectants. Exemplary antiseptics are alcohols, quaternary ammonium compounds, boric acid, chlorhexidine gluconate, hydrogen peroxide, iodine, mercurochrome, phenol, and sodium chloride.

The compound of the present invention may be particularly useful when the disinfectant employed may not be capable of sterilising the technical device. In a preferred embodiment, the means and methods described herein above (such as heat-treatment, UV irradiation, mechanical scrubbing or disinfection) are not capable of eliminating all bacterial. For example, less than 100%, more preferably less than 99%, 98%, 97%, 96%, 95% or 90% of the bacteria are eliminated.

It is also envisaged herein that the compound or composition of the present invention may not only be used for preventing the formation of biofilms or eliminating biofilms on surfaces of technical devices but may also be used non-therapeutically for inhibiting the activity of bacteria which do not form part of a biofilm. The compound or composition may, for example, be used as an antibacterial agent and be employed for inhibiting the activity of bacteria (in particular Gram-positive bacteria) which are present on surfaces of technical devices as described herein above. For example, *Listeria* (e.g. *Listeria monocytogenes*) contaminations in food, particularly in meat and dairy products and in fruits and vegetables, like cheese, can cause infections when incorporated by a subject.

The invention relates to the following deoxynucleotide and amino acid sequences and sequence alignments.

Sequence 1: A) Nucleic acid sequence (588 bp) and B) amino acid sequence of the ATP-dependent Clp protease (proteolytic subunit ClpP) from *Staphylococcus aureus* subsp. *aureus* NCTC 8325.

Sequence 2: A) Nucleic acid sequence (585 bp) and B) amino acid sequence of the ATP-dependent Clp protease (proteolytic subunit ClpP) from *Staphylococcus epidermis* ATCC 12228.

Sequence 3: A) Nucleic acid sequence (597 bp) and B) amino acid sequence of the ATP-dependent Clp protease (proteolytic subunit ClpP) from *Listeria welshimeri* serovar 6b str. SLCC5334.

Sequence 4: A) Nucleic acid sequence (597 bp) and B) amino acid sequence of the ATP-dependent Clp protease (proteolytic subunit ClpP) from *Listeria monocytogenes* str. 4b F2365.

Sequence Alignment 1: Sequence alignment of the amino acid sequences of ATP-dependent Clp protease from *Staphylococcus aureus* subsp. *aureus* NCTC 8325 (S.) (Sequence 1B) and from *Listeria monocytogenes* str. 4b F2365 (L.) (Sequence 4B). The sequences show a 79.1% identity in 191 residues overlap (Score: 784.0; Gap frequency: 0.0%).

Sequence Alignment 2: Sequence alignment of the amino acid sequences of ATP-dependent Clp protease from *Staphylococcus aureus* subsp. *aureus* NCTC 8325 (SA.) (Sequence 1B) and from *Staphylococcus epidermis* ATCC 12228 (SE.) (Sequence 2B). The sequences show a 98.4% identity in 193 residues overlap (Score: 950.0; Gap frequency: 0.0%).

Sequence Alignment 3: Sequence alignment of the amino acid sequences of ATP-dependent Clp protease from *Listeria monocytogenes* str. 4b F2365 (LM.) (Sequence 4B) and from *Listeria welshimeri* serovar 6b str. SLCC5334 (LW.) (Sequence 3B). The sequences show a 98.5% identity in 198 residues overlap (Score: 984.0; Gap frequency: 0.0%).

```
Sequence 1.
A.
    1 atgaatttaa ttcctacagt tattgaaaca acaaaccgcg gtgaacgtgc atatgatata
   61 tactcacgtt tattaaaaga ccgtattatt atgttaggtt cacaaattga tgacaacgta
  121 gcaaattcaa tcgtatcaca gttattattc ttacaagcgc aagactcaga gaaagatatt
  181 tatttataca ttaattcacc aggtggaagt gtaacagctg gttttgcgat ttatgataca
  241 attcaacaca ttaaacctga tgttcaaaca atttgtatcg gtatggctgc atcaatggga
  301 tcattcttat tagcagctgg tgcaaaaggt aaacgtttcg cgttaccaaa tgcagaagta
  361 atgattcacc aaccattagg tggtgctcaa ggacaagcaa ctgaaatcga aattgctgca
  421 aatcacattt taaaaacacg tgaaaaatta aaccgcattt tatcagagcg tactggtcaa
  481 agtattgaaa aaatacaaaa agacacagat cgtgataact tcttaactgc agaagaagct
  541 aaagaatatg gcttaattga tgaagtgatg gtacctgaaa caaaataa
B.
MNLIPTVIETTNRGERAYDIYSRLLKDRI IMLGSQIDDNVANSIVSQLLFLQAQDSEKDIYLY
INSPGGSVTAGFAIYDTIQHIKPDVQTICIGMAASMGSFLLAAGAKGKRFALPNAEVMIHQPL
GGAQGQATEIEIAANHILKTREKLNRILSERTGQSIEKIQKDTDRDNFLTAEEAKEYGLIDEV
MVPETK Sequence 2.
A.
    1 atgaatttaa ttcctacagt tattgaaaca actaaccgcg gtgaacgtgc gtatgatata
   61 tattcacgtt tgttgaaaga ccgtattatc atgctaggtt ctcaaattga tgataacgta
  121 gctaactcta ttgtgtcaca attattattc ttgcaagcgc aagattctga aaaggatatt
  181 tatttatata ttaattcacc aggtggcagt gtaactgctg gatttgctat ttatgatact
  241 atccaacata tcaaaccaga cgttcaaaca atctgtattg gtatggcagc gtctatgggt
  301 tcattcttgt tagcagcagg tgcaaaaggt aaacgatttg cgctacctaa tgctgaagtt
  361 atgattcacc aaccattagg tggtgcacaa ggacaagcaa ctgaaattga aattgcagca
  421 aatcatattt taaaaacacg tgaaaaatta aatcgtattt tatcagaacg tacaggtcaa
  481 tcaattgaaa aaattcaaca agatactgat cgcgacaact tcttaacagc tgcagaagct
  541 aaagaatatg gattaattga tgaagtaatg gaaccagaaa aataa
B.
mnliptviet tnrgeraydi ysrllkdrii mlgsqiddnv ansivsqllf lqaqdsekdi
ylyinspggs vtagfaiydt ighikpdvqt icigmaasmg sfllaagakg krfalpnaev
mihqplggaq gqateieiaa nhilktrekl nrilsertgq siekiqqdtd rdnfltaaea
keyglidevm epek Sequence 3.
A.
    1 atgaacttaa ttccaacagt aattgaacaa acaagccgtg gtgaacgcgc atatgacatt
   61 tattcacgtt tattaaaaga cagaattatt atgttaggct ctgcaattga tgataacgtt
  121 gctaactcta tcgtttctca attattattc cttgatgcac aagatcctga aaaagatatt
  181 ttcttatata tcaattctcc aggaggaagt atttcagctg gtatggcgat ttatgataca
  241 atgaatttcg ttaaagcaga tgtgcaaact attggtatgg gatggctgc ttccatggga
  301 tcattcttac taacagccgg tgcaaacggt aaacgctttg ccttaccaaa tgcggaaatc
  361 atgattcacc aaccacttgg tggcgctcaa ggtcaagcaa ctgaaatcga aattgctgct
  421 cgtcacattt tgaaaatcaa agaacgtatg aatactatta tgtctgaaaa aactggtcaa
  481 ccatatgaag ttattgctcg tgatacagat cgtgataatt tcatgactgc tcaagaagca
  541 aaagattacg gcttaattga tgatatcatc gtaaacaaag ctggcttaaa gggctaa
B.
mnliptvieq tsrgeraydi ysrllkdrii mlgsaiddnv ansivsqllf ldagdpekdi
flyinspggs isagmaiydt mnfvkadvqt igmgmaasmg sflltagang krfalpnaei
mihqplggaq gqateieiaa rhilkikerm ntimsektgq pyeviardtd rdnfmtaqea
kdygliddii vnkaglkg Sequence 4.
A.
    1 atgaacttaa ttccaacagt aatcgaacaa actagccgcg gtgaacgtgc atacgacatt
   61 tattcccgtt tattaaaaga cagaattatt atgttaggat ctgcaattga tgataacgtg
  121 gcgaattcga tcgtttctca attactcttc ttagatgcac aagatcctga aaaagatatt
  181 ttcctatata tcaattcacc aggtggaagt atttcagctg gtatggccat ttacgataca
  241 atgaatttcg ttaaagcaga cgtacaaact atcggcatgg gtatggcagc ttccatgggc
  301 tcattcttac taacagctgg tgcaaatggc aaacggtttg ccttgccaaa cgctgaaatt
  361 atgattcacc aaccacttgg tggcgctcaa ggtcaagcga ctgaaatcga aatcgctgct
  421 cgccacattt taaaaatcaa agaacgtatg aatacgatta tggctgagaa aactggtcaa
  481 ccgtatgaag tcattgctcg tgatacagat cgtgataatt tcatgactgc acaagaagca
  541 aaagattacg gcttaattga tgatatcatc attaacaaat ctggcttaaa aggctaa
B.
mnliptvieq tsrgeraydi ysrllkdrii mlgsaiddnv ansivsqllf ldaqdpekdi
flyinspggs isagmaiydt mnfvkadvqt igmgmaasmg sflltagang krfalpnaei
mihqplggaq gqateieiaa rhilkikerm ntimaektgq pyeviardtd rdnfmtagea
kdygliddii inksglkg
```

```
Sequence Alignment 1.
  S.  MNLIPTVIETTNRGERAYDIYSRLLKDRIIMLGSQIDDNVANSIVSQLLFLQAQDSEKDI
  L.  MNLIPTVIEQTSRGERAYDIYSRLLKDRIIMLGSAIDDNVANSIVSQLLFLDAQDPEKDI
      ********* * ************************ **************** *** ****

S.  YLYINSPGGSVTAGFAIYDTIQHIKPDVQTICIGMAASMGSFLLAAGAKGKRFALPNAEV
  L.  FLYINSPGGSISAGMAIYDTMNFVKADVQTIGMGMAASMGSFLLTAGANGKRFALPNAEI
       ********* ** *****   * ***** *********** *** **********

S.  MIHQPLGGAQGQATEIEIAANHILKTREKLNRILSERTGQSIEKIQKDTDRDNFLTAEEA
  L.  MIHQPLGGAQGQATEIEIAARHILKIKERMNTIMAEKTGQPYEVIARDTDRDNFMTAQEA
      ******************** **** *   *   *  *** *   ******* **  **

S.  KEYGLIDEVMV
  L.  KDYGLIDDIII
      * *****

Sequence Alignment 2.
  SA. MNLIPTVIETTNRGERAYDIYSRLLKDRIIMLGSQIDDNVANSIVSQLLFLQAQDSEKDI
  SE. MNLIPTVIETTNRGERAYDIYSRLLKDRIIMLGSQIDDNVANSIVSQLLFLQAQDSEKDI
      ************************************************************

SA. YLYINSPGGSVTAGFAIYDTIQHIKPDVQTICIGMAASMGSFLLAAGAKGKRFALPNAEV
  SE. YLYINSPGGSVTAGFAIYDTIQHIKPDVQTICIGMAASMGSFLLAAGAKGKRFALPNAEV
      ************************************************************

SA. MIHQPLGGAQGQATEIEIAANHILKTREKLNRILSERTGQSIEKIQKDTDRDNFLTAEEA
  SE. MIHQPLGGAQGQATEIEIAANHILKTREKLNRILSERTGQSIEKIQQDTDRDNFLTAAEA
      ********************************************** ********* **

SA. KEYGLIDEVMVPE
  SE. KEYGLIDEVMEPE
      ********** **

Sequence Alignment 3.
  LM. MNLIPTVIEQTSRGERAYDIYSRLLKDRIIMLGSAIDDNVANSIVSQLLFLDAQDPEKDI
  LW. MNLIPTVIEQTSRGERAYDIYSRLLKDRIIMLGSAIDDNVANSIVSQLLFLDAQDPEKDI
      ************************************************************

LM. FLYINSPGGSISAGMAIYDTMNFVKADVQTIGMGMAASMGSFLLTAGANGKRFALPNAEI
  LW. FLYINSPGGSISAGMAIYDTMNFVKADVQTIGMGMAASMGSFLLTAGANGKRFALPNAEI
      ************************************************************

LM. MIHQPLGGAQGQATEIEIAARHILKIKERMNTIMAEKTGQPYEVIARDTDRDNFMTAQEA
  LW. MIHQPLGGAQGQATEIEIAARHILKIKERMNTIMSEKTGQPYEVIARDTDRDNFMTAQEA
      ********************************** *************************

LM. KDYGLIDDIIINKSGLKG
  LW. KDYGLIDDIIVNKAGLKG
      ********** ** ****
```

The invention is illustrated by the following non-limiting figures and examples.

FIG. 1: Exemplary synthetic route and biomimetic structures of the beta-lactones according to the invention. The term LDA refers to lithium diisopropylamine. Hexynal is used herein in the same meaning as 5-hexynaldehyde and -PhSLi refers to lithium thiophenolate.

FIG. 2 (A and B): Beta-lactones (including compounds in accordance with the invention and reference compounds) which were tested for antibacterial activity.

Figure 3:
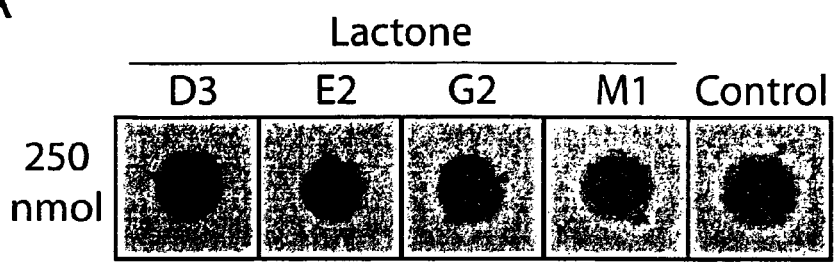
Figure 3:
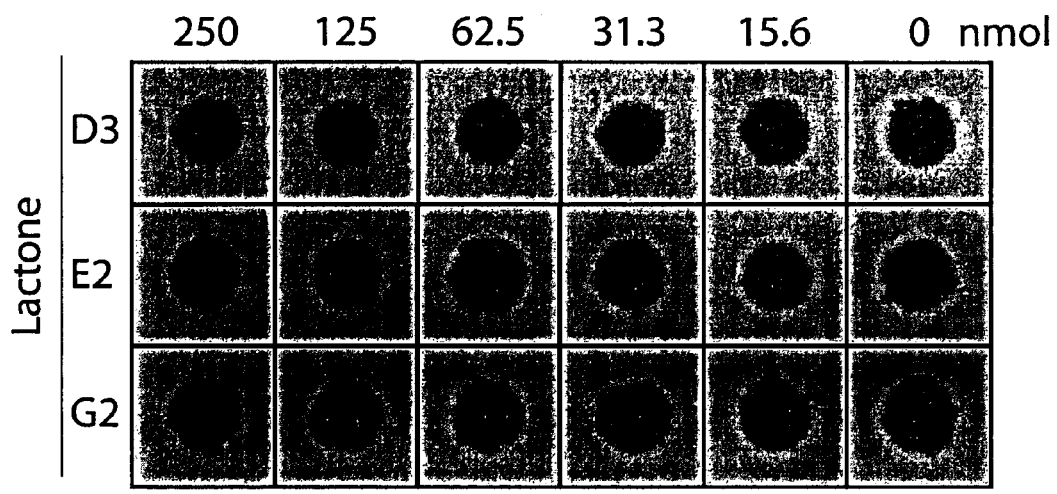

FIG. 3: Blood agar plate-based assay illustrating that beta-lactones have an effect on the haemolysis abilities of *Staphylococcus aureus*. 2.5 μL of *S. aureus* LB dilution ($OD_{600}$=0.13 corresponding to approx. 1×10$^8$ cfu/ml) and 2.5 μL DMSO/lactone in DMSO were applied on Whatman Cards placed on 5% sheep blood agar plates (Heipha Diagnostika, Eppelheim, Germany) and incubated at 37° C. over night. A) Direct comparison of beta-lactones as shown in FIG. 2 at a total amount of 250 nmol applied on Whatman Cards. B) Dose down with beta-lactone compounds D3, E2 and G2 at applied concentrations of 100 mM, 50 mM, 25 mM, 12.5 mM, 6.25 mM and 0 mM (corresponding to total amounts of 250 nmol, 125 nmol, 62.5 nmol, 31.3 nmol, 15.6 nmol and 0 nmol, respectively).

Figure 4:
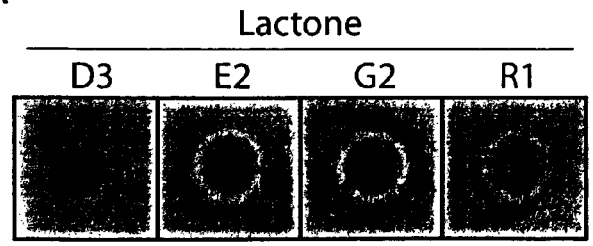
Figure 4:
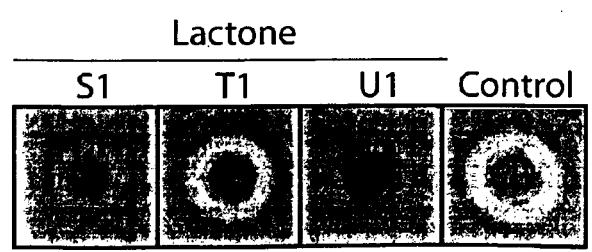
Figure 4:
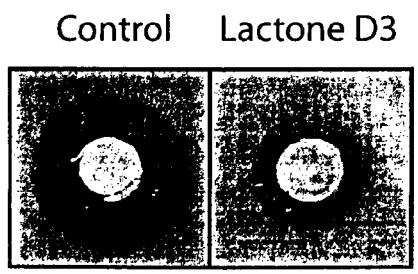

FIG. 4: Agar plate-based virulence assays. A) Comparative haemolysis assay with a total amount of 250 nmol of the respective beta-lactone as shown in FIG. 2. B) DNase assay using DNA containing agar plates reveals an effect of beta-lactone D3 at 250 nmol on the amount of extracellular DNase.

Figure 5:
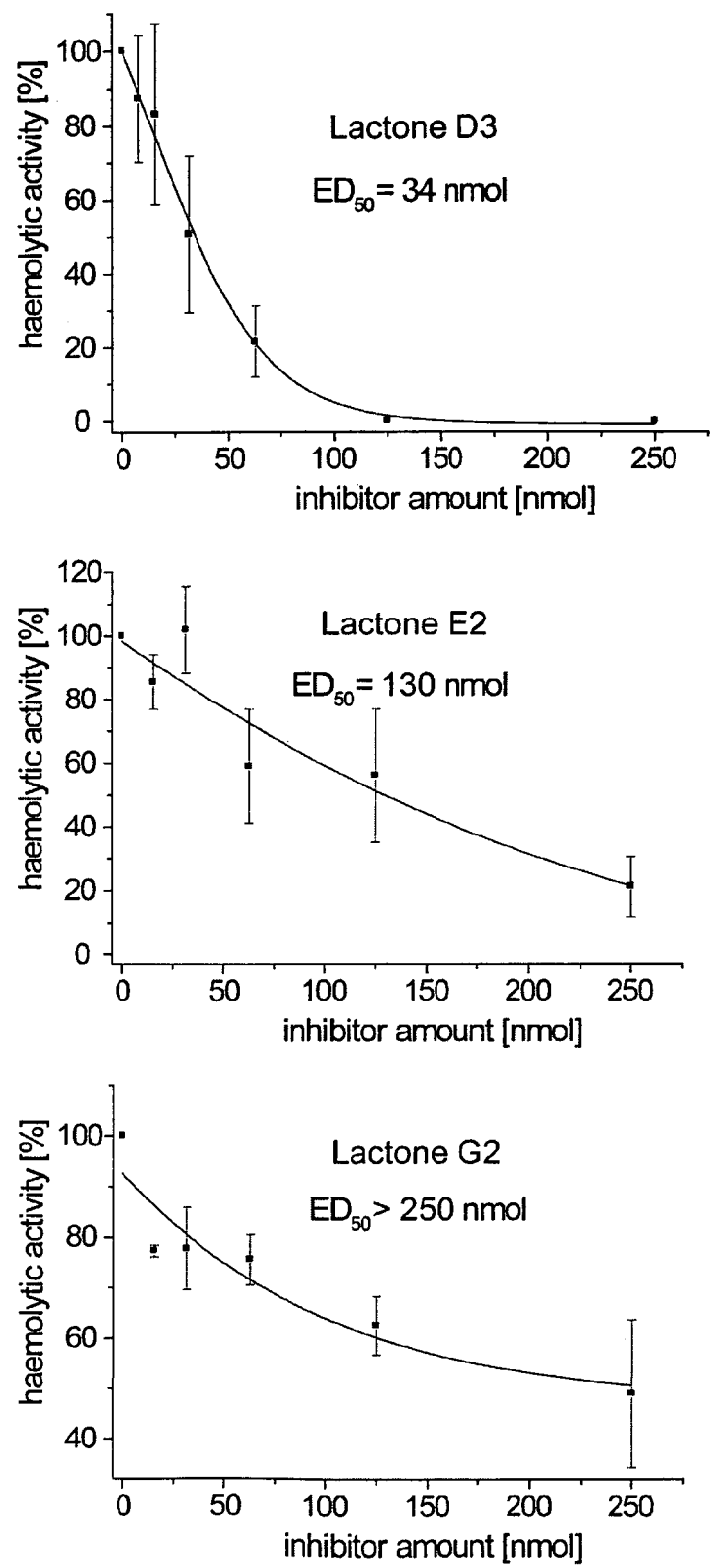

FIG. 5: Haemolytic activity of three beta-lactones as shown in FIG. 2 according to the invention in relation to the total amount of the respective beta-lactone employed, whereby a haemolysis zone of 1.5 mm was set as 100% haemolytic activity.

Figure 6:
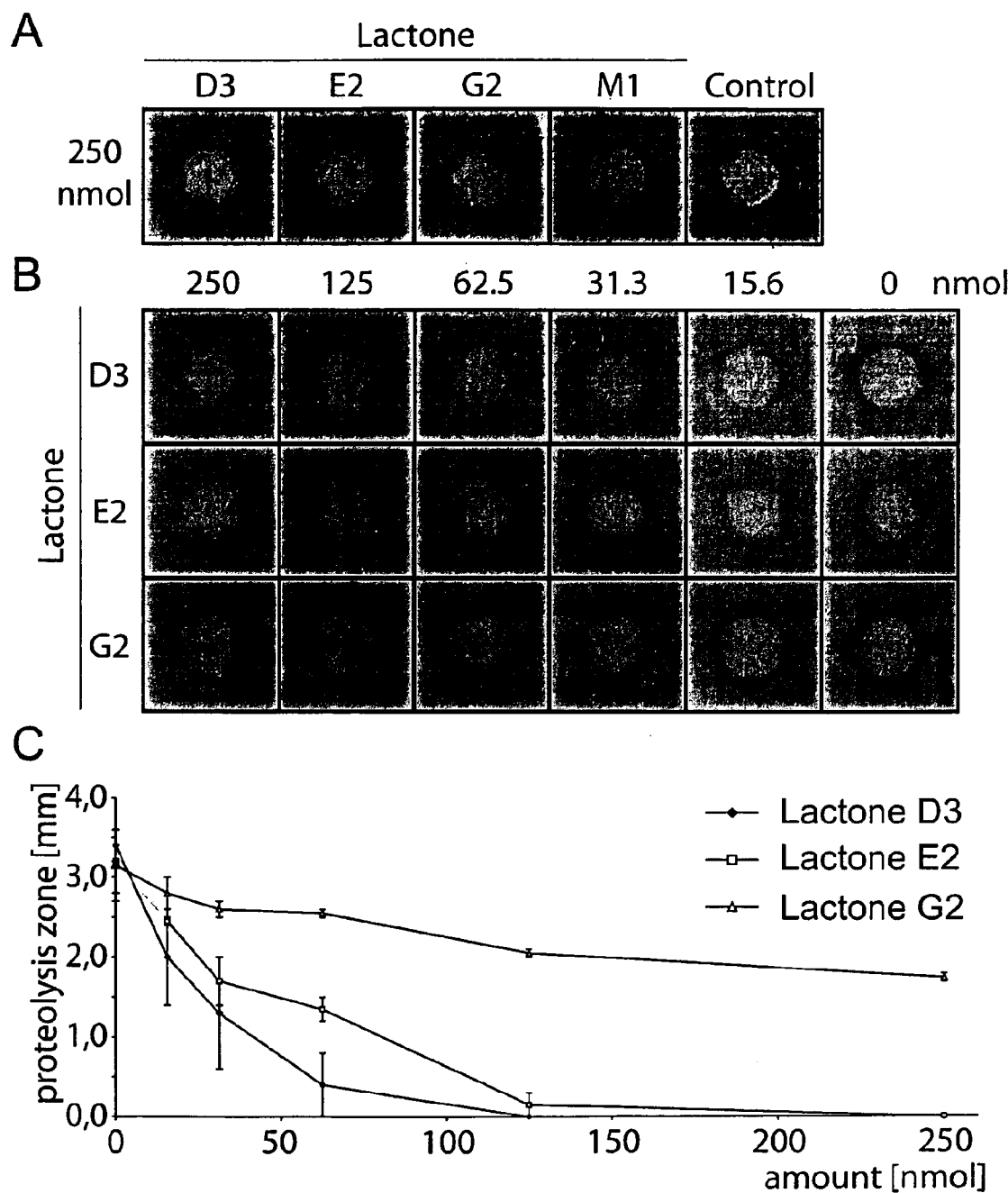

FIG. 6: Milk agar plate-based assay illustrating that beta-lactones have an effect on the proteolysis abilities of *Staphylococcus aureus*. 2.5 μL of *S. aureus* LB dilution ($OD_{600}$=0.13 corresponding to approx. 1×10$^8$ cfu/ml) and 2.5 μL DMSO/beta-lactone in DMSO were applied on Whatman Cards placed on 1% skim milk LB agar plates and incubated at 37° C. over night. A) Direct comparison of beta-lactones as shown in FIG. 2 at a total amount of 250 nmol applied on Whatman Cards. B) Dose down with beta-lactones D3, E2 and G2 at applied concentrations of 100 mM, 50 mM, 25 mM, 12.5 mM, 6.25 mM and 0 mM (corresponding to total amounts of 250 nmol, 125 nmol, 62.5 nmol, 31.3 nmol, 15.6 nmol and 0 nmol, respectively). C) Proteolysis zone size plotted against the total amount of the respective beta-lactone.

Figure 7:
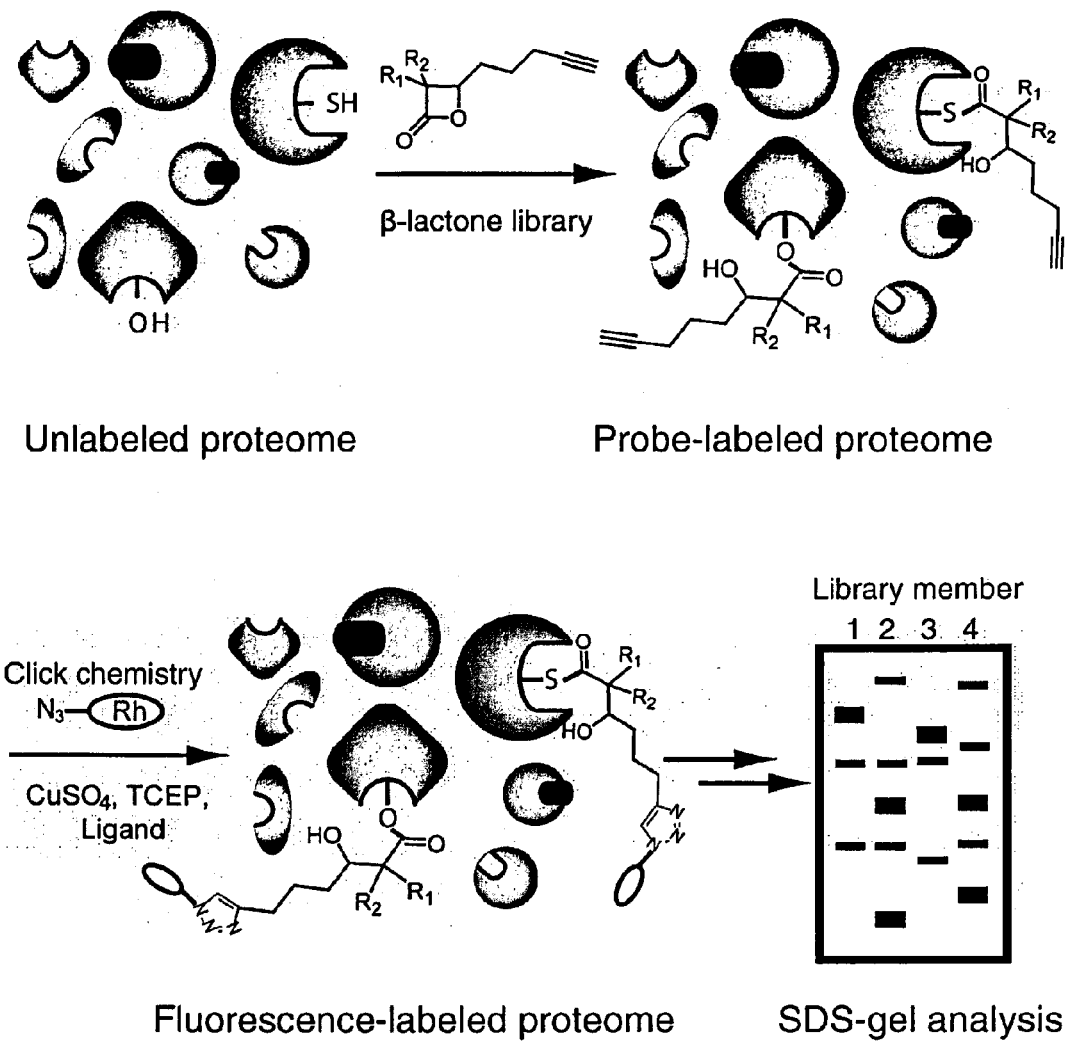

FIG. 7: Proteomes are first treated with the beta-lactone compounds and subsequently appended with a fluorescent dye via click chemistry (CC). Labeled proteomes are run on SDS-PAGE and visualized by fluorescence scanning. The term TCEP refers to tris(2-carboxyethyl)phosphine.

Figure 8:
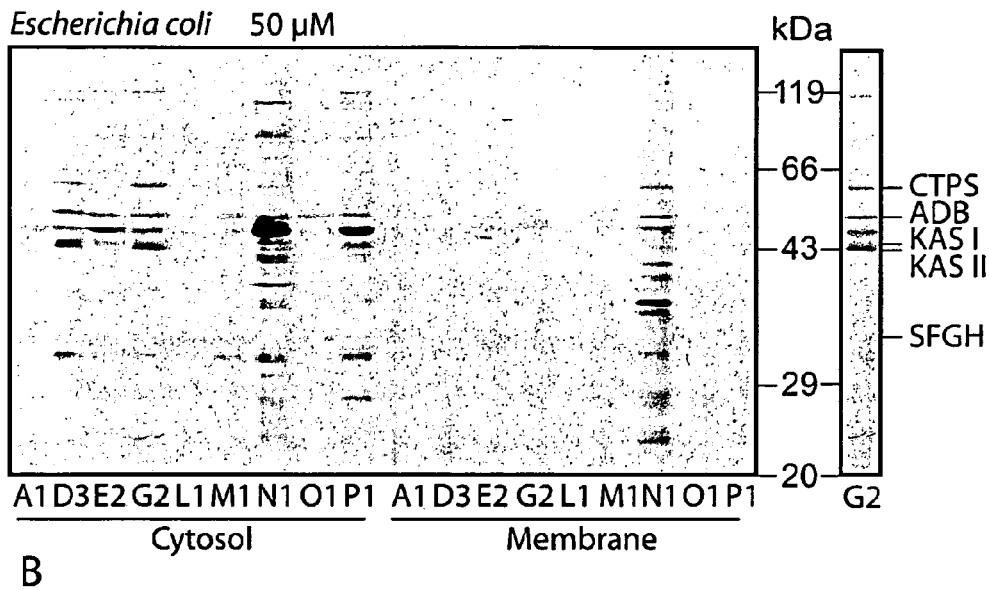
Figure 8:
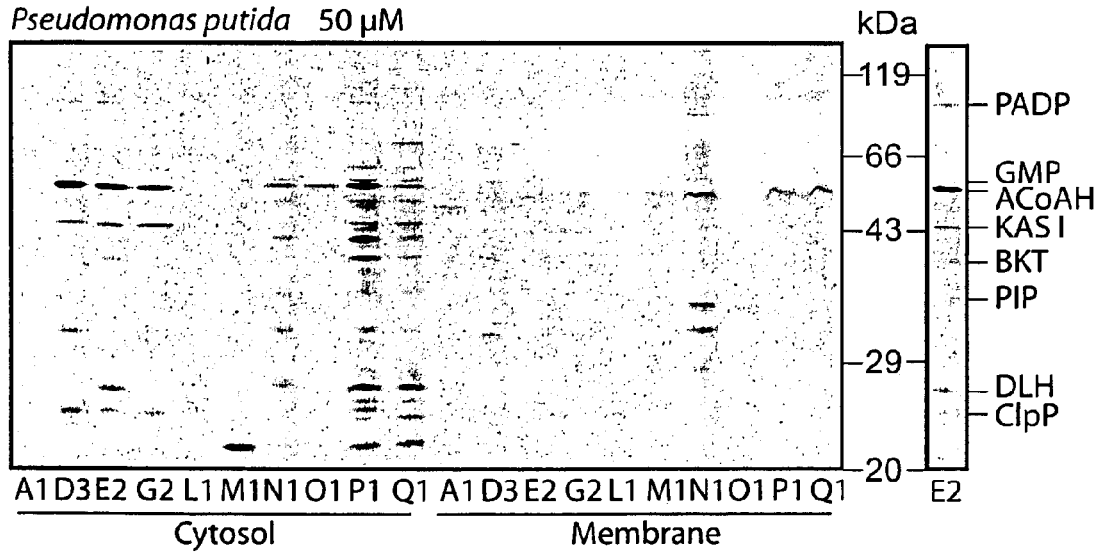
Figure 8:
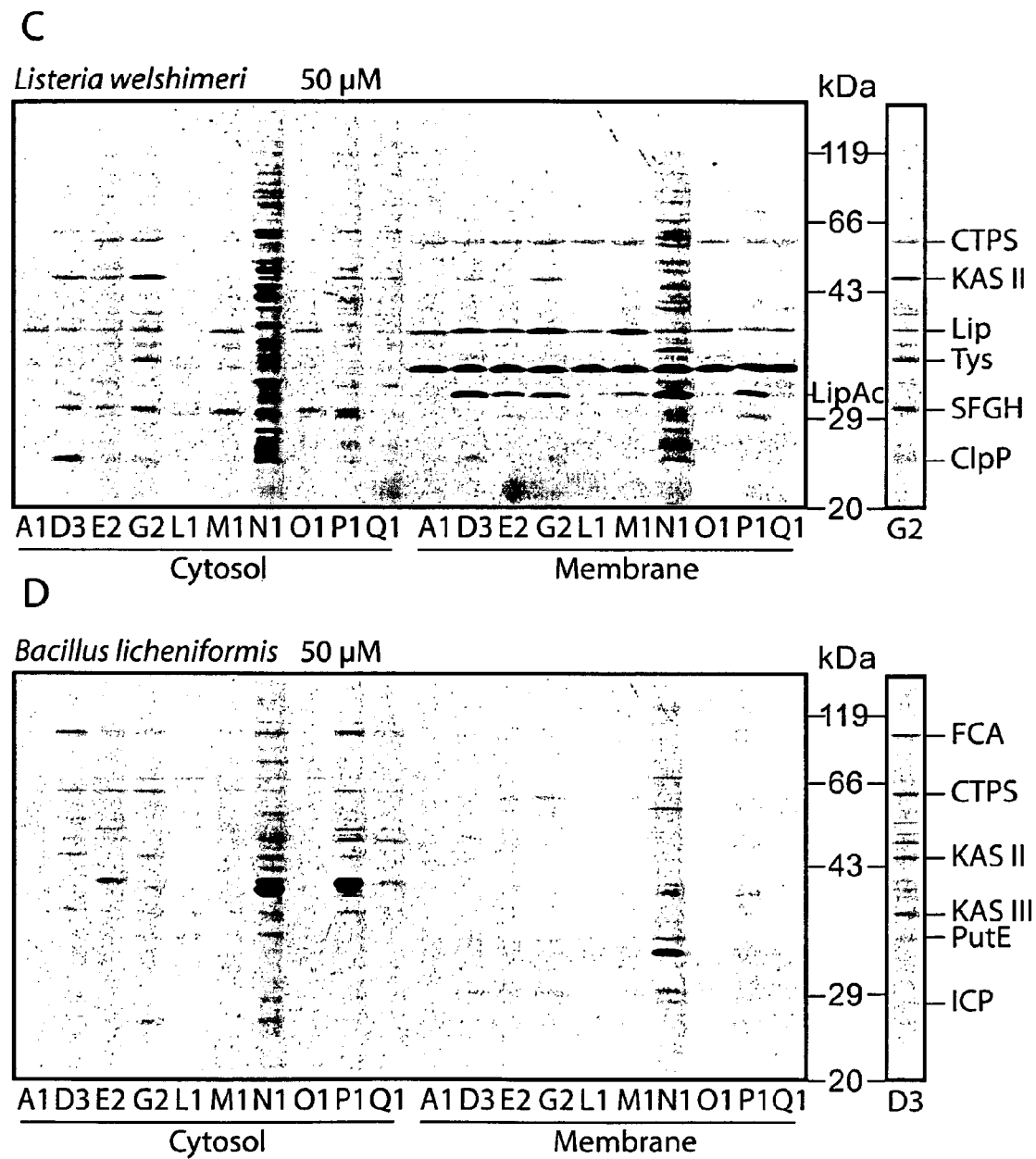
Figure 8:
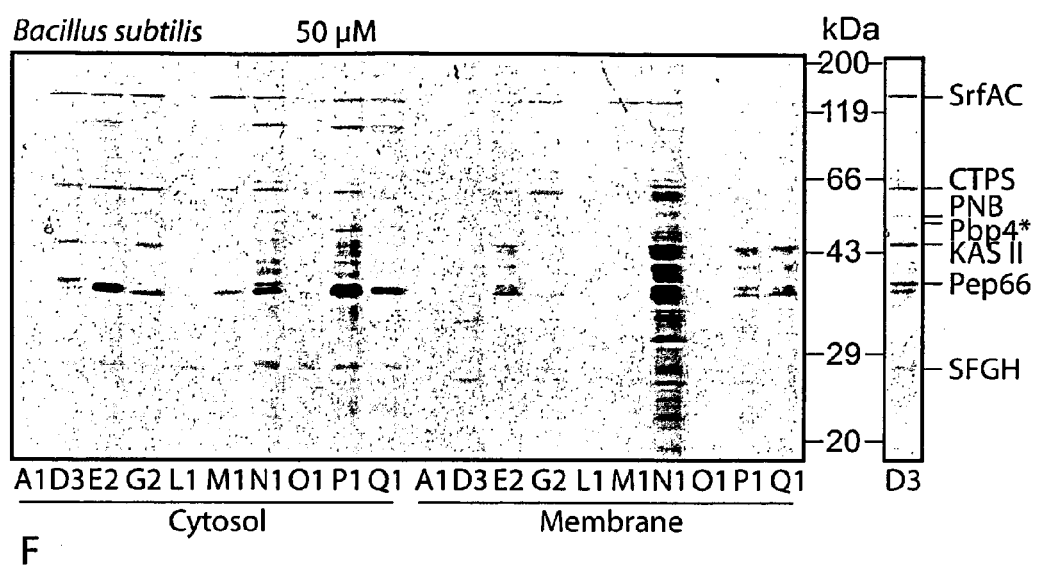
Figure 8:
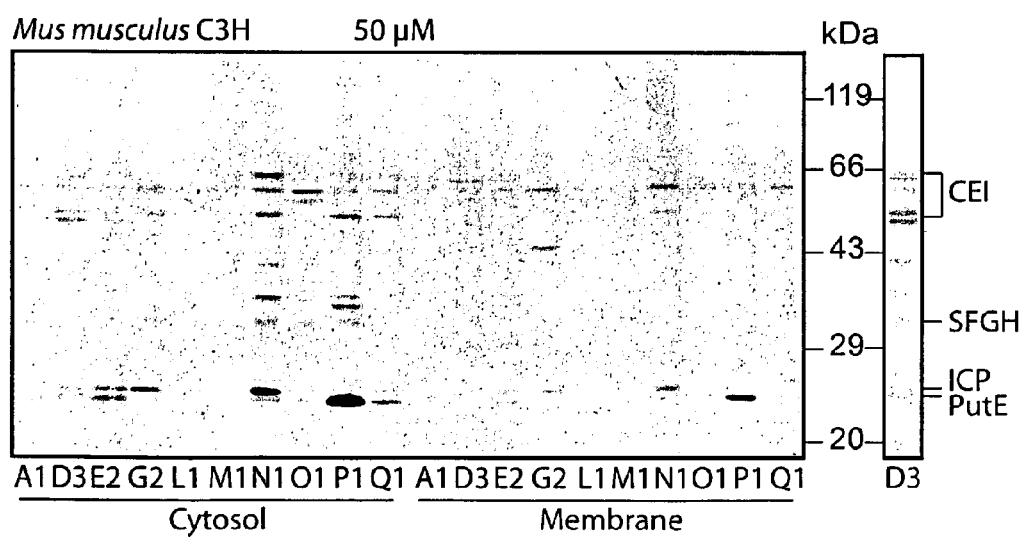

FIG. 8: Labeling profiles of the proteomes in cytosol and membrane with the beta-lactones as shown in FIG. 2. For a list of abbreviations, please refer to Example 6, Table 1.

Figure 9:
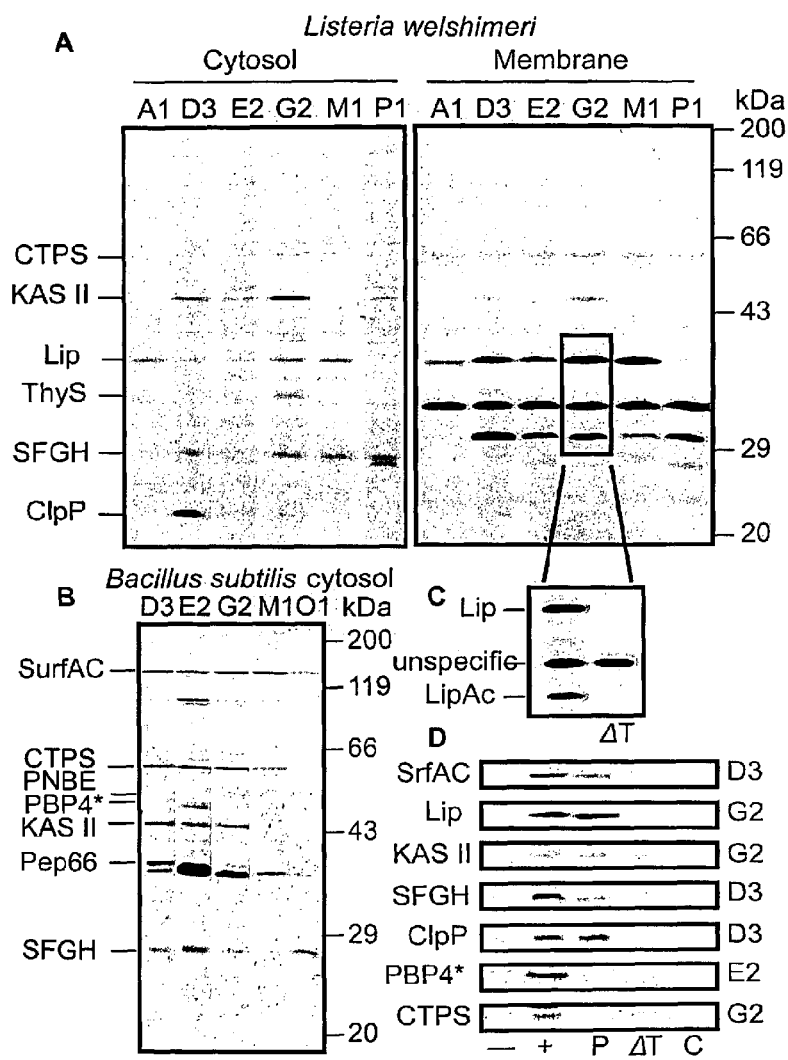

FIG. 9: Testing of beta-lactones against bacterial proteomes. A) Fluorescent gel of *L. welshimeri* cytosol and membrane proteomes after treatment with selected beta-lactones as shown in FIG. 2. Enzyme identities are assigned to the corresponding gel band (for a list of abbreviations, please refer to Example 6, Table 1). B) Fluorescent gel of *B. subtilis* cytosol proteome showing identified enzyme targets. C) All reactions were carried out with a heat control (ΔT) to identify unspecific labeling. An example is shown for G2 (FIG. 2) in the membrane proteome (boxed). D) Examples of recombinantly expressed enzymes (−: before induction, +: after induction, P: native proteome, ΔT: after induction/heat control, C: after induction/no probe).

Figure 10:
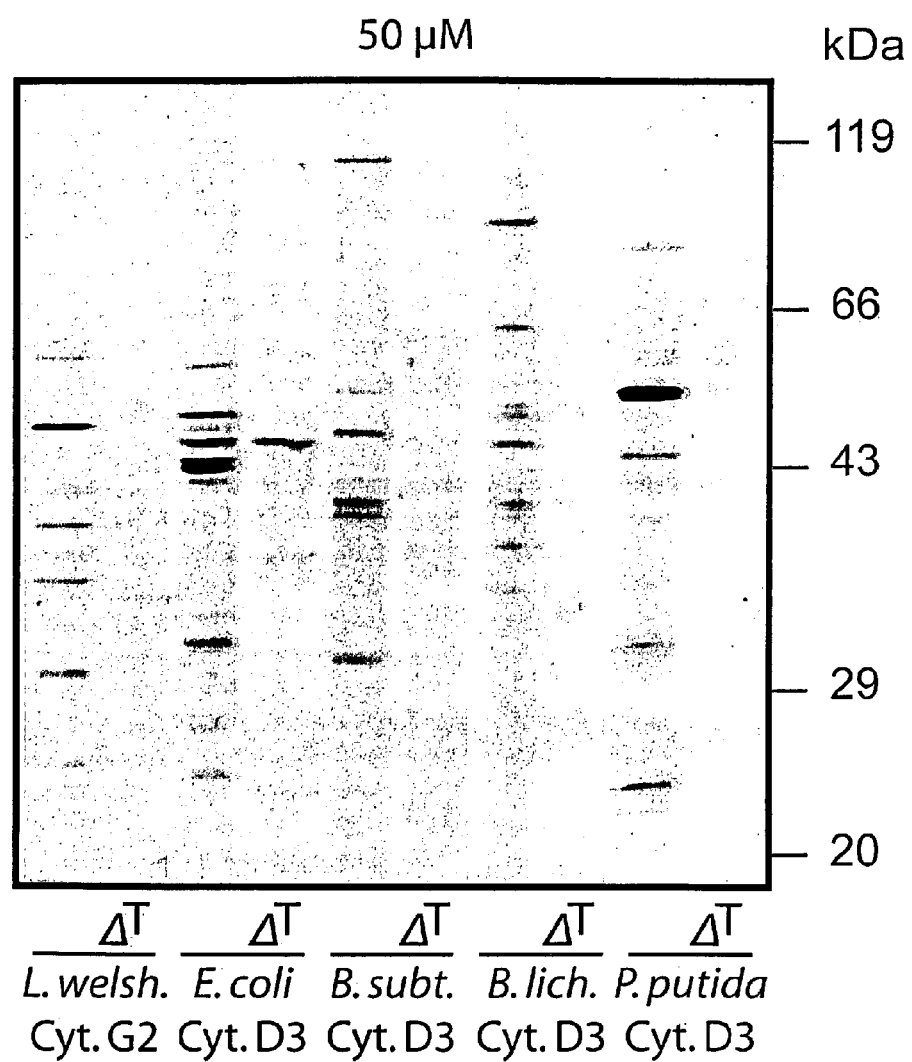

FIG. 10: Representative examples of native proteomes with their corresponding heat denatured controls. The majority of the labeled part of the proteome is shown to be heat sensitive and thus can be regarded as a result of affinity binding events.

Figure 11:
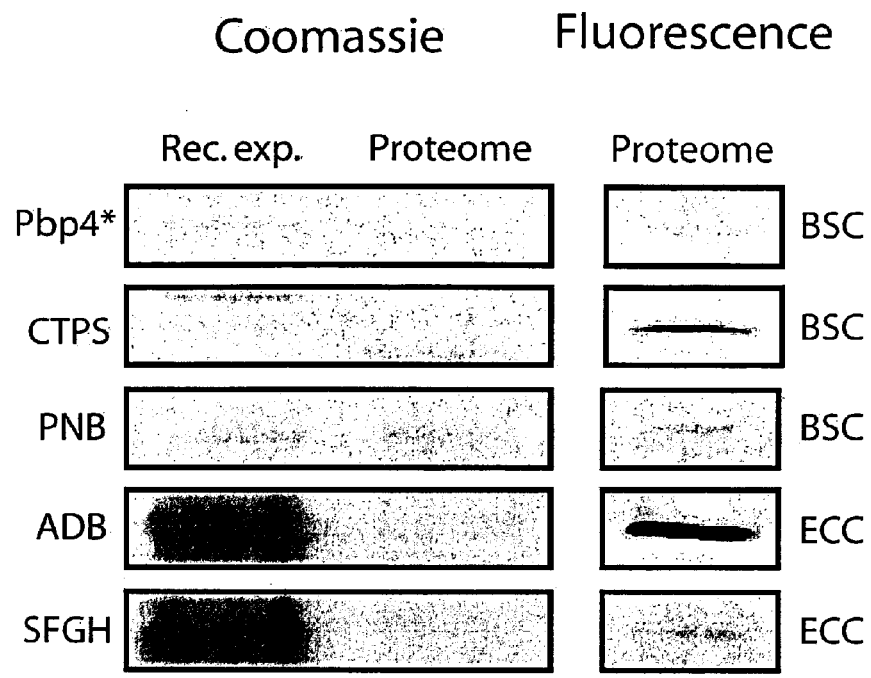

FIG. 11: Comparison between relative protein intensities. Left side: visualized with Coomassie staining. Right side: enzyme labeling visualized by fluorescence scanning. Most labeled proteins stained by Coomassie are of very low abundance in the proteome, so that corresponding overexpressed enzymes were run next to them in order to identify the correct region of the gel. For a list of abbreviations, please refer to Example 6, Table 1. The terms BSC and ECC refer to *Bacillus subtilis* cytosol and *Escherichia coli* cytosol, respectively.

Figure 12:
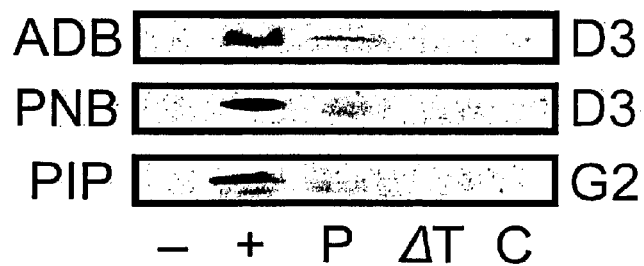

FIG. 12: Recombinantly expressed enzymes in addition to FIG. 9 (−: before induction, +: after induction, P: native proteome, ΔT: after induction/heat control, C: after induction/no probe). For a list of abbreviations, please refer to Example 6, Table 1. The term PNB is also referred to herein as PNBE.

Figure 13:
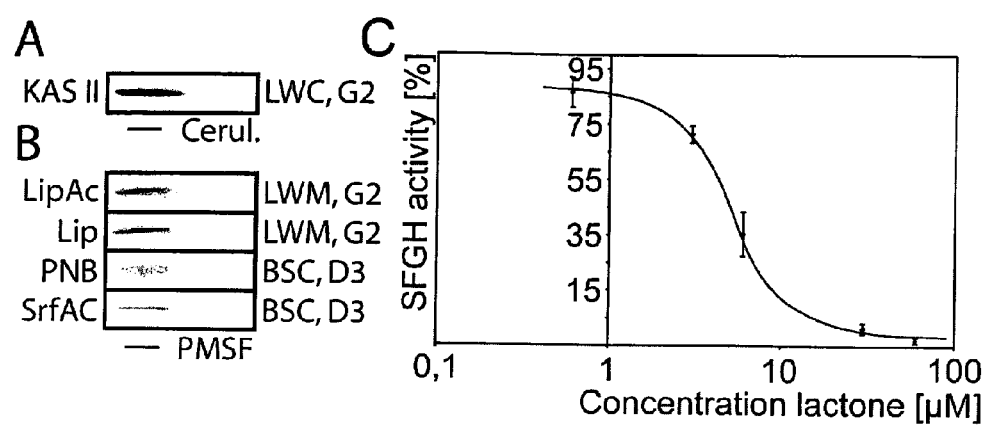

FIG. 13: Active site competition assays and $IC_{50}$. A) Competition experiment with KAS II with and without 100 fold excess of cerulenin in presence of the beta-lactone probe G2. B) Competition experiments with several serine proteases with and without 100 fold excess of PMSF in presence of the corresponding beta-lactone probes (LWC: *L. welshimeri* cytosol, LWM: *L. welshimeri* membrane, BSC: *B. subtilis* cytosol). C) $IC_{50}$ of 5 μM for SFGH. For a list of abbreviations, please refer to Example 6, Table 1. The term PNB is also referred to herein as PNBE.

Figure 14:
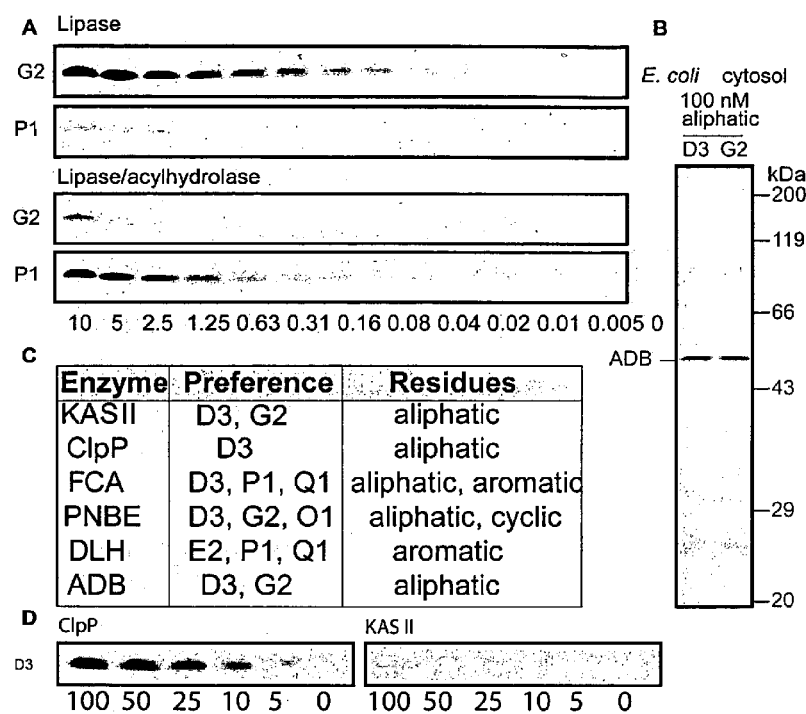

FIG. 14: Sensitivity and specificity of the beta-lactones for individual enzymes. A) Dose down of selected beta-lactone probes in the *L. welshimeri* proteome, displaying sensitivity and target selectivity of beta-lactones G2 and P1. B) ADB is the only enzyme in *E. coli* cytosol which is labeled by D3 and G2 at 100 nM. C) List of selected enzymes with their corresponding beta-lactone probe preferences. D) In vivo labeling of *L. welshimeri* with beta-lactone D3 in varying concentrations. For a list of abbreviations, please refer to Example 6, Table 1.

Figure 15:
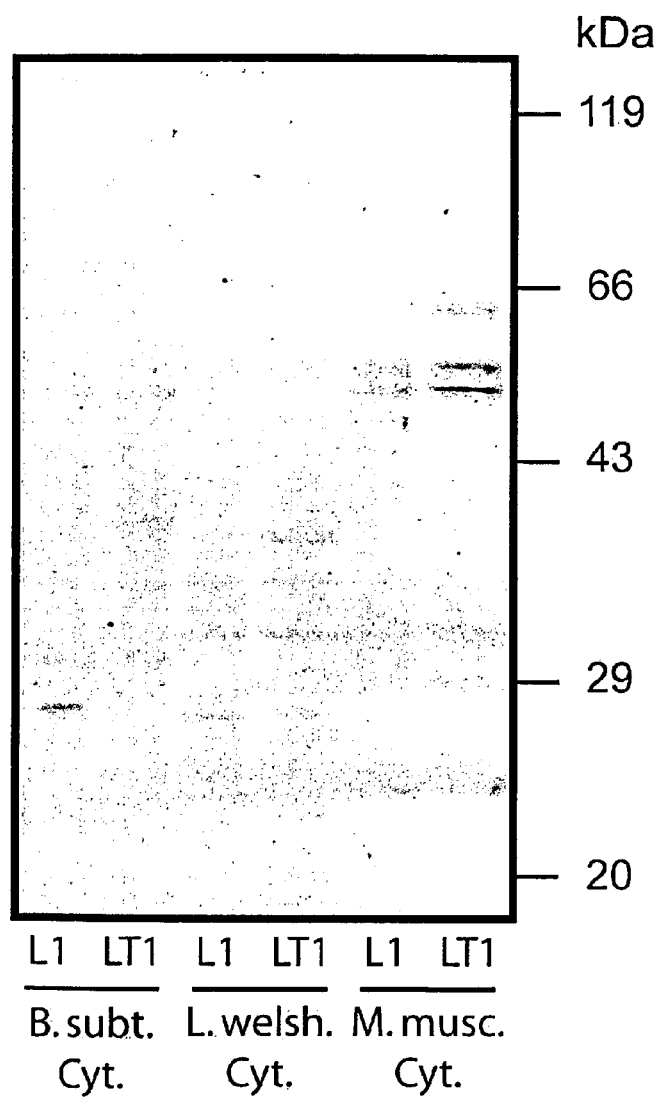

FIG. 15: Comparison of the cis and trans-beta-lactones L1 (cis) and LT1 (trans), respectively, reveals similar labeling profiles.

Figure 16:
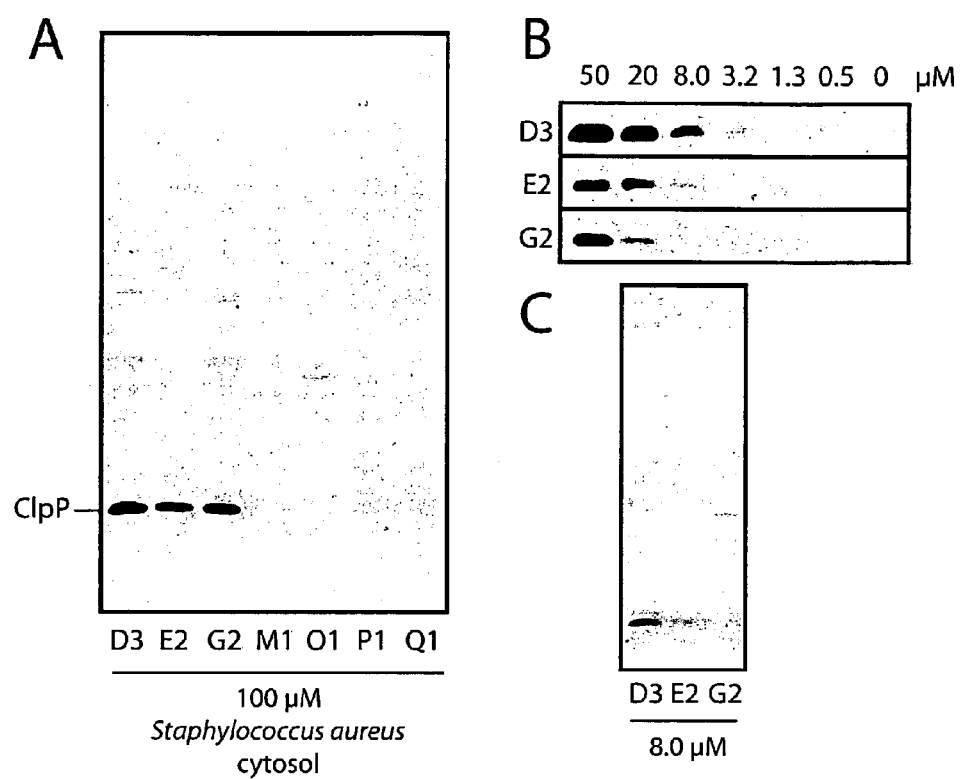

FIG. 16: In vivo labelling of the proteome of S. aureus with beta-lactones. Probes were applied at a certain concentration to approx. $2 \times 10^9$ cfu of stationary phase *S. aureus* in 100 μL PBS and incubated for 2 h. Excess probe (beta-lactone) was removed by washing the cells 3× with 1 mL PBS each. Then the cells were lysed by sonication. A) Fluorescent gel of *S. aureus* cytosol after treatment with selected beta-lactones as shown in FIG. 2. ClpP has been identified by mass spectrometry from preparative SDS gels after workup and tryptic digestion. B) In vivo dose down of beta-lactones D3, E2 and G2 with *S. aureus* indicates strong labeling by beta-lactone D3. C) Increase of selectivity at 8.0 μM concentration. ClpP is still labeled by D3 but almost no off-targets are visible at this concentration.

Figure 17:
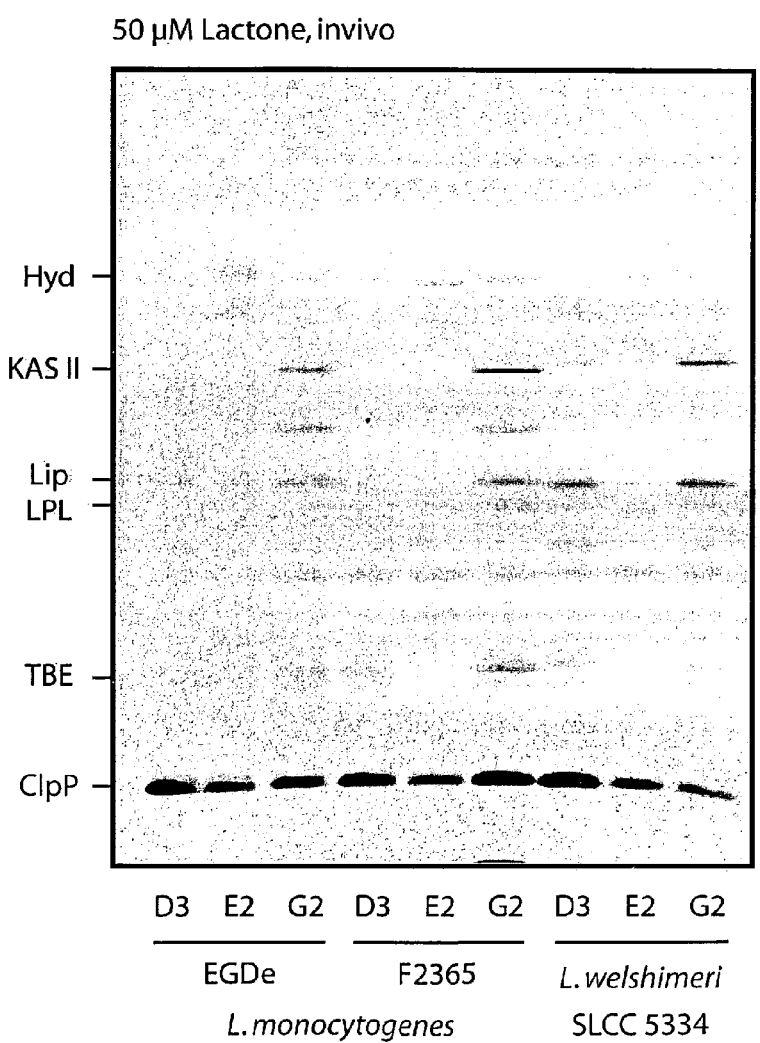

FIG. 17: Comparison of the activity-based protein profiling (ABPP) labeling profiles of *Listeria monocytogenes* strains EGDe and F2365 with *Listeria welshimeri* in living cells with 50 μM beta-lactone probes (as shown in FIGS. 2) and 2 h incubation. ClpP is the main target of these beta-lactones. Furthermore, Hydrolase CocE/NonD (Hyd), β-Ketoacyl acyl carrier protein synthase II (KAS II), Lipase (Lip), Lysophospholipase (LPL) and Tributyrin esterase (TBE) are identified as additional targets.

Figure 18:
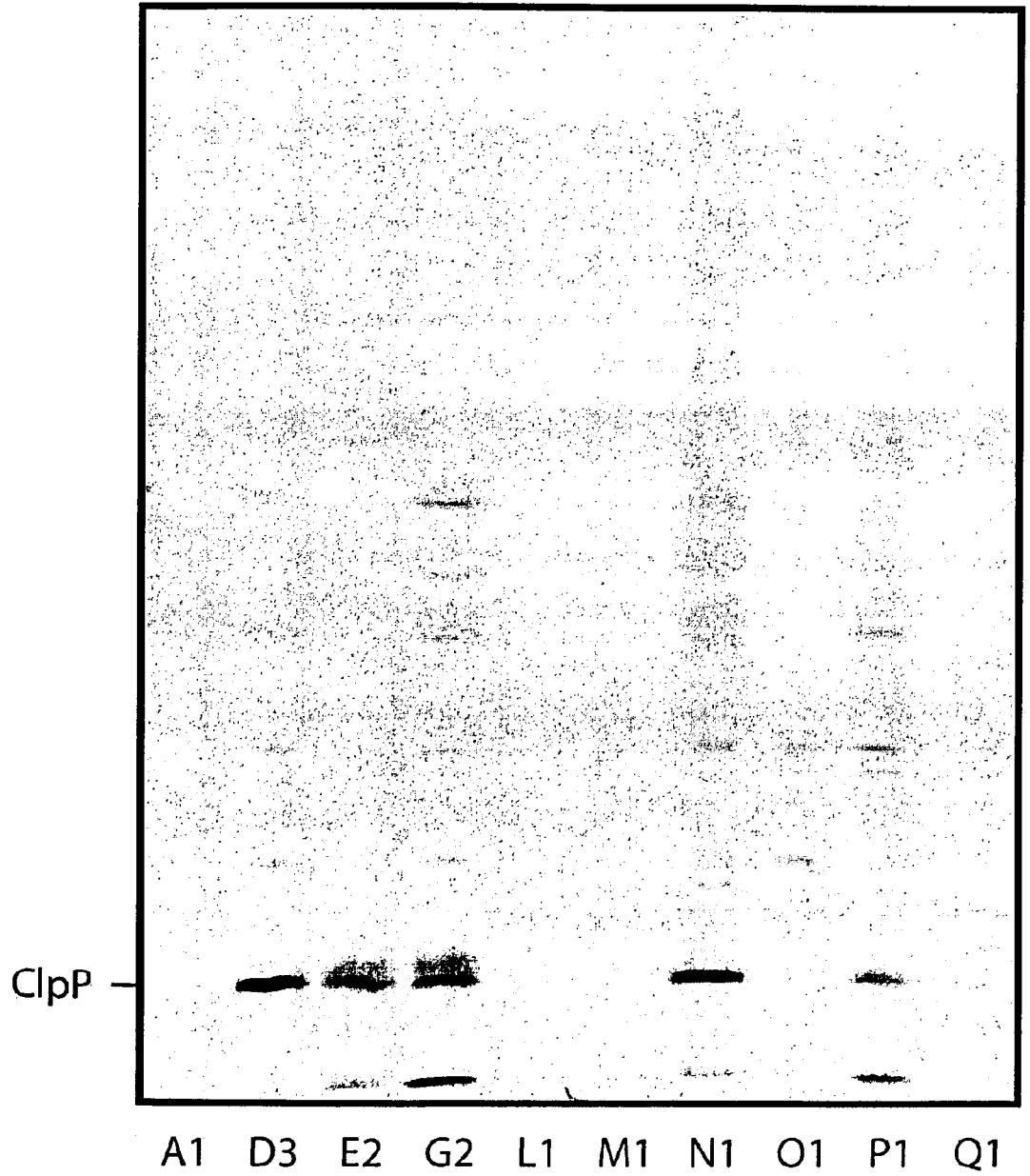

FIG. 18: Labeling profile of living *Listeria monocytogenes* EGDe with the beta-lactones as shown in FIG. 2 in the cytosol. ClpP is targeted mainly by beta-lactone probes D3 and N1, followed by G2 and E2.

Figure 19:
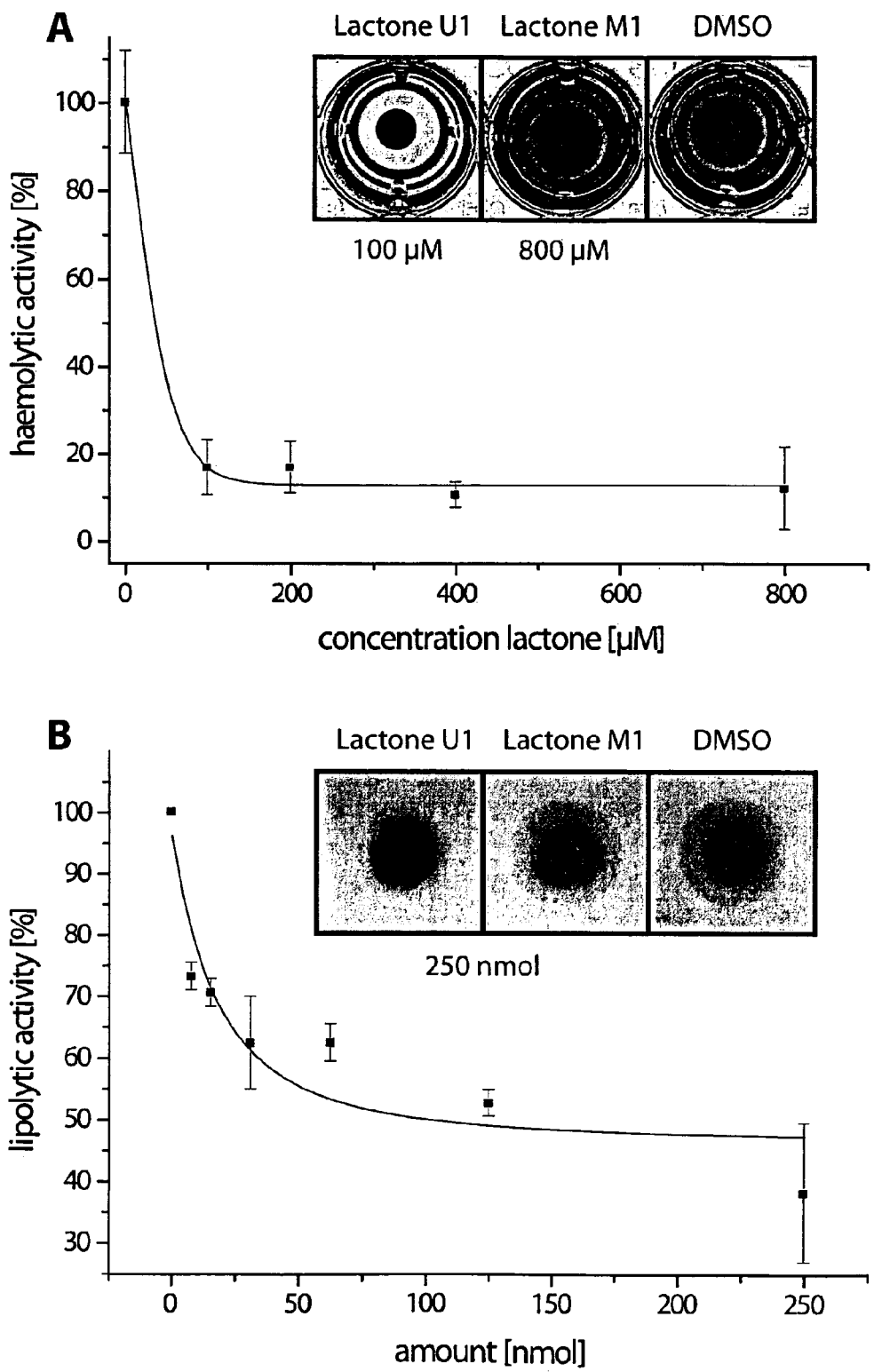

FIG. 19: Reduction of extracellular haemolytic and lipolytic activities of *Listeria monocytogenes* EGDe. A) LLO haemolytic activity of *L. monocytogenes* EGDe is strongly impaired for cultures grown in the presence of beta-lactone compound U1 with an $EC_{50}<100$ μM. A comparison of haemolytic activity of culture supernatants at fourfold dilution of *Listeria* grown with U1, M1 or DMSO. Low LLO levels are indicated by sedimented intact blood cells for U1, while the control lactone M1 (even at 800 μM) and the DMSO control sample exhibit complete lysis of blood cells. B) U1 treatment in Listeria detection agar plate-based assays results in a lowered PI-PLC activity of up to 50%.

Figure 20:
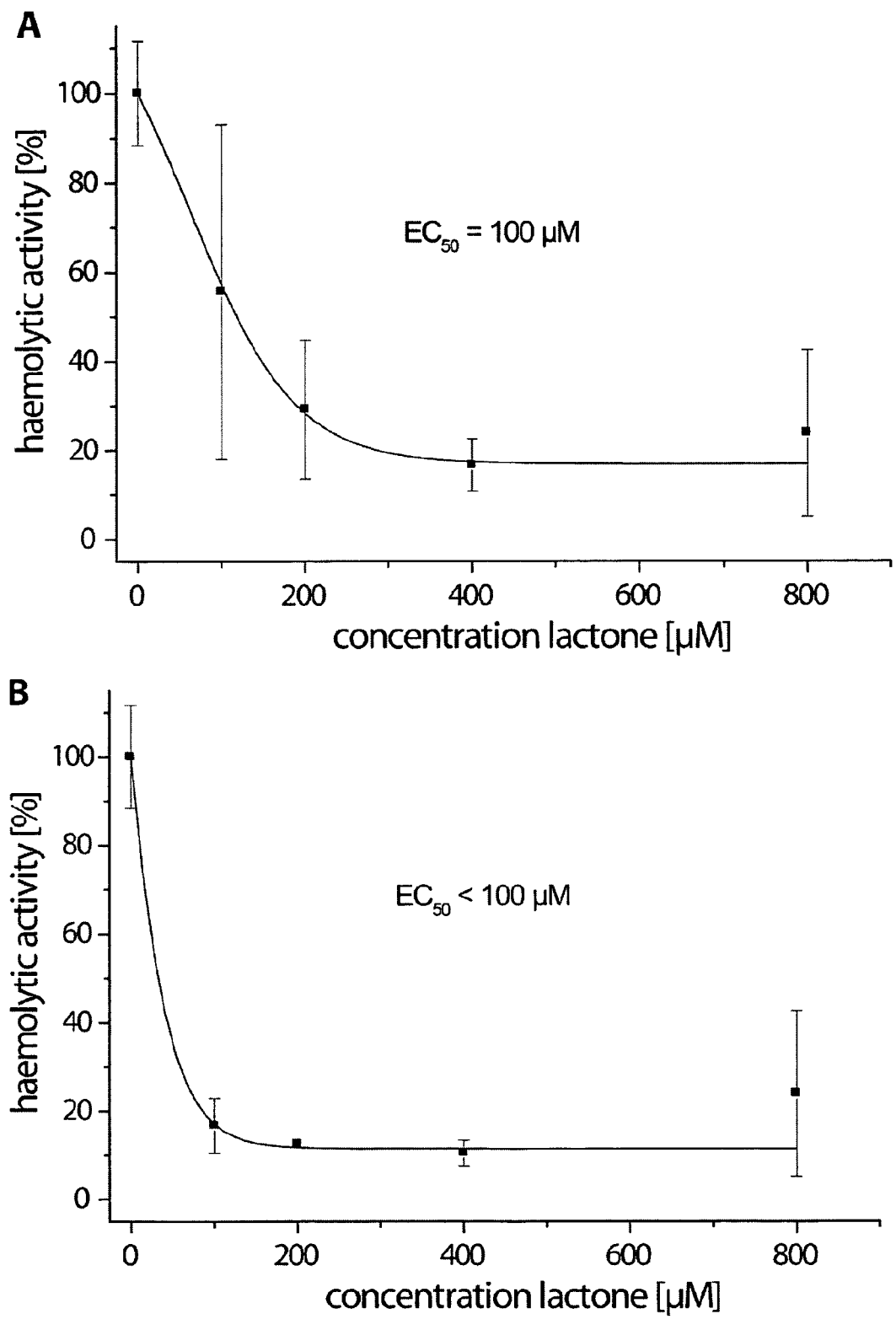

FIG. 20: LLO activity assay using the haemoylsis of sheep red blood cells of culture supernatants from *Listeria monocytogenes* EGDe grown at different lactone concentrations, A) with beta-lactone compound D3 or B) with beta-lactone compound N1.

Figure 21:
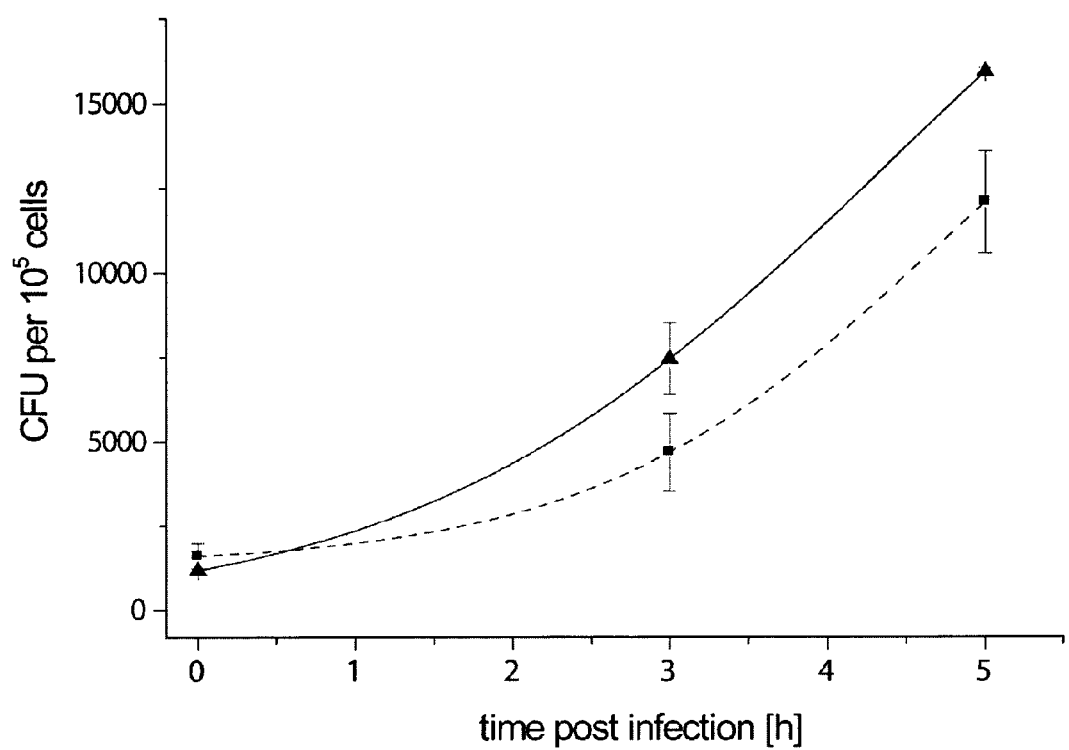

FIG. 21: Intracellular replication of *Listeria monocytogenes* EGDe in the mouse macrophage-like cell line J774 in colony forming units (CFU) per $10^5$ cells. The growth of bacteria treated with beta-lactone compound U1 (squares, dotted line) is significantly reduced compared to the control group with DMSO (pyramids, compact line).

EXAMPLES

Example 1

Synthesis

Materials

All chemicals were of reagent grade or better and used without further purification. Chemicals and solvents were purchased from Sigma Aldrich or Acros Organics. For all reactions, only commercially available solvents of purissimum grade, dried over molecular sieve and stored under Argon atmosphere were used. Solvents for chromatography and workup purposes were generally of reagent grade and purified before use by distillation. In all reactions, temperatures were measured externally. All experiments were carried out under nitrogen.

Column chromatography was performed on Merck silica gel (Acros Organics 0.035-0.070 mm, mesh 60 Å).

$^1$H NMR spectra were recorded on a Varian Mercury 200 (200 MHz), a Varian NMR-System 600 (600 MHz) or a Varian NMR-System 300 (300 MHz) and $^{13}$C NMR spectra were measured with a Varian NMR-System 600 (600 MHz) and a Varian NMR-System 300 (300 MHz) and referenced to the residual proton and carbon signal of the deuterated solvent, respectively.

Mass spectra were obtained by GC-MS with a Varian 3400 gas chromatograph via a 25 m CS Supreme-5 capillary column (Ø 0.25 mm, layer 0.25 μm) with a gradient of 50° C. (1 min isotherm) to 300° C. (4 min isotherm), 25° C. min$^{-1}$ coupled with a Finnigan MAT 95 mass spectrometer in EI mode (70 eV, 250° C. source). For DEI measurements, samples were directly desorbed from platinum wire (20-1600° C., 120° C. min$^{-1}$). ESI spectra were recorded with a Thermo Finnigan LTQ FT. HPLC analysis was accomplished with a Waters 2695 separations module, a X-Bridge™ BEH130 C18 column (4.6×100 mm) and a Waters 2996 PDA detector. Mobile phase (HPLC grade): A=water, 0.1% (v/v) TFA, B=acetonitril, 0.1% (v/v) TFA. Gradient: $T_0$: A=100%; $T_{25}$: A=5%; $T_{29}$: A=5%; $T_{37}$: A=100%; $T_{40}$: A=100%.

Synthesis of β-lactones

The C-3 unsubstitued β-lactone A1 (reference compound) was prepared by a $Al(SbF_6)_3$ catalyzed [2+2] cycloaddition of a ketene generated in situ from acetyl chloride with an aldehyde according to Nelson (Nelson, Tetrahedron Letters (1999), 6535)).

All other β-lactones of the library were synthesized according to a method developed by Danheiser and Nowick, (Danhaiser, J. Org. Chem. 56, (1991), 1176) as illustrated for 5-hexynal and a suitably functionalized S-phenyl thioate in FIG. 1 (Danhaiser, loc. cit.)

5-Hexynal (1)

A 25-mL, one-necked, round-bottomed flask was charged with a solution of Dess-Martin periodinane, DMP (848 mg, 2.0 mmol) in 10 mL of dichloromethane and then cooled in an ice bath while 5-hexyn-1-ol (217 μL, 2.0 mmol) was added dropwise over 1 min. The reaction was stirred for 5 min at 0° C. and after stirring additionally 3 h at room temperature the reaction was completed as monitored by TLC (n-pentane/diethyl ether 10:1; $R_f$=0.39) Thereafter the suspension was transferred with 10 mL diethyl ether to a 50-mL falcon tube and centrifuged (4000 rpm; 10 min). The supernatant was collected by decantation and the residual pellet was washed with 20 mL diethyl ether. The combined organic solutions were concentrated under reduced pressure on a rotary evaporator (40° C., >600 mbar). The mixture was purified by flash column chromatography on silica gel (n-pentane/diethyl ether 10:1). Evaporation of the solvent afforded 105 mg (55%) aldehyde 1 as colourless liquid.

$^1$H NMR (200 MHz, $CDCl_3$) δ 9.80 (t, J=1.3 Hz, 1 H, —CHO), 2.60 (dt, J=7.2, 1.3 Hz, 2 H, $CH_2$—CHO), 2.26 (dt, J=6.8, 2.7 Hz, 2 H, HC≡C—$CH_2$), 1.97 (t, J=2.6 Hz, 1 H, HC≡C), 1.84 (quint., J=6.8 Hz, 2 H, $CH_2$—$CH_2$—CHO).
GC RT=2.2 min, TIC-MS (m/z): 95.0485 [M—H]$^+$, Calc.: 95.0497.

General Procedure for the Preparation of S-phenyl Thioates from Acyl Chlorides

Preparation of S-phenyl 10-undecenethioate (2)

A 50-mL, one-necked, round-bottomed flask was charged with 10 mL toluene, triethylamine (0.70 mL, 5.0 mmol) and thiophenol (0.51 mL, 5.0 mmol). A solution of 10-undecenoyl chloride (1.10 mL, 5.1 mmol) in 15 mL toluene was added by a pressure-equalizing dropping funnel over 30 min while stirring the solution with a magnetic stirrer.

Precipitating triethylammonium chloride made the reaction mixture turn to a turbid suspension. After 10 min of additional stirring the reaction was completed as monitored by TLC (iso-hexane/ethyl acetate 25:1, $R_f$=0.43).

The organic mixture was washed twice with 25 mL saturated sodium hydrogen carbonate solution and once with 25 mL brine. The organic layer was dried over anhydrous $MgSO_4$, filtered and the solvent evaporated in vacuo to yield 1.27 g (92%) S-phenyl 10-undecenethioate 2 as pale yellow oil.

$^1$H NMR (300 MHz, $CDCl_3$) δ 7.43 (app. S, 5 H, $C_6H_5$), 5.83 (tdd, J=16.9, 10.2, 6.7 Hz, 1 H, CH=$CH_2$), 5.05-4.93 (m, 2 H, CH=$CH_2$), 2.67 (t, J=7.5 Hz, 2 H, C(O)—$CH_2$), 2.09-1.99 (m, 2H, $CH_2$—CH=$CH_2$), 1.73 (quint., J=7.5 Hz, 2 H, $CH_2$—$CH_2$—C(O)), 1.44-1.29 (m, 10 H, $(CH_2)_5$).
$^{13}$C NMR (151 MHz, $CDCl_3$) δ 197.8, 139.4, 134.7, 129.5, 129.4, 128.2, 114.4, 43.9, 34.0, 29.5, 29.4, 29.3, 29.2, 29.1, 25.8.

S-Phenyl 2-(4-methoxyphenyl)ethanethioate (3)

2-(4-Methoxyphenyl)acetyl chloride (3.06 mL, 20.0 mmol) in 60 mL toluene was added to a solution of triethylamine (2.80 mL, 20.1 mmol) and thiophenol (2.04 mL, 20.0 mmol) in 40 mL toluene. Reaction monitoring was accomplished by TLC: iso-hexane/ethyl acetate 25:1, $R_f$=0.29. Workup yielded 4.99 g (97%) S-phenyl 2-(4-methoxyphenyl) ethanethioate 3 as crystalline yellow solid.

$^1$H NMR (300 MHz, $CDCl_3$) δ 7.40 (app. s, 5 H, $C_6H_5$), 7.27 (d, J=7.3 Hz, 2 H, phenylene C—H), 6.91 (d, J=8.7 Hz, 2 H, phenylene C—H), 3.87 (s, 2 H, C(O)—$CH_2$), 3.83 (s, 3 H, O—$CH_3$).
$^{13}$C NMR (151 MHz, $CDCl_3$) δ 196.1, 159.3, 134.7, 131.0, 129.6, 129.3, 128.1, 125.5, 114.4, 55.5, 49.5.

S-Phenyl Hexanethioate (4)

Hexanoyl chloride (2.76 mL, 19.7 mmol) in 60 mL toluene was added to a solution of triethylamine (2.80 mL, 20.1 mmol) and thiophenol (2.04 mL, 20.0 mmol) in 40 mL toluene. Reaction monitoring was accomplished by TLC: iso-hexane/ethyl acetate 100:1, $R_f$=0.20. Workup yielded 3.89 g (95%) S-phenyl hexanethioate 4 as pale yellow oil.

$^1$H NMR (300 MHz, $CDCl_3$) δ 7.41 (app. s, 5 H, $C_6H_5$), 2.66 (t, J=7.5 Hz, 2 H, C(O)—$CH_2$), 1.72 (quint., J=7.4 Hz, 2 H, C(O)—$CH_2$—$CH_2$), 1.39-1.31 (m, 4 H, $(CH_2)_2$—$CH_3$) 0.91 (t, J=7.1, 2 H, $CH_3$).
$^{13}$C NMR (75 MHz, $CDCl_3$) δ 197.8, 134.7, 129.5, 129.4, 128.2, 43.9, 31.4, 25.5, 22.6, 14.1.

S-Phenyl 3,3-dimethylbutanethioate (5)

3,3-Dimethylbutanoyl chloride (695 μL, 5.0 mmol) in 15 mL toluene was added to a solution of triethylamine (0.70 mL, 5.0 mmol) and thiophenol (0.51 mL, 5.0 mmol) in 10 mL toluene. Reaction monitoring was accomplished by TLC: iso-hexane/ethyl acetate 25:1, $R_f$=0.63. Workup yielded 941 mg (90%) S-phenyl 3,3-dimethylbutanethioate 5 as pale yellow oil.

$^1$H NMR (200 MHz, $CDCl_3$) δ 7.40 (app. s, 5 H, $C_6H_5$), 2.55 (s, 2 H, C(O)—$CH_2$), 1.08 (s, 9 H, $C(CH_3)_3$).
$^{13}$C NMR (75 MHz, $CDCl_3$) δ 196.1, 134.6, 129.5, 129.4, 128.7, 56.5, 32.1, 29.9.

S-Phenyl Isobutanethioate (6)

Isobutanoyl chloride (528 μL, 5.0 mmol) in 15 mL toluene was added to a solution of triethylamine (0.70 mL, 5.0 mmol) and thiophenol (0.51 mL, 5.0 mmol) in 10 mL toluene. Reaction monitoring was accomplished by TLC: iso-hexane/ethyl acetate 25:1; $R_f$=0.47. Workup yielded 653 mg (72%) S-phenyl isobutanethioate 6 as pale yellow oil.

$^1$H NMR (200 MHz, $CDCl_3$) δ 7.40 (app. s, 5 H, $C_6H_5$), 2.87 (sept., J=6.9 Hz, 1 H, $CH(CH_3)_2$), 1.27 (d, J=6.9 Hz, 6 H, $CH(CH_3)_2$).
$^{13}$C NMR (600 MHz, $CDCl_3$) δ 202.1, 134.8, 129.4, 129.3, 128.1, 43.2, 19.6.

S-Phenyl Decanedithioate (7)

Sebacoyl chloride (267 µL, 1.25 mmol) in 7.5 mL toluene was added to a solution of triethylamine (350 µL, 2.5 mmol) and thiophenol (255 µL, 2.5 mmol) in 5 mL toluene. Reaction monitoring was accomplished by TLC: iso-hexane/ethyl acetate 25:1, $R_f$=0.19. Workup yielded 492 mg (98%) S-phenyl decanedithioate 7 as colourless solid.

$^1$H NMR (75 MHz, CDCl$_3$) δ 7.41 (app. s, 10 H, (C$_6$H$_5$)$_2$), 2.65 (t, J=7.4 Hz, 4 H, 2 x C(O)—CH$_2$), 1.71 (quint., J=7.2 Hz, 4 H, 2 x C(O)—CH$_2$—CH$_2$), 1.45-1.26 (m, 8 H, (CH$_2$)$_4$).
$^{13}$C NMR (75 MHz, CDCl$_3$) δ 197.7, 134.7, 129.5, 129.4, 128.2, 43.9, 29.2, 29.1, 25.8.

S-Phenyl Cyclohexanecarbothioate (8)

Cyclohexanecarbonyl chloride (669 µL, 5.0 mmol) in 15 mL toluene was added to a solution of triethylamine (0.70 mL, 5.0 mmol) and thiophenol (0.51 mL, 5.0 mmol) in 10 mL toluene. Reaction monitoring was accomplished by TLC: iso-hexane/ethyl acetate 25:1, $R_f$=0.45. Workup yielded 1016 mg (92%) S-phenyl cyclohexanecarbothioate 8 as crystalline colourless solid.

$^1$H NMR (300 MHz, CDCl$_3$) δ 7.42 (app. s, 5 H, C$_6$H$_5$), 2.63 (tt, J=11.4, 3.6 Hz, 1 H, CH—C(O)), 2.05-1.19 (m, 10 H, (CH$_2$)$_5$).
$^{13}$C NMR (75 MHz, CDCl$_3$) δ 201.0, 134.8, 129.4, 129.3, 128.2, 52.7, 29.8, 25.8, 25.7.

S-Phenyl 2-(2-naphthyl)ethanethioate (9)

2-(2-Naphthyl)acetyl chloride (308 mg, 1.5 mmol) in 4.5 mL toluene was added to a solution of triethylamine (0.21 mL, 1.5 mmol) and thiophenol (153 µL, 1.5 mmol) in 3 mL toluene. Reaction monitoring was accomplished by TLC: iso-hexane/ethyl acetate 25:1, $R_f$=0.33. Workup yielded 376 mg (90%) S-phenyl 2-(2-naphthyl)ethanethioate 9 as yellow solid.

$^1$H NMR (200 MHz, CDCl$_3$) δ 7.88-7.80 (m, 4 H, naphthyl C—H), 7.54-7.44 (m, 3 H, naphthyl C—H), 7.39 (app. s, 5 H, C$_6$H$_5$), 4.09 (s, 2 H, C(O)—CH$_2$)
$^{13}$C NMR (75 MHz, CDCl$_3$) δ 195.6, 134.7, 133.7, 132.9, 131.0, 129.7, 129.4, 128.9, 128.7, 128.0, 127.9, 127.8, 127.7, 126.5, 126.3, 50.6.

S-Phenyl 2-(3,4,5-trimethoxyphenyl)ethanethioate (10)

A 10-mL, one-necked, round-bottomed flask was charged with 2.5 mL dichloromethane, (3,4,5-trimethoxyphenyl)acetic acid (566 mg, 2.5 mmol), DMAP (31 mg, 2.5 mmol) and thiophenol (1.0 mL, 9.9 mmol). The mixture was cooled in an ice bath while DCC (619 mg, 3.0 mmol) was added and stirred for 5 min. The reaction was allowed to warm up to room temperature and additionally stirred for 3 h.

After stirring, the resulting suspension was filtrated and the organic solution diluted with dichloromethane to a total volume of 30 mL. The organic mixture was washed twice with 30 mL 0.5 M HCl and once with 30 mL saturated sodium hydrogen carbonate solution. The organic layer was dried over anhydrous MgSO$_4$, filtered and the solvent evaporated in vacuo. The crude product was purified by column chromatography on silica gel (iso-hexane/ethyl acetate 50:11, $R_f$=0.48). Evaporation of the solvent yielded 483.5 mg (61%) S-phenyl 2-(3,4,5-trimethoxyphenyl)ethanethioate 10 as white solid.

$^1$H NMR (200 MHz, CDCl$_3$) δ 7.40 (app. s, 5 H, C$_6$H$_5$), 6.54 (s, 2H, phenylene C—H), 3.87 (s, 6H, 2 x CH$_3$), 3.5 (m, 5 H, CH$_3$, CH$_2$).
$^{13}$C NMR (151 MHz, CDCl$_3$) δ 195.5, 153.6, 137.7, 134.6, 129.7, 129.4, 129.0, 127.9, 106.9, 61.1, 56.4, 50.5.

4-(4-Pentyn-1-yl)oxetan-2-one (lactone A1; reference compound)

A 10-mL, one-necked, round-bottomed flask was charged with 600 µL dichloromethane, anhydrous AlCl$_3$ (10.6 mg, 0.08 mmol) and cooled to −30° C. in a water-isopropanol-dry ice bath. Then, diisopropylethylamine (41.8 µL, 0.24 mmol) and a pre-cooled solution of AgSbF$_6$ (82.4 mg, 0.24 mmol) in 600 µL dichloromethane were added followed by diisopropylethylamine (69.8 µL, 0.40 mmol), acetyl chloride (42.6 µL, 0.60 mmol) and 5-hexynal 1 (38.4 mg, 0.40 mmol).

The reaction was complete after stirring for 2.5 h as monitored by TLC (iso-hexane/ethyl acetate 5:1; $R_f$=0.23). The mixture was filtered, concentrated in vacuo and the product purified by flash column chromatography on silica gel (iso-hexane/ethyl acetate 5:1) to yield 15.6 mg (28%) 4-(4-pentyn-1-yl)oxetan-2-one A1 as colourless oil.

$^1$H NMR (200 MHz, CDCl$_3$) δ 4.60-4.49 (m, 1 H, H-4), 3.54 (dd, J=16.3, 5.8 Hz, 1 H, H-3), 3.10 (dd, J=16.3, 4.3 Hz, 1 H, H-3), 2.28 (dt, J=6.8, 2.7 Hz, 2 H, HC≡C—CH$_2$), 1.99 (t, J=2.6 Hz, 1 H, HC≡C), 1.97-1.57 (m, 4 H, CH$_2$—CH$_2$—CH).
GC RT=5.1 min, EI-MS (m/z): 137.0612 [M−H]$^+$, Calc.: 137.0603.

General procedure for the preparation of 2-oxetanones from S-phenyl thioates

Preparation of trans-3-(8-nonen-1-yl)-4-(4-pentyn-1-yl)oxetan-2-one (lactone D3)

A 10-mL, three-necked, round-bottomed flask equipped with a rubber septum, an nitrogen inlet adapter and a glass stopper was charged with 2 mL THF and diisopropylamine (36.5 µL, 0.26 mmol) and then cooled in an ice bath while n-butyllithium (96.0 µL of a 2.5 M solution in hexanes, 0.24 mmol) was injected via a syringe into the reaction mixture over 2 min. The mixture was stirred for 20 min by a magnetic stirrer at 0° C.

Thereafter the ice bath was replaced with an acetone-dry ice bath and the reaction mixture was cooled to −78° C. A solution of S-phenyl 10-undecenethioate 2 (55.3 mg, 0.20 mmol) in 250 THF was added dropwise via a syringe over 5 min. After stirring the mixture for 2 h at −78° C., a solution of 5-hexynal 1 (19.2 mg, 0.20 mmol) in 250 µL THF was added dropwise over 25 min via a syringe which was cooled externally by a rubber tube filled with dry ice. The reaction mixture was stirred for 30 min and then gradually warmed up to 0° C. within 75 min. Then 1 mL half-saturated NH$_4$Cl solution was added.

The mixture was diluted with 30 mL diethyl ether and washed twice with 30 mL 10% K$_2$CO$_3$ solution and once with 30 mL brine. The aqueous layers were re-extracted with 30 mL diethyl ether and the combined organic layers dried over MgSO$_4$, filtered and concentrated in vacuo. The product was purified by column chromatography on silica gel according to TLC optimized solvent mixing ratios: iso-hexane/ethyl acetate 50:3, $R_f$=0.31. 3.9 mg (7%) trans-3-(8-nonen-1-yl)-4-(4-pentyn-1-yl)oxetan-2-one D3 was obtained as pale yellow oil.

¹H NMR (200 MHz, CDCl₃) δ 5.80 (tdd, J=16.9, 10.1, 6.7 Hz, 1 H, C$\underline{H}$=CH₂), 5.04-4.89 (m, 2H, CH=C$\underline{H}_2$), 4.24 (dt, J=6.5, 3.9 Hz, 1 H, H-4), 3.20 (ddd, J=8.7, 6.8, 4.2 Hz, 1 H, H-3), 2.28 (dt, J=6.9, 2.6 Hz, 2 H, HC≡C—C$\underline{H}_2$), 1.99 (t, J=2.6 Hz, 1 H, $\underline{H}$C≡C), 2.05-1.31 (m, 18 H, (C$\underline{H}_2$)₂ and (C$\underline{H}_2$)₇).

GC RT=9.0 min, DEI-MS (m/z): 262.1929 [M]⁺, Calc.: 262.1933.

trans-3-(4-methoxyphenyl)-4-(4-pentyn-1-yl)oxetan-2-one (lactone E2)

The reaction was performed with S-phenyl 2-(4-methoxyphenyl)ethanethioate 3 (51.7 mg, 0.20 mmol). Standard workup and purification by flash column chromatography (iso-hexane/ethyl acetate 5:1, $R_f$=0.35) yielded 6.3 mg (13%) trans-3-(4-methoxyphenyl)-4-(4-pentyn-1-yl)oxetan-2-one E2 as pale yellow oil.

¹H NMR (200 MHz, CDCl₃) δ 7.19 (d, J=8.5 Hz, 2 H, phenylene C—$\underline{H}$), 6.91 (d, J=8.7 Hz, 2H, phenylene C—$\underline{H}$), 4.51 (dt, J=6.6, 4.3 Hz, 1 H, H-4), 4.38 (d, J=4.3 Hz, 1H, H-3), 3.81 (s, 3 H, O—C$\underline{H}_3$), 2.29 (dt, J=6.8, 2.7 Hz, 2 H, HC≡C—C$\underline{H}_2$), 2.17-2.04 (m, 2 H, C$\underline{H}_2$), 2.00 (t, J=2.6 Hz, 1 H, $\underline{H}$C≡C), 1.87-1.55 (m, 2 H, C$\underline{H}_2$).

GC RT=8.0 min, DEI-MS (m/z): 244.1090 [M]⁺, Calc.: 244.1099.

trans-3-butyl-4-(4-pentyn-1-yl)oxetan-2-one (lactone G2)

The reaction was performed with S-phenyl hexanethioate 4 (41.7 mg, 0.20 mmol). Standard workup and purification by flash column chromatography (iso-hexane/ethyl acetate 25:1, $R_f$=0.19) yielded 4.8 mg (12%) trans-3-butyl-4-(4-pentyn-1-yl)oxetan-2-one G2 as pale yellow oil.

¹H NMR (200 MHz, CDCl₃) δ 4.25 (dt, J=6.5, 4.0 Hz, 1 H, H-4), 3.19 (ddd, J=8.6, 6.6, 4.0 Hz, 1 H, H-3), 2.28 (dt, J=6.9, 2.6 Hz, 2 H, HC≡C—C$\underline{H}_2$), 1.99 (t, J=2.7 Hz, 1 H, HC≡C), 1.82-1.16 (m, 10H, (C$\underline{H}_2$)₃ and (C$\underline{H}_2$)₂), 0.92 (t, J=6.7 Hz, 3 H, C$\underline{H}_3$).

GC RT=6.7 min, TIC-MS (m/z): 193.1235 [M–H]⁺, Calc.: 193.1229.

cis- and trans-3-dimethylethyl-4-(4-pentyn-1-yl)oxetan-2-one (lactone L1 (cis-form) and LT1 (trans-form))

The reaction was performed with S-phenyl 3,3-dimethylbutanethioate 5 (41.7 mg, 0.20 mmol). Standard workup and purification by flash column chromatography (iso-hexane/ethyl acetate 25:1, $R_f^{cis}$=0.22, $R_f^{trans}$=0.28) yielded 6.9 mg (17%) cis-3-dimethylethyl-4-(4-pentyn-1-yl)oxetan-2-one L1 and 2.1 mg (5%) trans-3-dimethylethyl-4-(4-pentyn-1-yl)oxetan-2-one LT1 as pale yellow oil.

For the cis isomer L1:

¹H NMR (200 MHz, CDCl₃) δ 4.55 (dd, J=13.6, 6.8 Hz, 1 H, H-4), 3.56 (d, J=6.8 Hz, 1 H, H-3), 2.34-2.25 (m, 2 H, HC≡C—C$\underline{H}_2$), 2.13-2.02 (m, 2H, C$\underline{H}_2$), 1.98 (t, J=2.7 Hz, 1 H, HC≡C), 1.93-1.52 (m, 2H, C$\underline{H}_2$), 1.14 (s, 9 H, C(C$\underline{H}_3$)₃).

GC RT=6.4 min, TIC-MS (m/z): 193.1224 [M–H]⁺, Calc.: 193.1229.

For the trans isomer LT1:

¹H NMR (600 MHz, CDCl₃) δ 4.34 (dt, J=7.8, 4.8 Hz, 1 H, H-4), 3.04 (d, J=4.1 Hz, 1 H, H-3), 2.29 (m, 2 H, HC≡C—C$\underline{H}_2$), 1.99 (t, J=2.6 Hz, 1 H, HC≡C), 1.96-1.85 (m, 2H, C$\underline{H}_2$), 1.75-1.59 (m, 2H, C$\underline{H}_2$), 1.06 (s, 9 H, C(C$\underline{H}_3$)₃).

GC RT=7.0 min, TIC-MS (m/z): 193.1205 [M–H]⁺, Calc.: 193.1229.

¹³C NMR (151 MHz, CDCl₃) δ 170.4, 83.5, 74.1, 69.5, 67.6, 34.0, 30.9, 27.4, 24.4, 18.3.

trans-3,3-dimethyl-4-(4-pentyn-1-yl)oxetan-2-one (lactone M1; reference compound).

The reaction was performed with S-phenyl isobutanethioate 6 (36 mg, 0.20 mmol). Standard workup and purification by flash column chromatography (iso-hexane/ethyl acetate 50:3, $R_f$=0.21) yielded 11.3 mg (34%) trans-3,3-dimethyl-4-(4-pentyn-1-yl)oxetan-2-one M1 as pale yellow oil.

¹H NMR (200 MHz, CDCl₃) δ 4.24 (t, J=6.7 Hz, 1 H, H-4), 2.33-2.24 (m, 2 H, HC≡C—C$\underline{H}_2$), 1.98 (t, J=2.7, 1 H, HC≡C), 1.90-1.49 (m, 4 H, (C$\underline{H}_2$)₂), 1.42 (s, 3 H, C$\underline{H}_3$), 1.27 (s, 3 H, C$\underline{H}_3$), GC RT=5.4 min, TIC-MS (m/z): 166.0977 [M–H]⁺, Calc.: 166.0994.

trans-S-phenyl 8-(2-oxo-4-(4-pentyn-1-yl)oxetan-3-yl)octanethioate (lactone N1)

The reaction was performed with S-phenyl decanedithioate 7 (38.7 mg, 0.20 mmol). Standard workup and purification by flash column chromatography (iso-hexane/ethyl acetate 25:3, $R_f$=0.30) yielded 4.0 mg (5%) trans-S-phenyl 8-(2-Oxo-4-(4-pentyn-1-yl)oxetan-3-yl)octanethioate N1 as pale yellow oil.

¹H NMR (200 MHz, CDCl₃) δ 7.41 (app. s, 5 H, C₆H₅), 4.25 (dt, J=6.5, 4.0 Hz, 1 H, H-4), 3.20 (ddd, J=8.5, 6.8, 3.9 Hz, 1 H, H-3), 2.65 (t, J=7.4 Hz, 2 H, C(O)—C$\underline{H}_2$), 2.28 (dt, J=6.9, 2.6 Hz, 2 H, HC≡C—C$\underline{H}_2$), 1.99 (t, J=2.7 Hz, 1 H, HC≡C), 1.95-1.28 (m, 16 H, (C$\underline{H}_2$)₂ and (CH₂)₆).

HPLC RT (254 nm)=27.05 min, ESI-MS (m/z): 373.1826 [M+H]⁺, Calc.: 373.1837.

4-(4-Pentyn-1-yl)oxetan-2-one-3-spirocyclohexane (lactone O1; reference compound)

The reaction was performed with S-phenyl cyclohexanecarbothioate 8 (44.1 mg, 0.20 mmol). Standard workup and purification by flash column chromatography (iso-hexane/ethyl acetate 20:1, $R_f$=0.28) yielded 10.1 mg (24%) 4-(4-pentyn-1-yl)oxetan-2-one-3-spirocyclohexane O1 as pale yellow oil.

¹H NMR (600 MHz, CDCl₃) δ 4.16 (dd, J=9.8, 3.7 Hz, 1 H, H-4), 2.34-2.23 (m, 2H, HC≡C—C$\underline{H}_2$), 1.98 (t, J=2.6 Hz, 1 H, HC≡C), 1.94-1.33 (m, 11H, CH and (CH₂)₅).

¹³C NMR (151 MHz, CDCl₃) δ 174.9, 83.6, 82.9, 69.4, 58.3, 33.3, 29.1, 26.7, 25.5, 24.7, 23.0, 22.8, 18.3.

GC RT=7.5 min, TIC-MS (m/z): 205.1222 [M–H]⁺, Calc.: 205.1229.

trans-3-(2-naphthyl)-4-(4-pentyn-1-yl)oxetan-2-one (lactone P1; reference compound)

The reaction was performed with S-phenyl 2-(2-naphthyl)ethanethioate 9 (111.4 mg, 0.40 mmol). All reagents and solvents were scaled up accordingly. Standard workup and purification by flash column chromatography (iso-hexane/ethyl acetate 100:11, $R_f$=0.34) yielded 6.8 mg (6%) trans-3-(2-naphthyl)-4-(4-pentyn-1-yl)oxetan-2-one P1 as pale yellow oil.

¹H NMR (600 MHz, CDCl₃) δ 7.88 (d, J=8.5 Hz, 1 H, naphthyl C—$\underline{H}$), 7.85-7.82 (m, 2 H, naphthyl C—$\underline{H}$), 7.76 (s, 1 H, naphthyl C—$\underline{H}$), 7.53-7.49 (m, 2 H, naphthyl C—$\underline{H}$)

7.36 (dd, J=8.4, 1.8 Hz, 1 H, naphthyl C—H), 4.66 (dt, J=6.6, 4.3, 1 H, H-4), 4.61 (d, J=4.3 Hz, 1 H, H-3), 2.32 (dt, J=7.0, 2.6 Hz, 2 H, HC≡C—$CH_2$), 2.19-2.15 (m, 2 H, $CH_2$), 2.01 (t, J=2.6 Hz, 1 H, HC≡C), 1.84-1.69 (m, 2 H, $CH_2$).

$^{13}$C NMR (151 MHz, $CDCl_3$) δ 169.2, 133.6, 133.1, 130.0, 129.5, 128.1, 128.0, 127.0, 126.8, 126.7, 124.8, 83.3, 79.5, 69.8, 61.8, 33.7, 24.2, 18.3.

HPLC RT (254 nm)=25.5 min, DEI-MS (m/z): 264.1160 $[M]^+$, Calc.: 264.1150.

trans-4-(4-pentyn-1-yl)-3-(3,4,5-trimethoxyphenyl)oxetan-2-one (lactone Q1)

The reaction was performed with S-phenyl 2-(3,4,5-trimethoxyphenyl)ethanethioate 10 (63.7 mg, 0.20 mmol). Standard workup and purification by flash column chromatography (iso-hexane/ethyl acetate 5:2, $R_f$=0.34) yielded 5.2 mg (9%) trans-4-(4-pentyn-1-yl)-3-(3,4,5-trimethoxyphenyl)oxetan-2-one Q1 as pale yellow oil.

$^1$H NMR (200 MHz, $CDCl_3$) δ 6.46 (s, 2 H, phenylene C—H), 4.55 (dt, J=6.6, 4.3, 1 H, H-4), 4.36 (d, J=4.3 Hz, 1 H, H-3), 3.86 (s, 6 H, 2 x $CH_3$), 3.83 (s, 3 H, $CH_3$), 2.31 (dt, J=6.8, 2.7 Hz, 2 H, HC≡C—$CH_2$), 2.17-2.06 (m, 2 H, $CH_2$), 2.01 (t, J=2.6 Hz, 1 H, HC≡C), 1.86-1.61 (m, 2 H, $CH_2$).

$^{13}$C NMR (151 MHz, $CDCl_3$) δ 169.2, 154.1, 138.3, 128.2, 104.6, 83.3, 79.4, 69.8, 61.8, 61.1, 56.5, 33.6, 24.2, 18.3.

GC RT=10.2 min, DEI-MS (m/z): 304.1295 $[M]^+$, Calc.: 304.1311.

HPLC RT (254 nm)=20.2 min.

Lactones R1, T1 and S1 (FIG. 2B) were synthesized accordingly, using appropriately adapted reactants.

Example 2

Haemolysis

This example relates to a blood agar plate-based assay which reveals the effects of β-lactones on the haemolysis abilities of *Staphylococcus aureus*. 2.5 μL of *S. aureus* LB dilution ($OD_{600}$=0.13 corresponding to approx. 1×10$^8$ cfu/ml) and 2.5 μL DMSO/beta-lactone in DMSO were applied on Whatman Cards placed on 5% sheep blood agar plates (Heipha Diagnostika, Eppelheim, Germany) and incubated at 37° C. over night. FIG. 3A directly compares the β-lactones at a total amount of 250 nmol applied on Whatman Cards. Beta-lactones D3 and E2 strongly reduce the haemolytic activity of *S. aureus*, while no effect could be observed for M1. FIG. 3B illustrates the dose down with beta-lactones D3, E2 and G2 at applied concentrations of 100 mM, 50 mM, 25 mM, 12.5 mM, 6.25 mM and 0 mM. For D3 almost no haemolysis is observed down to a total amount of 125 nmol lactone. FIG. 5 illustrates the haemolytic activity of beta-lactone compounds D3, E2 and G2 plotted against the total amount of the respective beta-lactone, whereby a haemolysis zone size of 1.5 mm was set as 100% haemolytic activity. The data shown in FIG. 5 has been corroborated by further experimental testing.

Example 3

Haemolysis

The example shows the effect of further compounds on the haemolysis abilities of *S. aureus,* including small and large alkyl (R1 and T1) and aromatic (U1) moieties as well as a Spiro compound (S1).

Biological Testing

Haemolysis was tested on blood agar plates (5% sheep blood; Heipha Diagnostika, Eppelheim, Germany). Sterile circles of Whatman cards (No. Y) with 5 mm diameter were placed on agar plates and inoculated with 2.5 μL of the corresponding beta-lactone/DMSO and 2.5 μL stationary phase culure of *S. aureus* diluted to $OD_{600}$=1.3. The plates were incubated over night at 37° C. and the diameters of the zones around the bacterial colonies were precisely measured using a vernier caliper.

The results shown in FIG. 4A indicate that the substituents in C-3 ($R^1$) and C-4 ($R^3$) position exhibit an influence on the inhibition of haemolysis. Large chains as well as phenyl substituents in position C-3 increase the inhibiting activity of the beta-lactones. On the other hand, a large chain size in position C-4 appears to be less favourable. An aralkyl group in this position gives rise to a increase in the inhibiting activity.

A dose down in FIG. 5 indicates the different potencies of structurally diverse ClpP inhibitors for E2, G2 and D3. Beta-lactone D3 is the biologically most active compound. Extracellular DNase also is part of the *S. aureus* virulence factors. Its purpose is to destroy the hosts DNA and provide a nutritional source for *S. aureus*. FIG. 4B shows that DNase as an additional virulence factor is lowered in the presence of ClpP inhibiting β-lactones.

Example 4

Proteolysis

This example relates to a milk agar plate-based assay which reveals the effects of β-lactones on the proteolysis abilities of *Staphylococcus aureus*. 2.5 μL of *S. aureus* LB dilution ($OD_{600}$=0.13 corresponding to approx. 1×10$^8$ cfu/ml) and 2.5 μL DMSO/beta-lactone in DMSO were applied on Whatman Cards placed on 1% skim milk LB agar plates and incubated at 37° C. over night. FIG. 6A directly compares the β-lactones at a total amount of 250 nmol applied on Whatman Cards. Beta-lactones D3 and E2 strongly reduce the proteolytic activity of *S. aureus*, and no effect could be observed for M1. FIG. 6B shows a dose down with beta-lactones D3, E2 and G2 at applied concentrations of 100 mM, 50 mM, 25 mM, 12.5 mM, 6.25 mM and 0 mM. For D3 and E2 almost no proteolysis is observed down to a total amount of 125 nmol of the respective beta-lactone. FIG. 6C illustrates that the proteolysis zone size plotted against the total amount of beta-lactone visualizes the strong effects particularly of D3 and E2.

Example 5

Sequence Alignment

Amino acid sequences of ATP-dependent Clp protease (proteolytic subunit ClpP) from *Staphylococcus aureus* subsp. aureus NCTC 8325 (Sequence 1B), from *Staphylococcus epidermis* ATCC 12228 (Sequence 2B), from Listeria welshimeri serovar 6b str. SLCC5334 (Sequence 3B) and from Listeria monocytogenes str. 4b F2365 (Sequence 4B) were aligned in order to investigate the sequence similarities of Clp proteases of diverse bacterial strains.

The alignments show a sequence identity in respect of Clp from *Staphylococcus aureus* subsp. *aureus* NCTC 8325 and Clp from *Listeria monocytogenes* str. 4b F2365 (L.) of 79.1% (Sequence Alignment 1). The sequence alignments in respect of Clp from *Staphylococcus aureus* subsp. *aureus* NCTC 8325 and *Staphylococcus epidermis* ATCC 12228 (Sequence Alignment 2) and Clp from *Listeria monocytogenes* str. 4b F2365 (LW.) and *Listeria welshimeri* serovar 6b str. SLCC5334 (Sequence Alignment 3) show a sequence identity of 98.4% and 98.5%, respectively.

Sequence data were obtained from NCBI (http://www.ncbi.nlm.nih.gov/). Alignments were produced using the Expert Protein Analysis System (ExPASy) SIM Alignment Tool for protein sequences (http://www.expasy.ch/tools/simprot.html) on the ExPASy Proteomic Server. Alignment of sequence data were computed by the comparison matrix BLOSUM62, with a gap open penalty of 12 and a gap extension penalty set to 4.

Example 6

β-Lactones as Privileged Structures for the Active Site Labeling of Versatile Bacterial Enzyme Classes A chemical proteomic strategy, referred to as Activity Based Protein Profiling (ABPP), developed by Cravatt and coworkers, [M. J. Evans et al., Chem. Rev. 2006, 106, 3279] which uses active site-directed probes, was directly applied to bacterial proteomes. ABPP probes consist of at least two general elements: 1) a reactive group for binding and covalently modifying the active site of a certain enzyme class, and 2) a reporter tag for the detection, enrichment and identification of probe labeled proteins [S. A. Sieber et al., Chem. Commun. (Camb) 2006, 2311]. So far, many ABPP probes utilized electrophilic reactive groups (Evans; loc. cit.) including fluorophosphonates [Y. Liu et al., Proc. Natl. Acad. Sci. U.S.A. 1999, 96, 14694], sulfonate esters [G. C. Adam et al., Nat. Biotechnol. 2002, 20, 805], or epoxides [D. Greenbaum et al., Chem. Biol. 2000, 7, 569] which exhibit preferences for active site nucleophiles of several distinct enzyme classes. For bacterial ABPP, we selected a novel reactive group scaffold for β-lactones (2-oxetanones). In particular, we applied ABPP with β-lactones in prokaryotes to identify dedicated target enzymes with special emphasis on those which are crucial for bacterial viability and virulence.

The modification of the alkyne tag of the β-lactones to be applied to bacterial proteomes was carried out via the 1,3-dipolar Huisgen cycloaddition (click chemistry, CC) which allows to append a fluorophor reporter group for target enzyme visualization via SDS-gel electrophoresis after proteome labeling [S. A. Sieber et al., Nat. Chem. Biol. 2006, 2, 274]. This reduces unfavoured interactions between the bulky tag and the enzyme active site, as reported by Cravatt and coworkers (FIG. 7).

The library of beta-lactones to be tested comprised compounds with aliphatic or aromatic substitutions varying in length and branching. To evaluate the target selectivity, the beta-lactones were screened against several gram-positive and gram-negative bacterial proteomes including *Pseudomonas putida, Listeria welshimeri, Bacillus licheniformis, Bacillus subtilis* and *Escherichia coli*, which are phylogenetically related to pathogenic strains. In addition, mouse liver cytosol was included as an eukaryotic reference proteome. Initial labeling experiments were carried out by adding individual probes at 50 µM concentration to the proteome which is sufficient to achieve full saturation of most targets. Interestingly, individual beta-lactones showed distinct reactivity profiles with all native proteomes investigated (FIG. 8) indicating that their substitution, especially at the C3 position, exerted a strong influence over specific beta-lactone-protein interactions. As an example, labeling of *L. welshimeri* cytosolic and membrane proteomes as well as *B. subtilis* cytosolic proteome with a subset of the most complementary probes is shown in FIGS. 9A and 9B. Only one unspecific binding event was observed in the heat denatured control of *L. welshimeri* emphasizing the preference of β-lactones predominantly for native proteins (FIG. 9C, FIG. 10). Most of the targeted proteins were of low abundance as shown by the direct comparison of the relative intensities observed with Coomassie staining vs. fluorescence scanning (FIG. 11).

Subsequent target identification by LC-MS analysis revealed the labeling of about 20 different enzymes (Table 1). MS results were confirmed by recombinant expression of all major hits and subsequent labeling by the corresponding probes (FIG. 9D, FIG. 12). The identified enzymes belong to four major families comprising ligases, oxidoreductases, hydrolases and transferases (Table 2).

TABLE 1

List of all enzymes identified (clustered by function).

| Function | Enzyme (Abbreviation) | Proteomes identified |
|---|---|---|
| Primary metabolism | AcetylCoA hydrolase (ACoAH) | P. putida |
| | Aldehyde dehydrogenase B (ADB) | E. coli |
| | Formate-C-acetyltransferase (FCA) | B. licheniformis |
| | Lipase (Lip) | L. welshimeri |
| | Lipase/acylhydrolase (LipAc) | L. welshimeri |
| | Lysophospholipase (LPL) | Mus musculus |
| | β-Ketoacyl acyl carrier protein synthase I (KAS I) | E. coli, P. putida |
| | β-Ketoacyl acyl carrier protein synthase II (KAS II) | B. subtilis, B. licheniformis, E. coli, L. welshimeri |
| | β-Ketoacyl acyl carrier protein synthase III (KAS III) | B. licheniformis |
| | β-Ketothiolase (BKT) | P. putida |
| Secondary metabolism | Surfactin A synthease subunit C (SrfAC) | B. subtilis |
| Nucleotide synthesis | CTP synthase (CTPS) | B. subtilis, B. licheniformis, E. coli, L. welshimeri |
| | Thymidylate synthase (ThyS) | L. welshimeri |
| Resistance/cell wall biosynthesis | Penicillin binding protein 4* (PBP4*) | B. subtilis |
| Virulence associated | ATP-dependent Clp protease (ClpP) | P. putida, L. welshimeri |
| | Proline iminopeptidase (PIP) | P. putida |
| Detoxification | S-Formylglutathione hydrolase (SFGH) | B. subtilis, E. coli, L. welshimeri, Mus musculus |
| | Dienelactone hydrolase (DLH) | P. putida |

TABLE 1-continued

List of all enzymes identified (clustered by function).

| Function | Enzyme (Abbreviation) | Proteomes identified |
|---|---|---|
| Unknown function | AB hydrolase (ABH) | *Mus musculus* |
| | Para-nitrobenzyl esterase (PNBE) | *B. subtilis* |
| | Peptidase S66 (Pep66) | *B. subtilis* |
| | Putative ATP dependent protease (PADP) | *P. putida* |
| | Putative esterase (PutE) | *B. licheniformis* |

All of these families require a nucleophilic residue in their active site for catalysis (Cys or Ser), which is likely to attack the electrophilic β-lactone ring. Indeed, pre-incubation of several proteins with PMSF and cerulenin, which are known active site inhibitors for serine proteases [J. C. Powers et al., Chem. Rev. 2002, 102, 4639] and cysteine containing β-ketoacyl acyl carrier protein synthases (KAS) [A. C. Price et al., J. Biol. Chem. 2001, 276, 6551], respectively, prevented subsequent probe labeling (FIG. 13). In addition, substrate inhibition assays with S-formylglutathione hydrolase (SFGH) demonstrated probe mediated inhibition of enzyme activity ($IC_{50}$=5 µM). The active site inhibition and great coverage of mechanistically distinct enzyme classes emphasizes the unprecedented utility of β-lactones as new proteomic tools for ABPP.

TABLE 2

List of all enzyme families labeled by β-lactones.

| Enzyme Class | EC | Active Site | Example |
|---|---|---|---|
| Ligase | EC 6.3.4. | Cys, His, Glu | CTP synthase |
| Oxido-reductases | EC 1.2.1. | Cys, Glu | Aldehyde deyhdrogenase B |
| Hydrolases | EC 3.1.2. | Ser, Asp, His | S-Formylglutathione hydrolase |
| | EC 3.1.1. | Ser, Glu, His | Para-nitrobenzyl esterase |
| | EC 3.4.11. | Ser, Asp, His | Proline iminopeptidase |
| | EC 3.4.21. | Ser, His | ATP-dependent Clp protease |
| Transferases | EC 2.3.1. | Cys, His, Asn | β-Ketoacyl-ACP synthase II |
| | EC 2.3.1. | Gly, Cys, Cys | Formate-C-acetyltransferase |
| | EC 2.3.1. | Cys, His, Cys | β-Ketothiolase |
| | EC 2.1.1. | Cys | Thymidylate synthase |

Interestingly, a large fraction of the identified enzymes is involved in important cellular functions such as primary (e.g., KAS I and KAS II) and secondary metabolism (e.g., surfactin A synthetase C, SurfAC), nucleotide synthesis (e.g., CTP synthase), detoxification (e.g., SFGH), antibiotic resistance (e.g., penicillin binding protein (PBP) 4*) as well as in virulence (e.g., ATP-dependent caseinolytic protease, ClpP). With the exception of SFGH, no homologue of these enzymes was detected in the mouse liver proteome.

Several targets were of special medicinal interest: KAS II, an essential component of the fatty acid biosynthetic pathway [J. Wang et al., Proc. Natl. Acad. Sci. USA 2007, 104, 7612], is highly conserved among key pathogens [J. Wang et al., Nature 2006, 441, 358], and was labeled by the aliphatic beta-lactone probes D3 and G2 (FIG. 9A and 9B). In addition, PBP4*, an enzyme which is reported to exhibit beta-lactamase activities [D. L. Popham et al., J. Bacteriol. 1993, 175, 2917], was labeled and identified in *B. subtilis* (FIG. 9B). Although we used nonpathogenic bacterial proteomes for our screens, two virulence associated enzymes, ClpP and proline iminopeptidase (PIP), which play crucial roles in many pathogenic strains were detected in *L. welshimeri* and *P. putida*. ClpP has attracted much attention due to its fundamental role for stress tolerance and virulence in many pathogenic bacteria including *S. aureus, L. monocytogenes* and *P. aeruginosa* [A. Michel et al., J. Bacteriol. 2006, 188, 5783; Y. M. Ibrahim et al., Infect. Immun. 2005, 73, 730; 0. Gaillot et al., Mol. Microbiol. 2000, 35, 1286.]. Previous studies showed that ClpP deletions in pathogenic organisms strongly reduced the virulence of these bacteria, mainly due to the decreased production of a functional toxin (e.g. listeriolysin in *L. monocytogens*) [O. Gaillot et al., Infect. Immun. 2001, 69, 4938].

To estimate the strength of probe interactions with proteins in the proteome, we compared the reactivity profiles of selected beta-lactones across a broad concentration range from 10 µM to 5 nM. Several target enzymes displayed a very robust labeling by the probe. For example, the aliphatic beta-lactone G2 is a very sensitive probe for lipase (Lip, down to 20 nM probe concentration) but does not exhibit strong interaction with lipase/acylhydrolase (LipAc) in *L. welshimeri* (FIG. 14A). Contrary, the aromatic beta-lactone P1 shows the opposite selectivity (down to 160 nM probe concentration for LipAc) illustrating the different substrate preferences of the two enzymes. Interestingly, in *E. coli* cytosol ADB shows a strong preference only for aliphatic β-lactones (D3, G2) at 100 nM probe concentration (FIG. 14B) while no other off targets could be observed.

Similarly, several other enzymes could be clustered based on their preferred binding partners (FIG. 14C). This information is useful to gain insight into the native substrate preferences of all labeled enzymes, especially for those which are less explored and uncharacterized. In this context it is interesting to note that undecorated beta-lactones (A1) seem to be poor in enzyme labeling probably due to a lack of strong active site interactions. Additionally, steric constraint in probes O1 and L1 also decreased the number of specific labeling events. Therefore, β-lactones with aliphatic and aromatic moieties seem to be the most potent probes.

The active site labeling of essential enzymes such as KAS II raised the question of a possible antibacterial effect of individual library members. Several probes were tested for growth inhibition but no antibiotic activity could be observed. One possible reason could be a limited cellular uptake of probes by intact bacteria. To clarify this, we incubated *L. welshimeri* with varying concentrations of probes in vivo. These experiments revealed that KAS II, the most important target for viability, was only weakly labeled at high concentrations (100 µM) and therefore did probably not reach saturation for full inhibition. In contrast, strong labeling occurred for the virulence associated enzyme ClpP with probe concentrations as low as 5 µM (FIG. 14D). This specific and sensitive in vivo labeling of a common virulence factor, which is not essential for viability but indispensable for bacterial pathogenesis, shows that probes work for in vivo studies and represents an attractive strategy for targeting bacteria in the future. In fact, inhibitors of virulence associated enzymes display many advantages over conventional antibiotics, such as preserving the host endogenous microbiome, and exerting less selective pressure, which may result in decreased resistance leading to longer lasting drugs [A. E. Clatworthy et al., Nat. Chem. Biol. 2007, 3, 541].

In conclusion, the side-chain modified beta-lactones according to the present invention represent privileged structures for the design of novel ABPP probes which can be utilized as proteomic tools to screen and compare enzyme activity profiles across different bacterial proteomes. We were able to identify a variety of mechanistically distinct targets that show sensitive labeling as well as inhibition by the probe molecules. Considering the labeling of several important bacterial enzymes, this approach might represent a promising starting point for the identification of novel antibacterial targets together with their corresponding inhibitors.

2) Preparation of Proteomes

Proteomes of the bacterial strains Escherichia coli K12, Bacillus licheniformis ATCC 14580, Bacillus subtilis 168, Listeria welshimeri SLCC 5334 serovar 6b and Pseudomonas putida KT2440 were prepared from 1 L liquid cultures harvested 1 h after transition in the stationary phase by centrifugation at 13.000 rpm. All strains were grown in LB (Luria-Bertani broth) medium except Listeria welshimeri, which was maintained in BHB (brain-heart broth) medium. The bacterial cell pellets were washed with PBS, resuspended in 20 mL PBS and lysed by French press. As eukaryotic reference, the liver of a C3H mouse was homogenized in 2 mL PBS followed by sonication with a Bandelin Sonopuls with 4×15 sec. pulsed at 70% max. power.

3) Labeling of Bacterial Proteomes

Proteome samples were adjusted to a final concentration of 1 mg protein/mL by dilution in PBS prior to probe labeling. Experiments for visualization by 1D SDS-PAGE were carried out in 43 µL total volume and those for affinity enrichment in 1892 µL total volume, such that once CC reagents were added, the total reaction volume was 50 µL and 2 mL, respectively. Reactions were initiated by addition of the probe and allowed to incubate for 60 min at room temperature. For heat controls the proteome was denatured with 1 4 of 43% SDS at 95° C. for 6 min and cooled to room temperature before the probe was applied. Following incubation, reporter tagged-azide reagents (13 µM rhodamine-azide for analytical or 20 µM rhodamine-biotin-azide for preparative scale) were added followed by 1 mM TCEP and 100 µM ligand. Samples were gently vortexed and the cycloaddition initiated by the addition of 1 mM $CuSO_4$. The reactions were incubated at room temperature for 1 h (Speers, J. Amer. Chem. Soc. 125 (2003), 4686).

For analytical gel electrophoresis, 50 µL 2×SDS loading buffer were added and 50 µL applied on the gel. Fluorescence was recorded in a Fujifilm Las-3000 Fluoreszenz Darkbox with a Fujinon VRF 43LMD Lens, 605DF40 filter and 520 nm EPI excitation wavelength.

Reactions for enrichment were carried out together with a control lacking the probe to compare the results of the biotin-avidin enriched samples with the background of unspecific protein binding on avidin-agarose beads. After CC proteins were precipitated using an equal volume of pre-chilled acetone. Samples were stored on ice for 20 min and centrifuged at 13,000 rpm for 10 min. The supernatant was discarded and the pellet washed two times with 400 µL of pre-chilled methanol and resuspended by sonication. Subsequently, the pellet was dissolved in 1 mL PBS with 0.2% SDS by sonication and incubated under gentle mixing with 50 µL of avidin-agarose beads (Sigma-Aldrich) for 1 h at room temperature. The beads were washed three times with 1 mL of PBS/0.2% SDS, twice with 1 mL of 6 M urea and three times with 1 mL PBS. 50 µL of 2×SDS loading buffer were added and the proteins released for preparative SDS-PAGE by 6 min incubation at 95° C. Gel bands were isolated, washed and tryptically digested as described previously (Sieber, Nat. Chem. Biol. 2 (2006) 274).

For analytical and preparative in vivo studies, bacteria were grown to stationary phase, pelleted by centrifugation (2 ml for analytical and 10 ml for preparative studies), resuspended with PBS and incubated for 2 h with varying concentrations of probe at room temperature (RT). Subsequently, the cells were lysed by sonication and separated into cytosolic and membrane fractions, followed by CC as described above.

4) Competitive Labeling with PMSF and Cerulenin

In competitive assays, a 100 fold excess of PMSF or cerulenin was added to the proteome 15 min prior to beta-lactone addition.

5) $IC_{50}$ Determination

SFGH mediated proteolysis of the p-nitrophenylacetate leads to the release of p-nitrophenol which can be monitored at 400 nm. Various concentrations of beta-lactone G2 were added to a solution containing the substrate (2.4 mM) and enzyme (30 nM). Reactions were started by addition of the enzyme and subsequently monitored for 6 min. The mean average slopes of absorption (out of three independent experiments) versus beta-lactone concentration were plotted and the concentration of 50% inhibition ($IC_{50}$) was estimated.

6) Mass Spectrometry and Bioinformatics

Tryptic peptides were loaded onto a Dionex C18 Nano Trap Column (100 µm) and subsequently eluted and separated by a Dionex C18 PepMap 100 (3 µm) column for analysis by tandem MS followed by high resolution MS using a coupled Dionex Ultimate 3000 LC-ThermoFinnegan LTQ-FT MS system.

The mass spectrometry data were searched using the SEQUEST algorithm against the corresponding databases via the software "bioworks". The search was limited to only tryptic peptides, two missed cleavage sites, monoisotopic precursor ions and a peptide tolerance of <10 ppm. Filters were set to further refine the search results. The Xcorr vs. charge state filter was set to Xcorr values of 1.5, 2.0 and 2.5 for charge states +1, +2 and +3, respectively. The number of different peptides has to be ≥2 and the peptide probability filter was set to <0.001. These filter values are similar to others previously reported for SEQUEST analysis (Mirza, Physiol. Genomics 30 (2007), 89). Minimum P-values and Xcorr values of each run as well as the total number of obtained peptides are reported in Table S1.

TABLE S1

| Proteins identified by mass spectrometry | | | | | | | |
|---|---|---|---|---|---|---|---|
| Species | Protein | Protein ID | MW | R | min. p Value | max. Xcorr | NP |
| Bacillus subtilis cytosol | Surfactin synthetase subunit 3 (SrfAC) | NP_388233 | 143727.1 | 1 2 | $2.22 \cdot 10^{-15}$ $1.00 \cdot 10^{-30}$ | 5.31 5.83 | 20 32 |
| | Putative Esterase YjcH (SFGH) | CAB13043 | 27899.2 | 1 | $3.33 \cdot 10^{-15}$ | 5.14 | 10 |

TABLE S1-continued

Proteins identified by mass spectrometry

| Species | Protein | Protein ID | MW | R | min. p Value | max. Xcorr | NP |
|---|---|---|---|---|---|---|---|
| | Hypothetical protein yocD (Pep66) | CAB13809 | 36387.3 | 1 | $7.54 \cdot 10^{-13}$ | 4.19 | 3 |
| | Beta-ketoacyl-(acyl-carrier-protein) synthase II (KAS II) | NP_389016 | 43977.0 | 1 | $1.00 \cdot 10^{-30}$ | 6.06 | 13 |
| | | | | 2 | $1.87 \cdot 10^{-11}$ | 5.27 | 9 |
| | CTP Synthase (CTPS) | CAB15743 | 59680.7 | 1 | $2.00 \cdot 10^{-15}$ | 4.43 | 16 |
| | | | | 2 | $1.00 \cdot 10^{-30}$ | 5.16 | 27 |
| | | | | 3 | $5.60 \cdot 10^{-14}$ | 4.04 | 15 |
| | Paranitrobenzyl esterase (PNBE) | NP_391319 | 53952.3 | 1 | $8.55 \cdot 10^{-15}$ | 5.19 | 5 |
| | | | | 2 | $2.30 \cdot 10^{-12}$ | 4.87 | 3 |
| | Penicillin-binding protein 4* (PBP4*) | NP_391324 | 51436.8 | 1 | $1.11 \cdot 10^{-14}$ | 6.16 | 12 |
| | | | | 2 | $7.91 \cdot 10^{-9}$ | 2.89 | 3 |
| Bacillus licheniformis cytosol | Beta-ketoacyl-(acyl-carrier-protein) synthase III (KAS III) | YP_078421 | 33855.1 | 1 | $1.00 \cdot 10^{-30}$ | 5.52 | 4 |
| | | | | 2 | $3.33 \cdot 10^{-16}$ | 5.36 | 19 |
| | Beta-ketoacyl-(acyl-carrier-protein) synthase II (KAS II) | YP_078422 | 43729.0 | 1 | $6.66 \cdot 10^{-16}$ | 5.57 | 5 |
| | | | | 2 | $1.33 \cdot 10^{-15}$ | 5.36 | 15 |
| | CTP Synthase (CTPS) | YP_093470 | 59770.8 | 1 | $1.00 \cdot 10^{-30}$ | 5.14 | 11 |
| | | | | 2 | $2.78 \cdot 10^{-15}$ | 4.94 | 21 |
| | Putative formate C-acetyltransferase (FCA) | YP_079294 | 83378.1 | 1 | $2.32 \cdot 10^{-05}$ | 3.05 | 2 |
| | | | | 2 | $1.77 \cdot 10^{-13}$ | 6.63 | 12 |
| | Putative esterase YitV (PutE) | YP_078404 | 29759.6 | 1 | $4.00 \cdot 10^{-14}$ | 4.95 | 6 |
| Escherichia coli cytosol | Aldehyde dehydrogenase B (ADB) | AAC76612 | 56270.5 | 1 | $1.00 \cdot 10^{-30}$ | 5.99 | 18 |
| | | | | 2 | $3.33 \cdot 10^{-16}$ | 5.44 | 16 |
| | Beta-ketoacyl-(acyl-carrier-protein) synthase II (KAS II) | NP_415613 | 43045.7 | 1 | $1.00 \cdot 10^{-30}$ | 6.67 | 14 |
| | Beta-ketoacyl-(acyl-carrier-protein) synthase I (KAS I) | NP_416826 | 42586.1 | 1 | $1.11 \cdot 10^{-15}$ | 6.70 | 15 |
| | Predicted esterase (SFGH) | AAC73458 | 31404.3 | 1 | $3.28 \cdot 10^{-13}$ | 4.63 | 5 |
| | | | | 2 | $6.66 \cdot 10^{-14}$ | 4.85 | 2 |
| | CTP Synthase (CTPS) | AAC75822 | 60374.1 | 1 | $1.47 \cdot 10^{-10}$ | 4.72 | 4 |
| | | | | 2 | $5.55 \cdot 10^{-15}$ | 5.19 | 10 |
| Listeria welshimeri cytosol | CTP Synthase, PyrG (CTPS) | YP_850706 | 59561.9 | 1 | $4.61 \cdot 10^{-10}$ | 4.62 | 4 |
| | | | | 2 | $3.75 \cdot 10^{-5}$ | 2.65 | 2 |
| | Beta-ketoacyl-(acyl-carrier-protein) synthase II (KAS II) | YP_850415 | 44189.0 | 1 | $5.74 \cdot 10^{-13}$ | 6.34 | 8 |
| | | | | 2 | $6.84 \cdot 10^{-6}$ | 3.37 | 2 |
| | | | | 3 | $4.29 \cdot 10^{-8}$ | 4.05 | 6 |
| | Lipase (Lip) | YP_850307 | 38500.3 | 1 | $4.99 \cdot 10^{-10}$ | 4.42 | 3 |
| | Thymidylate synthase, ThyA (ThyS) | YP_850091 | 36104.1 | 1 | $6.03 \cdot 10^{-7}$ | 2.24 | 2 |
| | | | | 2 | $1.63 \cdot 10^{-9}$ | 3.48 | 2 |
| | Tributyrin esterase, EstA (SFGH) | YP_850577 | 28894.1 | 1 | $2.76 \cdot 10^{-6}$ | 2.48 | 2 |
| Listeria welshimeri membrane | Beta-ketoacyl-(acyl-carrier-protein) synthase II (KAS II) | YP_850415 | 44189.0 | 1 | $8.72 \cdot 10^{-10}$ | 3.63 | 2 |
| | Lipase (Lip) | YP_850307 | 38500.3 | 1 | $5.33 \cdot 10^{-15}$ | 5.12 | 12 |
| | | | | 2 | $4.44 \cdot 10^{-16}$ | 4.92 | 3 |
| | Lipase/acylhydrolase putative (LipAc) | YP_850078 | 29611.4 | 1 | $1.48 \cdot 10^{-11}$ | 4.37 | 10 |
| | | | | 2 | $1.19 \cdot 10^{-9}$ | 3.63 | 3 |
| | ATP-dependent Clp protease proteolytic subunit (ClpP) | YP_850614 | 21591.0 | 1 | $1.28 \cdot 10^{-8}$ | 3.91 | 4 |
| | | | | 2 | $2.28 \cdot 10^{-6}$ | 3.08 | 2 |
| Mus musculus cytosol | Abhydrolase domain containing protein 14B (ABH) | NP_083907 | 22436.6 | 1 | $1.38 \cdot 10^{-10}$ | 4.77 | 2 |
| | | | | 2 | $1.11 \cdot 10^{-16}$ | 5.03 | 6 |
| | | | | 3 | $1.11 \cdot 10^{-15}$ | 5.01 | 5 |
| | Carboxylesterase 6 (CEI) | NP_598721 | 61900.3 | 1 | $2.65 \cdot 10^{-13}$ | 5.02 | 7 |
| | | | | 2 | $6.08 \cdot 10^{-13}$ | 4.16 | 3 |
| | Carboxylesterase 5 (CEI) | NP_766347 | 62277.4 | 1 | $2.21 \cdot 10^{-10}$ | 5.37 | 10 |
| | | | | 2 | $5.19 \cdot 10^{-08}$ | 4.04 | 2 |

TABLE S1-continued

Proteins identified by mass spectrometry

| Species | Protein | Protein ID | MW | R | min. p Value | max. Xcorr | NP |
|---|---|---|---|---|---|---|---|
| | Carboxylesterase 31 isoforms (CEI) | — | — | 1 | $6.82 \cdot 10^{-11}$ | 5.04 | 8 |
| | | | | 2 | $5.79 \cdot 10^{-10}$ | 3.44 | 3 |
| | Lysophospholipase-like protein 1 (LPL) | AAH52848 | 24671.4 | 1 | $5.82 \cdot 10^{-7}$ | 3.23 | 2 |
| | | | | 2 | $6.85 \cdot 10^{-8}$ | 3.53 | 2 |
| | | | | 3 | $5.06 \cdot 10^{-5}$ | 3.05 | 2 |
| | Esterase D/formylglutathione hydrolase (SFGH) | NP_058599 | 31299.3 | 1 | $1.31 \cdot 10^{-12}$ | 4.86 | 5 |
| | | | | 2 | $4.57 \cdot 10^{-11}$ | 5.76 | 5 |
| | | | | 3 | $7.97 \cdot 10^{-13}$ | 5.07 | 4 |
| P. putida cytosol | ATP-dependent Clp protease proteolytic subunit (ClpP) | NP_744449 | 23499.9 | 1 | $5.55 \cdot 10^{-15}$ | 5.57 | 8 |
| | | | | 2 | $2.80 \cdot 10^{-13}$ | 5.39 | 5 |
| | | | | 3 | $1.13 \cdot 10^{-11}$ | 4.15 | 1 |
| | Proline iminopeptidase (PIP) | NP_747129 | 36566.5 | 1 | $7.44 \cdot 10^{-14}$ | 5.68 | 11 |
| | | | | 2 | $7.87 \cdot 10^{-10}$ | 3.75 | 3 |
| | Acetyl-CoA hydrolase (ACoAH) | NP_742324 | 53923.8 | 1 | $1.00 \cdot 10^{-30}$ | 4.80 | 7 |
| | | | | 2 | $6.51 \cdot 10^{-13}$ | 3.96 | 4 |
| | | | | 3 | $9.29 \cdot 10^{-12}$ | 3.99 | 6 |
| | ATP-dependent protease, putative (PADP) | NP_742841 | 89621.9 | 1 | $2.89 \cdot 10^{-14}$ | 5.00 | 24 |
| | Beta-ketothiolase (BKT) | NP_745884 | 40962.4 | 1 | $5.33 \cdot 10^{-07}$ | 2.80 | 2 |
| | | | | 2 | $4.79 \cdot 10^{-10}$ | 3.43 | 7 |
| | Beta-ketoacyl-(acyl-carrier-protein) synthase I (KAS I) | NP_746292 | 43236.7 | 1 | $1.00 \cdot 10^{-30}$ | 6.03 | 10 |
| | | | | 2 | $1.67 \cdot 10^{-14}$ | 5.33 | 6 |
| | | | | 3 | $3.33 \cdot 10^{-15}$ | 5.94 | 5 |
| | Dienelactone hydrolase (DLH) | NP_746295 | 26252.3 | 1 | $6.24 \cdot 10^{-12}$ | 2.71 | 2 |
| | | | | 2 | $3.31 \cdot 10^{-10}$ | 4.30 | 6 |
| | | | | 3 | $2.55 \cdot 10^{-9}$ | 4.07 | 2 |

This list of proteins shows Protein ID, molecular weight (MW) of the protein, the replicates (R) in which the proteins have been identified, the minimum P-values, maximum Xcorr and the number of peptides (NP) found in each replicate.

7) Recombinant Expression

The major hits of MS analysis were recombinantly expressed in E. coli as an internal control of the MS results by using the Invitrogen™ Gateway® Technology. Target genes were amplified from the corresponding genomes by PCR with an AccuPrime™ Pfx DNA Polymerase kit with 65 ng of genomic DNA, prepared by standard protocols. attB1 forward primer and attB2 reverse primer were designed to yield attB-PCR Products needed for Gateway® Technology:

```
Para-nitrobenzyl esterase B. subtilis 168
forward primer:
5'-GGG GAC AAG TTT GTA CAA AAA AGC AGG CTA CAT

GAC TCA TCA AAT AGT AAC G reverse primer:
5'-GGG GAC CAC TTT GTA CAA GAA AGC TGG GTG TTA

TTC TCC TTT TGA AGG GAA

Penicillin-binding protein 4* B. subtilis 168
forward primer:
5'-GGG GAC AAG TTT GTA CAA AAA AGC AGG CTA CAT

GAA GCA GAA TAA AAG AAA GCA T reverse primer:
5'-GGG GAC CAC TTT GTA CAA GAA AGC TGG GTG CTA

CTT CGT ACG GAC CG

Aldehyde dehydrogenase B E. coli K12
forward primer:
5'-GGG GAC AAG TTT GTA CAA AAA AGC AGG CTA CAT

GAC CAA TAA TCC CCC TTC AGC reverse primer:
5'-GGG GAC CAC TTT GTA CAA GAA AGC TGG GTG TCA

GAA CAG CCC CAA CGG TTT AT

ATP-dependent Clp protease, proteolytic
subunit, ClpP P. putida KT2440
forward primer:
5'-GGG GAC AAG TTT GTA CAA AAA AGC AGG CTA CAT

GTC CCG CAA TTC TTA TAT TCA GC reverse primer:
5'-GGG GAC CAC TTT GTA CAA GAA AGC TGG GTG TCA

GGA GGC CAG TTG CCG

CTP Synthase, B. subtilis 168
forward primer:
5'-GGG GAC AAG TTT GTA CAA AAA AGC AGG CTA CAT

GAC GAA ATA TAT TTT TGT AAC reverse primer:
5'-GGG GAC CAC TTT GTA CAA GAA AGC TGG GTG TTA

CTT CTG ATT TGC AGC T

FabF beta ketoacyl carrier synthase II,
L. welshimeri, serovar 6b-SLCC5334
forward primer:
5'-GGG GAC AAG TTT GTA CAA AAA AGC AGG CTA CAT

GGA TAA AAA AAG AGT AGT TG reverse primer:
5'-GGG GAC CAC TTT GTA CAA GAA AGC TGG GTG TTA

GTC TTC TAT TCT TTT AAA TAC
```

```
Lipase L. welshimeri serovar 6b-SLCC5334
forward primer:
5'-GGG GAC AAG TTT GTA CAA AAA AGC AGG CTA CAT

GAA AAA TAC AAT AAA ATG G reverse primer:
5'-GGG GAC CAC TTT GTA CAA GAA AGC TGG GTG TTA

CTT TTC TTC TAA GAA C

Proline iminopeptidase, P. putida KT2440
forward primer:
5'-GGG GAC AAG TTT GTA CAA AAA AGC AGG CTA CAT

GCA GAC CCT CTA CCC G reverse primer:
5'-GGG GAC CAC TTT GTA CAA GAA AGC TGG GTG TCA

TGC TTC TTC CAG AGG CAA

S-formylglutathione hydrolase, E. coli K12
forward primer:
5'-GGG GAC AAG TTT GTA CAA AAA AGC AGG CTA CAT

GGA ACT CAT TGA AAA ACA T reverse primer:
5'-GGG GAC CAC TTT GTA CAA GAA AGC TGG GTG TCA

ACG CAT ATT CAG TTT ATT
```

PCR products were identified on agarose gels and gel bands were isolated and extracted with an E.Z.N.A.™ MicroElute™ Gel Extraction Kit. Concentrations of DNA were measured by a NanoDrop Spectrophotometer ND-1000. 100 fmol of purified attB-PCR product and 50 fmol of attP-containing donor vector pDONR™201 in TE buffer were used for in vitro BP recombination reaction with BP Clonase™ II enzyme mix to yield the appropriate attL-containing entry clone. After transformation in chemically competent One Shot® TOP 10 *E. coli* (Invitrogen), cells were plated on LB agar plates containing 25 µg mL$^{-1}$ kanamycin. Clones of transformed cells were selected and grown in kanamycin LB medium. Cells were harvested and plasmids were isolated using an E.Z.N.A.™ Plasmid Mini Kit. The corresponding attB-containing expression clone was generated by in vitro LR recombination reaction of approx. 50 fmol of the attL-containing entry clone and 50 fmol of the attR-containing destination vector pDest using LR Clonase™ II enzyme mix in TE buffer. The expression clone was transformed in chemically competent BL21 *E. coli* cells (Novagen) and selected on LB agar plates containing 100 µg mL$^{-1}$ carbenicillin. Validity of the clones was confirmed by plasmid sequence analysis. Recombinant clones were grown in carbenicillin LB medium and target gene expression was induced with anhydrotetracyclin.

Labeled Proteomes

Cytosol and membrane fractions of the proteome were labeled separately. However, except for *L. welshimeri* membrane fractions showed less intensive and specific labeling pattern compared to the cytosol.

Examples for heat denatured proteome controls are given in FIG. 10. The majority of the labeled part of the proteome is shown to be heat sensitive and thus can be regarded as results of specific activity based binding events. Labeling profiles for cis and trans-β-lactones and fluorescent gels of recombinantly expressed target proteins are shown in FIG. 15 and FIG. 10, respectively.

The 1D SDS-PAGE gels for all proteomes and identified proteins assigned to the corresponding gel bands of *E. coli* (A), *P. putida* (B), *L. welshimeri* (C), *B. licheniformis* (D), *B. subtilis* (E) and mouse (F) are shown in FIG. 8.

Example 7

In Vivo Labelling

This example relates to the in vivo labelling of the proteome of *S. aureus* with β-lactones. The beta-lactones were applied at a certain concentration to approx. 2×10$^9$ cfu of stationary phase *S. aureus* in 100 µL PBS and incubated for 2 h. Excess beta-lactone was removed by washing the cells 3× with 1 mL PBS each. Then the cells were lysed by sonication. FIG. 16A shows a fluorescent gel of *S. aureus* cytosol after treatment with selected library members. ClpP has been identified by mass spectrometry from preparative SDS gels after workup and tryptic digestion. FIG. 16B demonstrates that the in vivo dose down of beta-lactones D3, E2 and G2 with *S. aureus* indicates strong labelling by beta-lactone D3. FIG. 16C shows the increase of selectivity at 8.0 µM concentration. ClpP is still labelled by D3 but almost no off-targets are visible at this concentration.

Example 8

Inhibition of ClpP by Beta-Lactones Reduces the Virulence of *Listeria monocytogenes*

1) Bacterial Strains and Eukaryotic Tissue Culture

*Listeria welshimeri* strain SLCC 5334 serovar 6b and *Listeria monocytogenes* strains EGDe and F2365 were maintained in BHB (brain heart broth) medium at 37° C.

HeLa cells were grown in 90% Dulbecco's modified Eagle's medium (DMEM) high glucose (4.5 g L$^{-1}$) without pyruvate supplemented with 10% fetal bovine serum (FBS) with broad spectrum antibiotics. Cells were harvested with trypsin/EDTA before reaching confluence and split. The mouse macrophage-like cell line J774A.1 (DSMZ, Germany) was maintained in 90% DMEM containing low glucose (1.0 g L$^{-1}$) L-glutamine, sodium pyruvate and sodium hydrogen carbonate supplemented with 10% FBS with broad spectrum antibiotics. Cells were detached from the culture flasks using TEN buffer (40 mM TrisCl, 1 mM EDTA, 150 mM NaCl, pH 7.5) before reaching confluence and split to about ⅓ to ¼. Eukaryotic cells were grown adhesive at 37° C. with 5% CO$_2$ in tissue culture flasks.

2) In Vivo Labeling of *Listeria* Proteomes

For analytical and preparative in vivo studies, *Listeria* were grown to stationary phase and harvested by centrifugation at 4.000 rpm 1 h after entrance in the stationary phase (1.5 ml for analytical and 15 ml for preparative studies). The cell pellets were washed once with PBS and resuspended in 100 µL and 500 µL PBS for analytical and preparative studies, respectively. The cell suspensions were incubated for 2 h with varying concentrations of probe at room temperature. Probes were applied from DMSO stocks whereby DMSO never exceeded 2% in the final solution. For preparative experiments, 50 µM of the probes was added to the cells resuspended in PBS. After incubation, the cells were washed thoroughly three times with PBS to remove excess probe from the supernatant. Subsequently the cells were lysed in 100 µL (500 µL) PBS by sonication with a Bandelin Sonopuls with 3×20 sec. pulsed at 70% max. power.

For analytical experiments 44 µL proteome were used to append a reporter tag via CC, such that once CC reagents were added, the total reaction volume was 50 µL. In preparative purposes the total volume of 500 µL was consumed per experiment. Reporter tagged-azide reagents (13 μM rhodamine-azide for analytical or 20 μM rhodamine-biotin-azide for preparative scale) were added followed by 1 mM TCEP and 100 μM ligand. Samples were gently vortexed and the cycloaddition initiated by the addition of 1 mM $CuSO_4$. The reactions were incubated at room temperature for 1 h. For analytical gel electrophoresis, 50 μL 2×SDS loading buffer were added and 50 μL applied on the gel. Fluorescence was recorded in a Fujifilm Las-3000 Fluoreszenz Darkbox with a Fujinon VRF 43LMD Lens, 605DF40 filter and 520 nm EPI excitation wavelength.

The labeling of *L. monocytogenes* EGDe by the beta-lactone compounds shown in FIG. 2 revealed D3 and N1 as the most potent probes for ClpP labeling followed by G2 and E2, as shown in FIG. 18.

Reactions for enrichment were carried out together with a control lacking the probe to compare the results of the biotin-avidin enriched samples with the background of unspecific protein binding on avidin-agarose beads. After CC proteins were precipitated using an equal volume of pre-chilled acetone. Samples were stored on ice for 20 min and centrifuged at 13 000 rpm for 10 min. The supernatant was discarded and the pellet washed two times with 200 μL of pre-chilled methanol and resuspended by sonication. Subsequently, the pellet was dissolved in 1 mL PBS with 0.2% SDS by sonication and incubated under gentle mixing with 50 μL of avidin-agarose beads (Sigma-Aldrich) for 1 h at room temperature. The beads were washed three times with 1 mL of PBS/0.2% SDS, twice with 1 mL of 6 M urea and three times with 1 mL PBS. 50 μL of 2×SDS loading buffer were added and the proteins released for preparative SDS-PAGE by 6 min incubation at 95° C. Gel bands were isolated, washed and tryptically digested as described in Sieber et al., 2006.

3) Mass Spectrometry and Bioinformatics

Mass spectrometry and bioinformatics were carried out as described in J Am Chem Soc 2008, 130, 14400 (incorporated herein by reference). In brief, tryptic peptides were separated by LC and analysed by tandem MS followed by high resolution MS in a coupled LTQ-FT MS system. Protein identities were revealed using the SEQUEST search algorithm with refinement by filter settings.

4) LLO Haemolytic Activity Testing

Overnight cultures of *L. monocytogenes* EGDe were harvested by centrifugation and resuspended in an equal volume of fresh BHB medium. In 1.5 mL Eppendorf tubes, 400 μL of BHB medium were inoculated with 4 μL of the resuspended *Listeria* culture and 4 μL of a corresponding beta-lactone stock in DMSO. The final concentrations were 800 μM, 400 μM, 200 μM, 100 μM and DMSO as control. The amount of DMSO in all tests was 1% of the medium. After mixing, the test tubes were incubated under continuous shaking at 200 rpm at 37° C. for 16 h. Then, cells were centrifuged and the supernatants filtered sterile by passing them through a 0.2 μm pore size filter. Haemolytic activity of LLO in the culture supernatants was quantitatively investigated according to a method described in J. Food Safety 1998, 18: 197-203 (incorporated herein by reference) with some modifications. In Nunclon™ 96-well plates with round shaped wells 100 μL of serial dilutions of the supernatants in PBS were added per well and incubated with 100 μL of 3% SRBC (sheep red blood cells) resuspended in PBS for 15 min at 37° C. under gentle shaking. The 96-well plates were centrifuged at 600 rpm for 5 min and the minimum dilution at which intact blood cells began to form a pellet was recorded. Controls with no lactone were set 100%. Buffer only controls and pure BHB medium yielded no haemolysis.

The beta-lactone compounds U1 and N1 revealed a significant reduction of haemolytic activity of up to 90% with an $EC_{50}$<100 μM, while D3 showed an inhibition of 80% with an $EC_{50}$=100 μM, as shown in FIG. 19A) and FIG. 20. Probe M1, that did not label and inhibit ClpP, revealed no effect on haemolysis.

5) PI-PLC Activity Assay

PI-PLC activity was tested on *Listeria*-agar according to Ottaviani and Agosti (Heipha Diagnostika, Eppelheim, Germany). Sterile circles of Whatman® cards (No. 1, Schleicher & Schuell) with 5.5 mm diameter were placed on the agar plates and inoculated with 2.5 μL of the corresponding lactone/DMSO and 2.5 μL stationary phase culture of *L. monocytogenes* EGDe diluted to $OD_{600}$=0.13 in BHB medium. After incubation at 37° C. for 17 h, the diameters of the zones around the colonies on the discs were precisely measured using a vernier calliper. The diameters of the DMSO control tests were set 100% activity. Curve fittings were produced by Microcal™ Origin 6.0.

As shown in FIG. 19B), the beta-lactone compound U1 led to an approximately 50% reduction of PI-PLC activity.

6) Cytotoxicity of Beta-Lactone U1

Cytotoxicity was determined in HeLa cells using the WST-1 cell proliferation test. Trypsinated cells were seeded at 100 μL aliquots with antibiotic free medium in Nunclon™ flat-bottom 96-well plates with $1 \cdot 10^4$ cells per well. After incubation of HeLa cells for 24 h, the medium was replaced by antibiotic free test medium containing 1 mM, 100 μM and 10 μM beta-lactone U1, DMSO as non-toxic control and 1% Triton X-100 as 100% lethal control. The DMSO content in all tests was kept at 1%. HeLa cells with test medium were incubated for 24 h, then 10 μL WST-1 reagent were added and after 30 min incubation absorption at 450 nm was read with 630 nm reference wavelength using a TECAN GENios Pro microplate reader.

Neither microscopic alterations of cell morphology nor significant inhibition of cell proliferation of HeLa cells occurred 24 h after treatment even with the highest concentration of 1 mM of beta-lactone compound U1.

7) Infection of J774 Cells and Intracellular Growth Assay

In a Nunclon™ 96-well plate with flat-bottom $1 \cdot 10^5$ J774 cells per well were seeded in 100 μL 90% DMEM medium with 10% FBS without antibiotics. After 24 h incubation the resulting monolayer was washed once with 100 μL PBS and 100 μL of *L. monocytogenes* EGDe suspension in 90% DMEM medium with 10% FBS without antibiotics was added either with 1 mM beta-lactone U1 or DMSO. *L. monocytogenes* was grown in an over night culture with beta-lactone/DMSO and resuspended to approximately $10^6$ cells/mL resulting in a multiplicity of infection (MOI) of 0.5. Macrophages were infected for 15 min at 37° C. after 15 min bacterial adherence on ice, as described in Molecular Microbiol. 2000, 35(6): 1286-1294 (incorporated herein by reference). Thereafter, the infected monolayer were washed two times with 100 μL PBS each and fresh 90% DMEM medium with 10% FBS containing 10 μg/mL gentamicin and 1 mM beta-lactone U1 or DMSO was added. After 0, 3 and 5 h post infection, the monolayers were washed again with two times 100 μL PBS and eukaryotic cells lysed by the addition of two times 250 μL of 0.05% solution of Triton X-100 in sterile deionised water. Intracellular bacteria were quantified by colony counting of serial dilutions plated on *Listeria*-agar (Ottaviani & Agosti Agar, Heipha Diagnostika, Eppelheim, Germany).

A comparable number of bacteria were taken up by the macrophages during infection. Bacterial counts from lysed mouse macrophages 3 h and 5 h post infection revealed a significant lower growth in the eukaryotic cells, i.e. approximately 76%, when treated with beta-lactone compound U1, as shown in FIG. 21.

The invention claimed is:

1. A method for treating, preventing or ameliorating a bacterial or protozoan infection comprising the administration of a compound of the general formula (I)

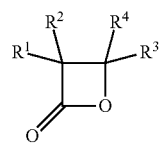

wherein $R^1$ is $C_{3-16}$ alkyl, $C_{3-16}$ alkenyl, $C_{3-16}$ alkynyl, which may be substituted and/or which may be interrupted by one or more heteroatoms or heterogroups selected from O, S or $NR^5$, with $R^5$ being selected from —H or —$C_{1-4}$ alkyl; phenyl which may be substituted; or $C_{7-12}$ aralkyl which may be substituted on the aryl ring, $R^2$ is H, $R^3$ is H; $C_{1-12}$ alkyl, $C_{2-12}$ alkenyl, $C_{2-12}$ alkynyl, which may be substituted and/or which may be interrupted by one or more heteroatoms or heterogroups selected from O, S or $NR^5$, with $R^5$ being selected from —H or —$C_{1-4}$ alkyl; phenyl which may be substituted; or $C_{7-12}$ aralkyl which may be substituted on the aryl ring, and $R^4$ is H or $C^{1-8}$ alkyl which may be substituted and/or which may be interrupted by one or more heteroatoms or heterogroups selected from O, S or $NR^5$, with $R^5$ being selected from —H or —$C_{1-4}$ alkyl, or $R^3$ and $R^4$ are taken together to form a 5- or 6-membered carbocyclic ring, or a pharmaceutically acceptable salt thereof.

2. The method of claim 1, wherein $R^1$ is $C_{4-14}$ alkyl, $C_{4-14}$ alkenyl, $C_{4-14}$ alkynyl, or phenyl which is unsubstituted or monosubstituted.

3. The method of claim 1, wherein $R^1$ is $C_{8-12}$ alkyl, $C_{8-12}$ alkenyl or $C_{8-12}$ alkynyl.

4. The method of claim 1, wherein $R^3$ is $C_{1-6}$ alkyl, $C_{2-6}$ alkenyl, $C_{2-6}$ alkynyl or $C_{7-10}$ aralkyl.

5. The method of claim 1, wherein $R^4$ is H.

6. The method of claim 1, wherein $R^3$ is $C_{7-8}$ aralkyl.

7. The method of claim 1, wherein $R^3$ and $R^4$ combine to form a saturated 6-membered carbocyclic ring.

8. The method of claim 1, wherein said compound is a compound having one of the following formulae U1, D3, E2, G2 or S1:

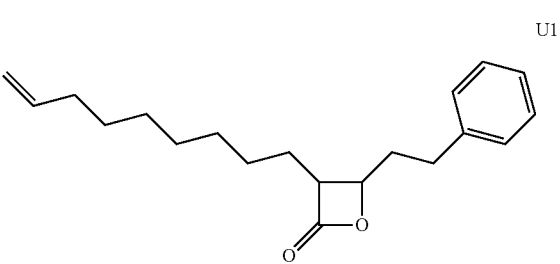 [SMILES: C=CCCCCCCCC1C(=O)OC1CCc1ccccc1]

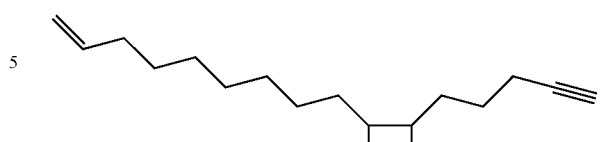

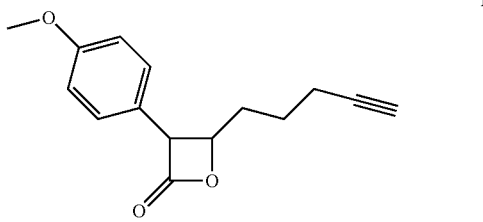

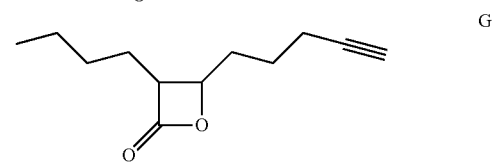

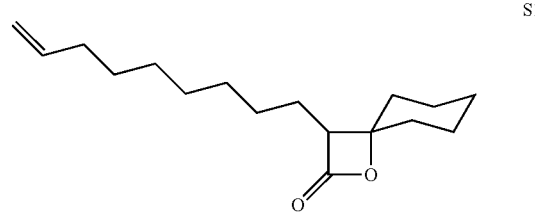

or a compound having one of said formulae U1, D3, E2, G2 or S1, wherein the terminal double bond, if said double bond is present, and/or the terminal triple bond, if said triple bond is present, is/are replaced by single bond/single bonds;

or pharmaceutically acceptable salts thereof.

9. The method of claim 1, wherein said bacterial infection is caused by Gram-positive or Gram negative bacteria and/or is selected from the group consisting of listeriosis, cranial nerve palsy, encephalitis, meningitis, meningoencephalitis, abscesses, endocarditis, pneumonia, cholera, syphilis, anthrax, leprosy, bubanic plaque, sepsis, septic arthritis, osteitis, inflammation of wounds, inflammation of organs, furuncles, carbuncles, toxic shock syndrome, Staphylococcal scalded skin snydrome (SSSS), and mastitis, or wherein said protozoan infection is selected from the group consisting of malaria, plasmodium-related hemoglobinuria, and plasmodium-related diarrhea.

10. The method of claim 9, wherein said Gram-positive bacteria are selected from the group consisting of Firmicutes and Actinobacteria.

11. The method of claim 10, wherein said Firmicutes are selected from the group consisting of *Listeria* spp., in particular *Listeria* monocytogenes, and *Listeria welshimeri*; *Staphylococcus* spp., in particular *Staphylococcus aureus, Staphylococcus epidermidis, Staphylococcus saprophyticus, Staphylococcus lugdunensis, Staphylococcus schleiferi*, and *Staphylococcus caprae; Streptococcus* spp., in particular *Streptococcus pneumoniae, Streptococcus viridans, Streptococcus pyogenes*, and *Streptococcus agalactiae; Enterococcus* spp., in particular *Enterococcus faecalis*, and *Enterococcus faecium*; and *Bacillus* spp., in particular *Bacillus*

*licheniformis, Bacillus subtilis, Bacillus anthracia, Bacillus cereus, Bacillus thuringiensis*, and *Bacillus larvae*.

12. The method of claim 10, wherein said Actinobacteria are selected from the group consisting of *Mycobacterium* spp., in particular *Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum, Mycobacterium canettii, Mycobacterium intracellulare, Mycobacterium simiae, Mycobacterium szulgai, Mycobacterium xenopi, Mycobacterium fortuitum, Mycobacterium chelonei*, and *Mycobacterium marinum; Nocardia asteroids*; and *Rhodococcus equi*.

13. The method of claim 9, wherein said Gram-negative bacteria belong to the group Proteobacteria.

14. The method of claim 13, wherein said Proteobacteria are selected from the group consisting of *Neisseria* spp., in particular *Neisseria gonorrhoeae*, and *Neisseria meningitides; Moraxella catarrhalis; Hemophilus influenzae; Klebsiella* spp., in particular *Klebsiella pneumoniae; Legionella* spp., in particular *Legionella pneumophila; Pseudomonas* spp., in particular *Pseudomonas aeruginosa*, and *Pseudomonas putida; Escherichia coli; Proteus mirabilis; Enterobacter cloaceae; Serratia marcescens; Helicobacter pylori*; and *Salmonella* spp., in particular *Salmonella enteritidis*, and *Salmonella typhi*.

15. The method of claim 1, wherein said bacterial infection induces the formation of biofilms or is associated with the formation of biofilms.

16. The method of claim 15, wherein said bacterial infection is selected from the group consisting of urinary tract infections, infections in cystic fibrosis, middle-ear infections, formation of dental plaques, gingivitis, caries, endocarditis, catheter infections, contact lens associated eye infections, and medical implant associated infections.

17. The method of claim 1, wherein said protozoan infection is caused by protozoa that belong to the group Apicomplexa.

18. The method of claim 17, wherein said Apicomplexa are selected from the group consisting of *Plasmodium* spp., in particular *Plasmodium falciparum, Plasmodium malariae, Plasmodium vivax, Plasmodium ovale*, and *Plasmodium knowlesi; Leishmania* spp., in particular *Leishmania major, Leishmania tropica, Leishmania aethiopica, Leishmania mexicana, Leishmania braziliensis, Leishmania donovani, Leishmania infantum*, and *Leishmania chagasi; Trypanosoma* spp., in particular *Trypanosoma brucei, Trypanosoma cruzi, Trypanosoma simiae, Trypanosoma avium, Trypanosoma congolense, Trypanosoma equinum, Trypanosoma equiperdum, Trypanosoma evansi*, and *Trypanosoma suis; Babesia* spp., in particular *Babesia microti*, and *Babesia bigemina*; and *Toxoplasma*, in particular *Toxoplasma gondii*.

19. The method of claim 1, whereby said compound is administered orally; rectally; parenterally, including by intravenous, intramuscular, intraperitoneal, intrastemal, subcutaneous or intraarticular injection or infusion; intracistemally; intravaginally; intraperitoneally; topically, including by powders, ointments, drops or transdermal patches; bucally; or as an oral or nasal spray.

20. The method of claim 1, whereby said compound is administered in combination with one or more antibiotics and/or antiseptics.

21. The method of claim 1, wherein said subject is a human.

\* \* \* \* \*

UNITED STATES PATENT AND TRADEMARK OFFICE
CERTIFICATE OF CORRECTION

| | |
|---|---|
| PATENT NO. | : 8,669,283 B2 |
| APPLICATION NO. | : 12/919363 |
| DATED | : March 11, 2014 |
| INVENTOR(S) | : Sieber et al. |

Page 1 of 1

It is certified that error appears in the above-identified patent and that said Letters Patent is hereby corrected as shown below:

Title Page

Item (75) Inventors:
"Stephen A. Sieber, Munich (DE)" should be -- Stephen A. Sieber, Utting (DE) --

In the Claims

Column 74, line 24, claim 19:
"intracistemally" should be -- intracisternally --

Signed and Sealed this
Nineteenth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,669,283 B2
APPLICATION NO. : 12/919363
DATED            : March 11, 2014
INVENTOR(S)      : Sieber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 495 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 26

<210> SEQ ID NO 1
<211> LENGTH: 588
<212> TYPE: DNA
<213> ORGANISM: Staphylococcus aureus subsp. aureus NCTC 8325

<400> SEQUENCE: 1

```
atgaatttaa ttcctacagt tattgaaaca acaaaccgcg gtgaacgtgc atatgatata    60
tactcacgtt tattaaaaga ccgtattatt atgttaggtt cacaaattga tgacaacgta   120
gcaaattcaa tcgtatcaca gttattattc ttacaagcgc aagactcaga gaaagatatt   180
tatttataca ttaattcacc aggtggaagt gtaacagctg gttttgcgat ttatgataca   240
attcaacaca ttaaacctga tgttcaaaca atttgtatcg gtatggctgc atcaatggga   300
tcattcttat tagcagctgg tgcaaaaggt aaacgtttcg cgttaccaaa tgcagaagta   360
atgattcacc aaccattagg tggtgctcaa ggacaagcaa ctgaaatcga aattgctgca   420
aatcacattt taaaaacacg tgaaaaatta accgcattt atcagagcg tactggtcaa     480
agtattgaaa aatacaaaa agacacagat cgtgataact tcttaactgc agaagaagct   540
aaagaatatg gcttaattga tgaagtgatg gtacctgaaa caaaataa                588
```

<210> SEQ ID NO 2
<211> LENGTH: 195
<212> TYPE: PRT
<213> ORGANISM: Staphylococcus aureus subsp. aureus NCTC 8325

<400> SEQUENCE: 2

```
Met Asn Leu Ile Pro Thr Val Ile Glu Thr Thr Asn Arg Gly Glu Arg
1               5                   10                  15

Ala Tyr Asp Ile Tyr Ser Arg Leu Leu Lys Asp Arg Ile Ile Met Leu
            20                  25                  30

Gly Ser Gln Ile Asp Asp Asn Val Ala Asn Ser Ile Val Ser Gln Leu
        35                  40                  45

Leu Phe Leu Gln Ala Gln Asp Ser Glu Lys Asp Ile Tyr Leu Tyr Ile
    50                  55                  60

Asn Ser Pro Gly Gly Ser Val Thr Ala Gly Phe Ala Ile Tyr Asp Thr
65                  70                  75                  80

Ile Gln His Ile Lys Pro Asp Val Gln Thr Ile Cys Ile Gly Met Ala
                85                  90                  95

Ala Ser Met Gly Ser Phe Leu Leu Ala Ala Gly Ala Lys Gly Lys Arg
            100                 105                 110

Phe Ala Leu Pro Asn Ala Glu Val Met Ile His Gln Pro Leu Gly Gly
        115                 120                 125

Ala Gln Gly Gln Ala Thr Glu Ile Glu Ile Ala Ala Asn His Ile Leu
    130                 135                 140

Lys Thr Arg Glu Lys Leu Asn Arg Ile Leu Ser Glu Arg Thr Gly Gln
145                 150                 155                 160

Ser Ile Glu Lys Ile Gln Lys Asp Thr Asp Arg Asp Asn Phe Leu Thr
                165                 170                 175

Ala Glu Glu Ala Lys Glu Tyr Gly Leu Ile Asp Glu Val Met Val Pro
            180                 185                 190

Glu Thr Lys
        195
```

<210> SEQ ID NO 3
<211> LENGTH: 585
<212> TYPE: DNA
<213> ORGANISM: Staphylococcus epidermis

<400> SEQUENCE: 3

```
atgaatttaa ttcctacagt tattgaaaca actaaccgcg gtgaacgtgc gtatgatata      60
tattcacgtt tgttgaaaga ccgtattatc atgctaggtt ctcaaattga tgataacgta     120
gctaactcta ttgtgtcaca attattattc ttgcaagcgc aagattctga aaaggatatt     180
tatttatata ttaattcacc aggtggcagt gtaactgctg gatttgctat ttatgatact     240
atccaacata tcaaaccaga cgttcaaaca atctgtattg gtatggcagc gtctatgggt     300
tcattcttgt tagcagcagg tgcaaaaggt aaacgatttg cgctacctaa tgctgaagtt     360
atgattcacc aaccattagg tggtgcacaa ggacaagcaa ctgaaattga aattgcagca     420
aatcatattt taaaaacacg tgaaaaatta atcgtatttt tatcagaacg tacaggtcaa     480
tcaattgaaa aaattcaaca agatactgat cgcgacaact tcttaacagc tgcagaagct     540
aaagaatatg gattaattga tgaagtaatg gaaccagaaa ataa                      585
```

<210> SEQ ID NO 4
<211> LENGTH: 194
<212> TYPE: PRT
<213> ORGANISM: Staphylococcus epidermis ATCC 12228

<400> SEQUENCE: 4

```
Met Asn Leu Ile Pro Thr Val Ile Glu Thr Thr Asn Arg Gly Glu Arg
1               5                   10                  15

Ala Tyr Asp Ile Tyr Ser Arg Leu Leu Lys Asp Arg Ile Ile Met Leu
            20                  25                  30

Gly Ser Gln Ile Asp Asp Asn Val Ala Asn Ser Ile Val Ser Gln Leu
        35                  40                  45

Leu Phe Leu Gln Ala Gln Asp Ser Glu Lys Asp Ile Tyr Leu Tyr Ile
    50                  55                  60

Asn Ser Pro Gly Gly Ser Val Thr Ala Gly Phe Ala Ile Tyr Asp Thr
65                  70                  75                  80

Ile Gln His Ile Lys Pro Asp Val Gln Thr Ile Cys Ile Gly Met Ala
                85                  90                  95

Ala Ser Met Gly Ser Phe Leu Leu Ala Ala Gly Ala Lys Gly Lys Arg
            100                 105                 110

Phe Ala Leu Pro Asn Ala Glu Val Met Ile His Gln Pro Leu Gly Gly
        115                 120                 125

Ala Gln Gly Gln Ala Thr Glu Ile Glu Ile Ala Ala Asn His Ile Leu
    130                 135                 140

Lys Thr Arg Glu Lys Leu Asn Arg Ile Leu Ser Glu Arg Thr Gly Gln
145                 150                 155                 160

Ser Ile Glu Lys Ile Gln Gln Asp Thr Asp Arg Asp Asn Phe Leu Thr
                165                 170                 175

Ala Ala Glu Ala Lys Glu Tyr Gly Leu Ile Asp Glu Val Met Glu Pro
            180                 185                 190

Glu Lys
```

<210> SEQ ID NO 5
<211> LENGTH: 597
<212> TYPE: DNA
<213> ORGANISM: Listeria welshimeri serovar 6b str. SLCC5334

```
<400> SEQUENCE: 5
atgaacttaa ttccaacagt aattgaacaa acaagccgtg gtgaacgcgc atatgacatt      60
tattcacgtt tattaaaaga cagaattatt atgttaggct ctgcaattga tgataacgtt     120
gctaactcta tcgtttctca attattattc cttgatgcac aagatcctga aaagatatt      180 ttcttatata tcaattctcc aggaggaagt atttcagctg gtatggcgat ttatgataca     240
atgaatttcg ttaaagcaga tgtgcaaact attggtatgg ggatggctgc ttccatggga     300
tcattcttac taacagccgg tgcaaacggt aaacgctttg ccttaccaaa tgcggaaatc     360
atgattcacc aaccacttgg tggcgctcaa ggtcaagcaa ctgaaatcga aattgctgct     420
cgtcacattt tgaaaatcaa agaacgtatg aatactatta tgtctgaaaa aactggtcaa     480
ccatatgaag ttattgctcg tgatacagat cgtgataatt tcatgactgc tcaagaagca     540
aaagattacg gcttaattga tgatatcatc gtaaacaaag ctggcttaaa gggctaa       597

<210> SEQ ID NO 6
<211> LENGTH: 198
<212> TYPE: PRT
<213> ORGANISM: Listeria welshimeri serovar 6b str. SLCC5334

<400> SEQUENCE: 6

Met Asn Leu Ile Pro Thr Val Ile Glu Gln Thr Ser Arg Gly Glu Arg
1               5                   10                  15

Ala Tyr Asp Ile Tyr Ser Arg Leu Leu Lys Asp Arg Ile Ile Met Leu
            20                  25                  30

Gly Ser Ala Ile Asp Asp Asn Val Ala Asn Ser Ile Val Ser Gln Leu
        35                  40                  45

Leu Phe Leu Asp Ala Gln Asp Pro Glu Lys Asp Ile Phe Leu Tyr Ile
    50                  55                  60

Asn Ser Pro Gly Gly Ser Ile Ser Ala Gly Met Ala Ile Tyr Asp Thr
65                  70                  75                  80

Met Asn Phe Val Lys Ala Asp Val Gln Thr Ile Gly Met Gly Met Ala
                85                  90                  95

Ala Ser Met Gly Ser Phe Leu Leu Thr Ala Gly Ala Asn Gly Lys Arg
            100                 105                 110

Phe Ala Leu Pro Asn Ala Glu Ile Met Ile His Gln Pro Leu Gly Gly
        115                 120                 125

Ala Gln Gly Gln Ala Thr Glu Ile Glu Ile Ala Ala Arg His Ile Leu
    130                 135                 140

Lys Ile Lys Glu Arg Met Asn Thr Ile Met Ser Glu Lys Thr Gly Gln
145                 150                 155                 160

Pro Tyr Glu Val Ile Ala Arg Asp Thr Asp Arg Asp Asn Phe Met Thr
                165                 170                 175

Ala Gln Glu Ala Lys Asp Tyr Gly Leu Ile Asp Asp Ile Ile Val Asn
            180                 185                 190

Lys Ala Gly Leu Lys Gly
        195

<210> SEQ ID NO 7
<211> LENGTH: 597
<212> TYPE: DNA
<213> ORGANISM: Listeria monocytogenes str. 4b F2365

<400> SEQUENCE: 7
atgaacttaa ttccaacagt aatcgaacaa actagccgcg gtgaacgtgc atacgacatt      60
tattcccgtt tattaaaaga cagaattatt atgttaggat ctgcaattga tgataacgtg     120
```

-continued

```
gcgaattcga tcgtttctca attactcttc ttagatgcac aagatcctga aaagatatt      180 ttcctatata tcaattcacc aggtggaagt atttcagctg gtatggccat ttacgataca     240
atgaatttcg ttaaagcgga cgtacaaact atcggcatgg gtatggcagc ttccatgggc    300
tcattcttac taacagctgg tgcaaatggc aaacggtttg ccttgccaaa cgctgaaatt    360
atgattcacc aaccacttgg tggcgctcaa ggtcaagcga ctgaaatcga aatcgctgct    420
cgccacattt taaaaatcaa agaacgtatg aatacgatta tggctgagaa aactggtcaa    480
ccgtatgaag tcattgctcg tgatacagat cgtgataatt tcatgactgc acaagaagca    540
aaagattacg gcttaattga tgatatcatc attaacaaat ctggcttaaa aggctaa       597
```

```
<210> SEQ ID NO 8
<211> LENGTH: 198
<212> TYPE: PRT
<213> ORGANISM: Listeria monocytogenes str. 4b F2365

<400> SEQUENCE: 8

Met Asn Leu Ile Pro Thr Val Ile Glu Gln Thr Ser Arg Gly Glu
1               5                   10                  15

Ala Tyr Asp Ile Tyr Ser Arg Leu Leu Lys Asp Arg Ile Ile Met Leu
            20                  25                  30

Gly Ser Ala Ile Asp Asp Asn Val Ala Asn Ser Ile Val Ser Gln Leu
        35                  40                  45

Leu Phe Leu Asp Ala Gln Asp Pro Glu Lys Asp Ile Phe Leu Tyr Ile
    50                  55                  60

Asn Ser Pro Gly Gly Ser Ile Ser Ala Gly Met Ala Ile Tyr Asp Thr
65                  70                  75                  80

Met Asn Phe Val Lys Ala Asp Val Gln Thr Ile Gly Met Gly Met Ala
                85                  90                  95

Ala Ser Met Gly Ser Phe Leu Leu Thr Ala Gly Ala Asn Gly Lys Arg
            100                 105                 110

Phe Ala Leu Pro Asn Ala Glu Ile Met Ile His Gln Pro Leu Gly Gly
        115                 120                 125

Ala Gln Gly Gln Ala Thr Glu Ile Glu Ile Ala Ala Arg His Ile Leu
    130                 135                 140

Lys Ile Lys Glu Arg Met Asn Thr Ile Met Ala Glu Lys Thr Gly Gln
145                 150                 155                 160

Pro Tyr Glu Val Ile Ala Arg Asp Thr Asp Arg Asp Asn Phe Met Thr
                165                 170                 175

Ala Gln Glu Ala Lys Asp Tyr Gly Leu Ile Asp Asp Ile Ile Ile Asn
            180                 185                 190

Lys Ser Gly Leu Lys Gly
        195
```

```
<210> SEQ ID NO 9
<211> LENGTH: 52
<212> TYPE: DNA
<213> ORGANISM: Artificial sequence
<220> FEATURE:
<221> NAME/KEY: source
<223> OTHER INFORMATION: Para-nitrobenzyl esterase B. subtilis 168
      forward primer

<400> SEQUENCE: 9
ggggacaagt ttgtacaaaa aagcaggcta catgactcat caaatagtaa cg           52
```

-continued

```
<210> SEQ ID NO 10
<211> LENGTH: 51
<212> TYPE: DNA
<213> ORGANISM: Artificial sequence
<220> FEATURE:
<221> NAME/KEY: source
<223> OTHER INFORMATION: Para-nitrobenzyl esterase B. subtilis 168
      reverse primer

<400> SEQUENCE: 10
ggggaccact tgtacaaga aagctgggtg ttattctcct tttgaaggga a              51

<210> SEQ ID NO 11
<211> LENGTH: 55
<212> TYPE: DNA
<213> ORGANISM: Artificial sequence
<220> FEATURE:
<221> NAME/KEY: source
<223> OTHER INFORMATION: Penicillin-binding protein 4* B. subtilis 168
      forward primer

<400> SEQUENCE: 11
ggggacaagt ttgtacaaaa aagcaggcta catgaagcag aataaaagaa agcat        55

<210> SEQ ID NO 12
<211> LENGTH: 47
<212> TYPE: DNA
<213> ORGANISM: Artificial sequence
<220> FEATURE:
<221> NAME/KEY: source
<223> OTHER INFORMATION: Penicillin-binding protein 4* B. subtilis 168
      reverse primer

<400> SEQUENCE: 12
ggggaccact tgtacaaga aagctgggtg ctacttcgta cggaccg                  47

<210> SEQ ID NO 13
<211> LENGTH: 51
<212> TYPE: DNA
<213> ORGANISM: Artificial Sequence
<220> FEATURE:
<221> NAME/KEY: source
<223> OTHER INFORMATION: Aldehyde dehydrogenase B E. coli K12 forward
      primer

<400> SEQUENCE: 13
gacaagtttg tacaaaaaag caggctacat gaccaataat cccccttcag c            51

<210> SEQ ID NO 14
<211> LENGTH: 53
<212> TYPE: DNA
<213> ORGANISM: Artificial sequence
<220> FEATURE:
<221> NAME/KEY: source
<223> OTHER INFORMATION: Aldehyde dehydrogenase B E. coli K12 reverse
      primer

<400> SEQUENCE: 14
ggggaccact tgtacaaga aagctgggtg tcagaacagc cccaacggtt tat           53

<210> SEQ ID NO 15
<211> LENGTH: 56
<212> TYPE: DNA
<213> ORGANISM: Artificial sequence
<220> FEATURE:
<221> NAME/KEY: source
<223> OTHER INFORMATION: ATP-dependent Clp protease, proteolytic
      subunit, ClpP P. putida KT2440 forward primer
```

```
<400> SEQUENCE: 15
ggggacaagt tgtacaaaa aagcaggcta catgtcccgc aattcttata ttcagc        56

<210> SEQ ID NO 16
<211> LENGTH: 48
<212> TYPE: DNA
<213> ORGANISM: Artificial sequence
<220> FEATURE:
<221> NAME/KEY: source
<223> OTHER INFORMATION: ATP-dependent Clp protease, proteolytic
      subunit, ClpP P. putida KT2440 reverse primer

<400> SEQUENCE: 16
ggggaccact ttgtacaaga aagctgggtg tcaggaggcc agttgccg               48

<210> SEQ ID NO 17
<211> LENGTH: 54
<212> TYPE: DNA
<213> ORGANISM: Artificial sequence
<220> FEATURE:
<221> NAME/KEY: source
<223> OTHER INFORMATION: CTP Synthase, B. subtilis 168 forward primer

<400> SEQUENCE: 17
ggggacaagt ttgtacaaaa aagcaggcta catgacgaaa tatattttg taac        54

<210> SEQ ID NO 18
<211> LENGTH: 46
<212> TYPE: DNA
<213> ORGANISM: Artificial sequence
<220> FEATURE:
<221> NAME/KEY: source
<223> OTHER INFORMATION: CTP Synthase, B. subtilis 168 reverse primer

<400> SEQUENCE: 18
gaccactttg tacaagaaag ctgggtgtta cttctgattt gcagct                46

<210> SEQ ID NO 19
<211> LENGTH: 53
<212> TYPE: DNA
<213> ORGANISM: Artificial Sequence
<220> FEATURE:
<221> NAME/KEY: source
<223> OTHER INFORMATION: FabF beta ketoacyl carrier synthase II, L.
      welshimeri, serovar 6b - SLCC5334 forward primer

<400> SEQUENCE: 19
ggggacaagt ttgtacaaaa aagcaggcta catggataaa aaaagagtag ttg        53

<210> SEQ ID NO 20
<211> LENGTH: 54
<212> TYPE: DNA
<213> ORGANISM: Artificial sequence
<220> FEATURE:
<221> NAME/KEY: source
<223> OTHER INFORMATION: FabF beta ketoacyl carrier synthase II, L.
      welshimeri, serovar 6b - SLCC5334 reverse primer

<400> SEQUENCE: 20
ggggaccact ttgtacaaga aagctgggtg ttagtcttct attctttaa atac         54

<210> SEQ ID NO 21
<211> LENGTH: 52
<212> TYPE: DNA
<213> ORGANISM: Artificial sequence
```

```
<220> FEATURE:
<221> NAME/KEY: source
<223> OTHER INFORMATION: Lipase L. welshimeri serovar 6b - SLCC forward
      primer

<400> SEQUENCE: 21
ggggacaagt tgtacaaaaa aagcaggcta catgaaaaat acaataaaat gg          52

<210> SEQ ID NO 22
<211> LENGTH: 49
<212> TYPE: DNA
<213> ORGANISM: Artificial sequence
<220> FEATURE:
<221> NAME/KEY: source
<223> OTHER INFORMATION: Lipase L. welshimeri serovar 6b - SLCC reverse
      primer

<400> SEQUENCE: 22
ggggaccact ttgtacaaga aagctgggtg ttacttttct tctaagaac              49

<210> SEQ ID NO 23
<211> LENGTH: 49
<212> TYPE: DNA
<213> ORGANISM: Artificial sequence
<220> FEATURE:
<221> NAME/KEY: source
<223> OTHER INFORMATION: Proline iminopeptidase, P. putida KT2440
      forward primer

<400> SEQUENCE: 23
ggggacaagt tgtacaaaaa aagcaggcta catgcagacc ctctacccg              49

<210> SEQ ID NO 24
<211> LENGTH: 51
<212> TYPE: DNA
<213> ORGANISM: Artificial sequence
<220> FEATURE:
<221> NAME/KEY: source
<223> OTHER INFORMATION: Proline iminopeptidase, P. putida KT2440
      reverse primer

<400> SEQUENCE: 24
ggggaccact ttgtacaaga aagctgggtg tcatgcttct tccagaggca a           51

<210> SEQ ID NO 25
<211> LENGTH: 52
<212> TYPE: DNA
<213> ORGANISM: Artificial sequence
<220> FEATURE:
<221> NAME/KEY: source
<223> OTHER INFORMATION: S-formylglutathione hydrolase, E. coli K12
      forward primer

<400> SEQUENCE: 25
ggggacaagt tgtacaaaaa aagcaggcta catggaactc attgaaaaac at          52

<210> SEQ ID NO 26
<211> LENGTH: 51
<212> TYPE: DNA
<213> ORGANISM: Artificial sequence
<220> FEATURE:
<221> NAME/KEY: source
<223> OTHER INFORMATION: S-formylglutathione hydrolase, E. coli K12
      reverse primer

<400> SEQUENCE: 26
ggggaccact ttgtacaaga aagctgggtg tcaacgcata ttcagtttat t           51
```